(12) United States Patent
Schirrmacher et al.

(10) Patent No.: US 7,842,782 B2
(45) Date of Patent: Nov. 30, 2010

(54) HEPARANASE-DERIVED PEPTIDES FOR VACCINATION OF TUMOR PATIENTS

(75) Inventors: Volker Schirrmacher, Heidelberg (DE); Philipp Beckhove, Heidelberg (DE); Nora Sommerfeldt, Eppelheim (DE)

(73) Assignee: Deutsches Krebsforschungszentrum Stiftung Des Öffentlichen Rechts, Heidelberg (DE)

( * ) Notice: Subject to any disclaimer, the term of this patent is extended or adjusted under 35 U.S.C. 154(b) by 581 days.

(21) Appl. No.: 10/557,249

(22) PCT Filed: May 18, 2004

(86) PCT No.: PCT/EP2004/005332

§ 371 (c)(1),
(2), (4) Date: Oct. 31, 2006

(87) PCT Pub. No.: WO2004/101780

PCT Pub. Date: Nov. 25, 2004

(65) Prior Publication Data

US 2007/0253970 A1    Nov. 1, 2007

(30) Foreign Application Priority Data

May 19, 2003    (EP) .................................. 03011038

(51) Int. Cl.
  *C07K 5/04*    (2006.01)
(52) U.S. Cl. ..................................... 530/328
(58) Field of Classification Search ................ 530/300, 530/328, 350; 514/2, 15; 424/185.1
See application file for complete search history.

(56) References Cited

FOREIGN PATENT DOCUMENTS

| | | |
|---|---|---|
| DE | 199 55 803 A1 | 5/2001 |
| WO | WO 99/21975 A1 | 5/1999 |
| WO | WO 99/40207 A1 | 8/1999 |
| WO | WO 00/52178 A | 9/2000 |
| WO | WO 01/21814 A | 3/2001 |
| WO | WO 03/006645 A | 1/2003 |

OTHER PUBLICATIONS

UniProt™ Database Accession No. Q9Y251 (Sequence Version 1, Nov. 1, 1999).*
Rammensee et al., "SYFPEITHI: Database for MHC ligands and peptide motifs," *Immunogenetics*, vol. 50, No. 3-4, Nov. 1999, pp. 213-219.
Moingeon, "Cancer Vaccines," *Vaccine*, Butterworth Scientific, Guildford, GB, vol. 19, No. 11-12, 8 Dec. 8, 2001, pp. 1305-1326.
Vlodavsky et al., "Mammalian heparanase: involvement in cancer metastasis, angiogenesis and normal development," *Seminars in Cancer Biology*, US, Apr. 2002, vol. 12, No. 2, pp. 121-129.
Krausa et al., "HLA-A2 polymorphism and immune functions," *European Journal of Immunogenetics*, vol. 23, No. 4, 1996, pp. 261-274.

\* cited by examiner

*Primary Examiner*—Stephen L Rawlings
(74) *Attorney, Agent, or Firm*—Foley & Lardner LLP

(57) ABSTRACT

Disclosed is a vaccine against diseases, particularly tumor diseases, being associated with an enhanced heparanase expression and/or activity, wherein the vaccine contains a heparanase peptide, which binds to a HLA molecule.

3 Claims, 22 Drawing Sheets

TABLE 1

| | HLA-A*0201 nonamers | | |
|---|---|---|---|
| Number | Pos | 1 2 3 4 5 6 7 8 9 | score |
| 1 | 16 | LLLGPLGPL | 31 |
| 2 | 8 | ALPPPLMLL | 29 |
| 3 | 183 | DLIFGLNAL | 28 |
| 4 | 315 | VLDIFISSV | 28 |
| 5 | 13 | LMLLLLGPL | 27 |
| 6 | 72 | LILLGSPKL | 27 |
| 7 | 310 | FLNPDVLDI | 27 |
| 8 | 184 | LIFGLNALL | 26 |
| 9 | 487 | GLLSKSVQL | 26 |
| 10 | 408 | LLFKKLVGT | 25 |
| 11 | 1 | MLLRSKPAL | 24 |
| 12 | 44 | FTQEPLHLV | 23 |
| 13 | 79 | KLRTLARGL | 23 |
| 14 | 187 | GLNALLRTA | 23 |
| 15 | 346 | SAYGGGAPL | 23 |
| 16 | 494 | QLNGLTLKM | 23 |
| 17 | 64 | NLATDPRFL | 22 |
| 18 | 82 | TLARGLSPA | 22 |
| 19 | 241 | QLGEDFIQL | 22 |
| 20 | 363 | FMWLDKLGL | 22 |
| 21 | 372 | SARMGIEVV | 22 |
| 22 | 400 | PLPDYWLSL | 22 |
| 23 | 405 | WLSLLFKKL | 22 |
| 24 | 51 | LVSPSFLSV | 21 |
| 25 | 75 | LGSPKLRTL | 21 |
| 26 | 180 | SGLDLIFGL | 21 |
| 27 | 299 | YLNGRTATR | 21 |
| 28 | 430 | KLRVYLHCT | 21 |
| 29 | 456 | NLHNVTKYL | 21 |
| 30 | 33 | AQAQDVVDL | 20 |
| 31 | 189 | NALLRTADL | 20 |
| 32 | 282 | FLKAGGEVI | 20 |
| 33 | 285 | AGGEVIDSV | 20 |
| 34 | 318 | IFISSVQKV | 20 |
| 35 | 66 | ATDPRFLIL | 19 |
| 36 | 91 | YLRFGGTKT | 19 |
| 37 | 361 | AGFMWLDKL | 19 |
| 38 | 412 | KLVGTKVLM | 19 |
| 39 | 415 | GTKVLMASV | 19 |
| 40 | 449 | DLTLYAINL | 19 |
| 41 | 452 | LYAINLHNV | 19 |
| 42 | 478 | YLLRPLGPH | 19 |

TABLE 1 (Continued)

| 43 | 492 | SVQLN<u>G</u>LTL | 19 |
|---|---|---|---|
| 44 | 15 | LLLLG<u>P</u>LGP | 18 |
| 45 | 74 | LLGSP<u>K</u>LRT | 18 |
| 46 | 131 | SIPPD<u>V</u>EEK | 18 |
| 47 | 174 | YTFAN<u>C</u>SGL | 18 |
| 48 | 206 | LLLDY<u>C</u>SSK | 18 |
| 49 | 229 | FLKKA<u>D</u>IFI | 18 |
| 50 | 234 | DIFIN<u>G</u>SQL | 18 |
| 51 | 262 | KLYGP<u>D</u>VGQ | 18 |
| 52 | 277 | KMLKS<u>F</u>LKA | 18 |
| 53 | 365 | WLDKL<u>G</u>LSA | 18 |
| 54 | 376 | GIEVV<u>M</u>RQV | 18 |
| 55 | 393 | LVDEN<u>F</u>DPL | 18 |
| 56 | 490 | SKSVQ<u>L</u>NGL | 18 |
| 57 | 7 | PALPP<u>P</u>LML | 17 |
| 58 | 176 | FANCS<u>G</u>LDL | 17 |
| 59 | 248 | QLHKL<u>L</u>RKS | 17 |
| 60 | 321 | SSVQK<u>V</u>FQV | 17 |
| 61 | 347 | AYGGG<u>A</u>PLL | 17 |
| 62 | 418 | VLMAS<u>V</u>QGS | 17 |
| 63 | 9 | LPPPL<u>M</u>LLL | 16 |
| 64 | 17 | LLGPL<u>G</u>PLS | 16 |
| 65 | 20 | PLGPL<u>S</u>PGA | 16 |
| 66 | 56 | FLSVT<u>I</u>DAN | 16 |
| 67 | 60 | TIDAN<u>L</u>ATD | 16 |
| 68 | 142 | LEWPY<u>Q</u>EQL | 16 |
| 69 | 151 | LLREH<u>Y</u>QKK | 16 |
| 70 | 165 | YSRSS<u>V</u>DVL | 16 |
| 71 | 177 | ANCSG<u>L</u>DLI | 16 |
| 72 | 222 | LGNEP<u>N</u>SFL | 16 |
| 73 | 252 | LLRKS<u>T</u>FKN | 16 |
| 74 | 281 | SFLKA<u>G</u>GEV | 16 |
| 75 | 292 | SVTWH<u>H</u>YYL | 16 |
| 76 | 303 | RTATR<u>E</u>DFL | 16 |
| 77 | 322 | SVQKV<u>F</u>QVV | 16 |
| 78 | 325 | KVFQV<u>V</u>EST | 16 |
| 79 | 353 | PLLSD<u>T</u>FAA | 16 |
| 80 | 354 | LLSDT<u>F</u>AAG | 16 |
| 81 | 371 | LSARM<u>G</u>IEV | 16 |
| 82 | 386 | FGAGN<u>Y</u>HLV | 16 |
| 83 | 411 | KKLVG<u>T</u>KVL | 16 |
| 84 | 413 | LVGTK<u>V</u>LMA | 16 |
| 85 | 444 | RYKEG<u>D</u>LTL | 16 |
| 86 | 479 | LLRPL<u>G</u>PHG | 16 |
| 87 | 480 | LRPLG<u>P</u>HGL | 16 |
| 88 | 488 | LLSKS<u>V</u>QLN | 16 |
| 89 | 503 | VDDQT<u>L</u>PPL | 16 |
| 90 | 514 | KPLRP<u>G</u>SSL | 16 |

TABLE 1 (Continued)

| 91 | 516 | LRPGS S LGL | 16 |
|---|---|---|---|
| 92 | 533 | VIRNA K VAA | 16 |
| 93 | 2 | LLRSK P ALP | 15 |
| 94 | 12 | PLMLL L GP | 15 |
| 95 | 27 | GALPR P AQA | 15 |
| 96 | 65 | LATDP R FLI | 15 |
| 97 | 67 | TDPRF L ILL | 15 |
| 98 | 73 | ILLGS P KLR | 15 |
| 99 | 132 | IPPDV E EKL | 15 |
| 100 | 150 | LLLRE H YQK | 15 |
| 101 | 244 | EDFIQ L HKL | 15 |
| 102 | 260 | NAKLY G PDV | 15 |
| 103 | 333 | TRPGK K VWL | 15 |
| 104 | 401 | LPDYW L SLL | 15 |
| 105 | 407 | SLLFK K LVG | 15 |
| 106 | 454 | AINLH N VTK | 15 |
| 107 | 481 | RPLGP H GLL | 15 |
| 108 | 495 | LNGLT L KMV | 15 |
| 109 | 500 | LKMVD D QTL | 15 |
| 110 | 506 | QTLPP L MEK | 15 |
| 111 | 507 | TLPPL M EKP | 15 |
| 112 | 521 | SLGLP A FSY | 15 |
| 113 | 523 | GLPAF S YSF | 15 |
| 114 | 531 | FFVIR N AKV | 15 |
| 115 | 5 | SKPAL P PPL | 14 |
| 116 | 14 | MLLLL G PLG | 14 |
| 117 | 28 | ALPRP A QAQ | 14 |
| 118 | 49 | LHLVS P SFL | 14 |
| 119 | 53 | SPSFL S VTI | 14 |
| 120 | 57 | LSVTI D ANL | 14 |
| 121 | 59 | VTIDA N LAT | 14 |
| 122 | 71 | FLILL G SPK | 14 |
| 123 | 84 | ARGLS P AYL | 14 |
| 124 | 86 | GLSPA Y LRF | 14 |
| 125 | 94 | FGGTK T DFL | 14 |
| 126 | 102 | LIFDP K KES | 14 |
| 127 | 172 | VLYTF A NCS | 14 |
| 128 | 190 | ALLRT A DLQ | 14 |
| 129 | 205 | QLLLD Y CSS | 14 |
| 130 | 214 | KGYNI S WEL | 14 |
| 131 | 236 | FINGS Q LGE | 14 |
| 132 | 251 | KLLRK S TFK | 14 |
| 133 | 255 | KSTFK N AKL | 14 |
| 134 | 275 | TAKML K SFL | 14 |
| 135 | 278 | MLKSF L KAG | 14 |
| 136 | 350 | GGAPL L SDT | 14 |
| 137 | 358 | TFAAG F MWL | 14 |
| 138 | 374 | RMGIE V VMR | 14 |

TABLE 1 (Continued)

| | | | |
|---|---|---|---|
| 139 | 380 | VMRQV<u>F</u>FGA | 14 |
| 140 | 385 | FFGAG<u>N</u>YHL | 14 |
| 141 | 406 | LSLL<u>F</u>KKLV | 14 |
| 142 | 419 | LMASV<u>Q</u>GSK | 14 |
| 143 | 423 | VQGSK<u>R</u>RKL | 14 |
| 144 | 427 | KRRKL<u>R</u>VYL | 14 |
| 145 | 453 | YAINL<u>H</u>NVT | 14 |
| 146 | 463 | YLRLP<u>Y</u>PFS | 14 |
| 147 | 475 | VDKYL<u>L</u>RPL | 14 |
| 148 | 511 | LMEKP<u>L</u>RPG | 14 |
| 149 | 21 | LGPLS<u>P</u>GAL | 13 |
| 150 | 40 | DLDFF<u>T</u>QEP | 13 |
| 151 | 101 | FLIFD<u>P</u>KKE | 13 |
| 152 | 124 | QDICK<u>Y</u>GSI | 13 |
| 153 | 149 | QLLLR<u>E</u>HYQ | 13 |
| 154 | 191 | LLRTA<u>D</u>LQW | 13 |
| 155 | 196 | DLQWN<u>S</u>SNA | 13 |
| 156 | 198 | QWNSS<u>N</u>AQL | 13 |
| 157 | 207 | LLDYC<u>S</u>SKG | 13 |
| 158 | 339 | VWLGE<u>T</u>SSA | 13 |
| 159 | 340 | WLGET<u>S</u>SAY | 13 |
| 160 | 369 | LGLSA<u>R</u>MGI | 13 |
| 161 | 398 | FDPLP<u>D</u>YWL | 13 |
| 162 | 497 | GLTLK<u>M</u>VDD | 13 |
| 163 | 499 | TLKMV<u>D</u>DQT | 13 |
| 164 | 525 | PAFSY<u>S</u>FFV | 13 |
| 165 | 10 | PPPLM<u>L</u>LLL | 12 |
| 166 | 23 | PLSPG<u>A</u>LPR | 12 |
| 167 | 31 | RPAQA<u>Q</u>DVV | 12 |
| 168 | 41 | LDFFT<u>Q</u>EPL | 12 |
| 169 | 128 | KYGSI<u>P</u>PDV | 12 |
| 170 | 139 | KLRLE<u>W</u>PYQ | 12 |
| 171 | 141 | RLEWP<u>Y</u>QEQ | 12 |
| 172 | 144 | WPYQE<u>Q</u>LLL | 12 |
| 173 | 164 | TYSRS<u>S</u>VDV | 12 |
| 174 | 186 | FGLNA<u>L</u>LRT | 12 |
| 175 | 210 | YCSSK<u>G</u>YNI | 12 |
| 176 | 217 | NISWE<u>L</u>GNE | 12 |
| 177 | 227 | NSFLK<u>K</u>ADI | 12 |
| 178 | 232 | KADIF<u>I</u>NGS | 12 |
| 179 | 274 | KTAKM<u>L</u>KSF | 12 |
| 180 | 410 | FKKLV<u>G</u>TKV | 12 |
| 181 | 434 | YLHCT<u>N</u>TDN | 12 |
| 182 | 450 | LTLYA<u>I</u>NLH | 12 |
| 183 | 451 | TLYAI<u>N</u>LHN | 12 |
| 184 | 458 | HNVTK<u>Y</u>LRL | 12 |
| 185 | 498 | LTLKM<u>V</u>DDQ | 12 |
| 186 | 510 | PLMEK<u>P</u>LRP | 12 |

TABLE 1 (Continued)

| | | | |
|---|---|---|---|
| 187 | 535 | RNAKVAACI | 12 |
| 188 | 43 | FFTQEPLHL | 11 |
| 189 | 50 | HLVSPSFLS | 11 |
| 190 | 83 | LARGLSPAY | 11 |
| 191 | 103 | IFDPKKEST | 11 |
| 192 | 121 | QVNQDICKY | 11 |
| 193 | 169 | SVDVLYTFA | 11 |
| 194 | 181 | GLDLIFGLN | 11 |
| 195 | 200 | NSSNAQLLL | 11 |
| 196 | 239 | GSQLGEDFI | 11 |
| 197 | 245 | DFIQLHKLL | 11 |
| 198 | 270 | QPRRKTAKM | 11 |
| 199 | 284 | KAGGEVIDS | 11 |
| 200 | 289 | VIDSVTWHH | 11 |
| 201 | 298 | YYLNGRTAT | 11 |
| 202 | 307 | REDFLNPDV | 11 |
| 203 | 368 | KLGLSARMG | 11 |
| 204 | 370 | GLSARMGIE | 11 |
| 205 | 373 | ARMGIEVVM | 11 |
| 206 | 392 | HLVDENFDP | 11 |
| 207 | 404 | YWLSLLFKK | 11 |
| 208 | 425 | GSKRRKLRV | 11 |
| 209 | 447 | EGDLTLYAI | 11 |
| 210 | 472 | NKQVDKYLL | 11 |
| 211 | 483 | LGPHGLLSK | 11 |
| 212 | 508 | LPPLMEKPL | 11 |
| 213 | 515 | PLRPGSSLG | 11 |
| 214 | 534 | IRNAKVAAC | 11 |
| 215 | 19 | GPLGPLSPG | 10 |
| 216 | 48 | PLHLVSPSF | 10 |
| 217 | 52 | VSPSFLSVT | 10 |
| 218 | 55 | SFLSVTIDA | 10 |
| 219 | 58 | SVTIDANLA | 10 |
| 220 | 92 | LRFGGIKTD | 10 |
| 221 | 130 | GSIPPDVEE | 10 |
| 222 | 134 | PDVEEKLRL | 10 |
| 223 | 162 | NSTYSRSSV | 10 |
| 224 | 168 | SSVDVLYTF | 10 |
| 225 | 182 | LDLIFGLNA | 10 |
| 226 | 199 | WNSSNAQLL | 10 |
| 227 | 202 | SNAQLLLDY | 10 |
| 228 | 221 | ELGNEPNSF | 10 |
| 229 | 246 | FIQLHKLLR | 10 |
| 230 | 247 | IQLHKLLRK | 10 |
| 231 | 267 | DVGQPRRKT | 10 |
| 232 | 283 | LKAGGEVID | 10 |
| 233 | 317 | DIFISSVQK | 10 |
| 234 | 336 | GKKVWLGET | 10 |

TABLE 1 (Continued)

| 235 | 338 | K V W L G E T S S | 10 |
|---|---|---|---|
| 236 | 359 | F A A G F M W L D | 10 |
| 237 | 367 | D K L G L S A R M | 10 |
| 238 | 379 | V V M R Q V F F G | 10 |
| 239 | 442 | N P R Y K E G D L | 10 |
| 240 | 446 | K E G D L T L Y A | 10 |
| 241 | 455 | I N L H N V T K Y | 10 |
| 242 | 465 | R L P Y P F S N K | 10 |
| 243 | 471 | S N K Q V D K Y L | 10 |
| 244 | 474 | Q V D K Y L L R P | 10 |
| 245 | 482 | P L G P H G L L S | 10 |
| 246 | 484 | G P H G L L S K S | 10 |
| 247 | 501 | K M V D D Q T L P | 10 |
| 248 | 529 | Y S F F V I R N A | 10 |
| 249 | 532 | F V I R N A K V A | 10 |
| 250 | 6 | K P A L P P P L M | 9 |
| 251 | 24 | L S P G A L P R P | 9 |
| 252 | 34 | Q A Q D V V D L D | 9 |
| 253 | 37 | D V V D L D F F T | 9 |
| 254 | 70 | R F L I L L G S P | 9 |
| 255 | 81 | R T L A R G L S P | 9 |
| 256 | 98 | K T D F L I F D P | 9 |
| 257 | 110 | S T F E E R S Y W | 9 |
| 258 | 135 | D V E E K L R L E | 9 |
| 259 | 156 | Y Q K K F K N S T | 9 |
| 260 | 167 | R S S V D V L Y T | 9 |
| 261 | 203 | N A Q L L L D Y C | 9 |
| 262 | 218 | I S W E L G N E P | 9 |
| 263 | 258 | F K N A K L Y G P | 9 |
| 264 | 305 | A T R E D F L N P | 9 |
| 265 | 312 | N P D V L D I F I | 9 |
| 266 | 332 | S T R P G K K V W | 9 |
| 267 | 349 | G G G A P L L S D | 9 |
| 268 | 389 | G N Y H L V D E N | 9 |
| 269 | 417 | K V L M A S V Q G | 9 |
| 270 | 432 | R V Y L H C T N T | 9 |
| 271 | 464 | L R L P Y P F S N | 9 |
| 272 | 466 | L P Y P F S N K Q | 9 |
| 273 | 485 | P H G L L S K S V | 9 |
| 274 | 493 | V Q L N G L T L K | 9 |
| 275 | 519 | G S S L G L P A F | 9 |
| 276 | 520 | S S L G L P A F S | 9 |
| 277 | 526 | A F S Y S F F V I | 9 |
| 278 | 46 | Q E P L H L V S P | 8 |
| 279 | 95 | G G T K T D F L I | 8 |
| 280 | 118 | W Q S Q V N Q D I | 8 |
| 281 | 125 | D I C K Y G S I P | 8 |
| 282 | 127 | C K Y G S I P P D | 8 |

TABLE 1 (Continued)

| | | | |
|---|---|---|---|
| 283 | 193 | RTADLQWNS | 8 |
| 284 | 201 | SSNAQLLLD | 8 |
| 285 | 225 | EPNSFLKKA | 8 |
| 286 | 237 | INGSQLGED | 8 |
| 287 | 263 | LYGPDVGQP | 8 |
| 288 | 268 | VGQPRRKTA | 8 |
| 289 | 288 | EVIDSVTWH | 8 |
| 290 | 308 | EDFLNPDVL | 8 |
| 291 | 314 | DVLDIFISS | 8 |
| 292 | 319 | FISSVQKVF | 8 |
| 293 | 328 | QVVESTRPG | 8 |
| 294 | 331 | ESTRPGKKV | 8 |
| 295 | 351 | GAPLLSDTF | 8 |
| 296 | 352 | APLLSDTFA | 8 |
| 297 | 364 | MWLDKLGLS | 8 |
| 298 | 366 | LDKLGLSAR | 8 |
| 299 | 375 | MGIEVVMRQ | 8 |
| 300 | 388 | AGNYHLVDE | 8 |
| 301 | 409 | LFKKLVGTK | 8 |
| 302 | 422 | SVQGSKRRK | 8 |
| 303 | 433 | VYLHCTNTD | 8 |
| 304 | 439 | NTDNPRYKE | 8 |
| 305 | 459 | NVTKYLRLP | 8 |
| 306 | 470 | FSNKQVDKY | 8 |
| 307 | 502 | MVDDQTLPP | 8 |
| 308 | 18 | LGPLGPLSP | 7 |
| 309 | 25 | SPGALPRPA | 7 |
| 310 | 30 | PRPAQAQDV | 7 |
| 311 | 38 | VVDLDFFTQ | 7 |
| 312 | 87 | LSPAYLRFG | 7 |
| 313 | 89 | PAYLRFGGT | 7 |
| 314 | 90 | AYLRFGGTK | 7 |
| 315 | 117 | YWQSQVNQD | 7 |
| 316 | 140 | LRLEWPYQE | 7 |
| 317 | 146 | YQEQLLLRE | 7 |
| 318 | 147 | QEQLLLREH | 7 |
| 319 | 163 | STYSRSSVD | 7 |
| 320 | 194 | TADLQWNSS | 7 |
| 321 | 242 | LGEDFIQLH | 7 |
| 322 | 249 | LHKLLRKST | 7 |
| 323 | 293 | VTWHHYYLN | 7 |
| 324 | 297 | HYYLNGRTA | 7 |
| 325 | 311 | LNPDVLDIF | 7 |
| 326 | 324 | QKVFQVVES | 7 |
| 327 | 387 | GAGNYHLVD | 7 |
| 328 | 426 | SKRRKLRVY | 7 |
| 329 | 445 | YKEGDLTLY | 7 |
| 330 | 4 | RSKPALPPP | 6 |

TABLE 1 (Continued)

| | | | |
|---|---|---|---|
| 331 | 22 | G P L S P G A L P | 6 |
| 332 | 29 | L P R P A Q A Q D | 6 |
| 333 | 62 | D A N L A T D P R | 6 |
| 334 | 76 | G S P K L R T L A | 6 |
| 335 | 114 | E R S Y W Q S Q V | 6 |
| 336 | 143 | E W P Y Q E Q L L | 6 |
| 337 | 171 | D V L Y T F A N C | 6 |
| 338 | 188 | L N A L L R T A D | 6 |
| 339 | 195 | A D L Q W N S S N | 6 |
| 340 | 204 | A Q L L L D Y C S | 6 |
| 341 | 212 | S S K G Y N I S W | 6 |
| 342 | 216 | Y N I S W E L G N | 6 |
| 343 | 235 | I F I N G S Q L G | 6 |
| 344 | 240 | S Q L G E D F I Q | 6 |
| 345 | 256 | S T F K N A K L Y | 6 |
| 346 | 271 | P R R K T A K M L | 6 |
| 347 | 295 | W H H Y Y L N G R | 6 |
| 348 | 306 | T R E D F L N P D | 6 |
| 349 | 329 | V V E S T R P G K | 6 |
| 350 | 344 | T S S A Y G G G A | 6 |
| 351 | 345 | S S A Y G G G A P | 6 |
| 352 | 355 | L S D T F A A G F | 6 |
| 353 | 360 | A A G F M W L D K | 6 |
| 354 | 383 | Q V F F G A G N Y | 6 |
| 355 | 420 | M A S V Q G S K R | 6 |
| 356 | 437 | C T N T D N P R Y | 6 |
| 357 | 448 | G D L T L Y A I N | 6 |
| 358 | 461 | T K Y L R L P Y P | 6 |
| 359 | 491 | K S V Q L N G L T | 6 |
| 360 | 522 | L G L P A F S Y S | 6 |
| 361 | 528 | S Y S F F V I R N | 6 |
| 362 | 11 | P P L M L L L L G | 5 |
| 363 | 39 | V D L D F F T Q E | 5 |
| 364 | 61 | I D A N L A T D P | 5 |
| 365 | 63 | A N L A T D P R F | 5 |
| 366 | 77 | S P K L R T L A R | 5 |
| 367 | 78 | P K L R T L A R G | 5 |
| 368 | 88 | S P A Y L R F G G | 5 |
| 369 | 96 | G T K T D F L I F | 5 |
| 370 | 97 | T K T D F L I F D | 5 |
| 371 | 100 | D F L I F D P K K | 5 |
| 372 | 116 | S Y W Q S Q V N Q | 5 |
| 373 | 159 | K F K N S T Y S R | 5 |
| 374 | 170 | V D V L Y T F A N | 5 |
| 375 | 192 | L R T A D L Q W N | 5 |
| 376 | 197 | L Q W N S S N A Q | 5 |
| 377 | 213 | S K G Y N I S W E | 5 |
| 378 | 220 | W E L G N E P N S | 5 |

TABLE 1 (Continued)

| | | | |
|---|---|---|---|
| 379 | 228 | SFLKK<u>A</u>DIF | 5 |
| 380 | 230 | LKKAD<u>I</u>FIN | 5 |
| 381 | 233 | ADIFI<u>N</u>GSQ | 5 |
| 382 | 261 | AKLYG<u>P</u>DVG | 5 |
| 383 | 279 | LKSFL<u>K</u>AGG | 5 |
| 384 | 287 | GEVID<u>S</u>VTW | 5 |
| 385 | 296 | HHYYL<u>N</u>GRT | 5 |
| 386 | 334 | RPGKK<u>V</u>WLG | 5 |
| 387 | 348 | YGGGA<u>P</u>LLS | 5 |
| 388 | 384 | VFFGA<u>G</u>NYH | 5 |
| 389 | 391 | YHLVD<u>E</u>NFD | 5 |
| 390 | 396 | ENFDP<u>L</u>PDY | 5 |
| 391 | 403 | DYWLS<u>L</u>LFK | 5 |
| 392 | 414 | VGTKV<u>L</u>MAS | 5 |
| 393 | 460 | VTKYL<u>R</u>LPY | 5 |
| 394 | 462 | KYLRL<u>P</u>YPF | 5 |
| 395 | 467 | PYPFS<u>N</u>KQV | 5 |
| 396 | 477 | KYLLR<u>P</u>LGP | 5 |
| 397 | 504 | DDQTL<u>P</u>PLM | 5 |
| 398 | 527 | FSYSF<u>E</u>VIR | 5 |
| 399 | 530 | SFFVI<u>R</u>NAK | 5 |
| 400 | 3 | LRSKP<u>A</u>LPP | 4 |
| 401 | 36 | QDVVD<u>L</u>DFF | 4 |
| 402 | 47 | EPLHL<u>V</u>SPS | 4 |
| 403 | 68 | DPRFL<u>I</u>LLG | 4 |
| 404 | 69 | PRFLI<u>L</u>LGS | 4 |
| 405 | 85 | RGLSP<u>A</u>YLR | 4 |
| 406 | 104 | FDPKK<u>E</u>STF | 4 |
| 407 | 136 | VEEKL<u>R</u>LEW | 4 |
| 408 | 145 | PYQEQ<u>L</u>LLR | 4 |
| 409 | 161 | KNSTY<u>S</u>RSS | 4 |
| 410 | 166 | SRSSV<u>D</u>VLY | 4 |
| 411 | 178 | NCSGL<u>D</u>LIF | 4 |
| 412 | 179 | CSGLD<u>L</u>IFG | 4 |
| 413 | 231 | KKADI<u>F</u>ING | 4 |
| 414 | 250 | HKLLR<u>K</u>STF | 4 |
| 415 | 253 | LRKST<u>E</u>KNA | 4 |
| 416 | 259 | KNAKL<u>Y</u>GPD | 4 |
| 417 | 265 | GPDVG<u>Q</u>PRR | 4 |
| 418 | 276 | AKMLK<u>S</u>FLK | 4 |
| 419 | 280 | KSFLK<u>A</u>GGE | 4 |
| 420 | 286 | GGEVI<u>D</u>SVT | 4 |
| 421 | 301 | NGRTA<u>T</u>RED | 4 |
| 422 | 309 | DFLNP<u>D</u>VLD | 4 |
| 423 | 320 | ISSVQ<u>K</u>VFQ | 4 |
| 424 | 337 | KKVWL<u>G</u>ETS | 4 |
| 425 | 356 | SDTFA<u>A</u>GFM | 4 |
| 426 | 357 | DTFAA<u>G</u>FMW | 4 |

TABLE 1 (Continued)

| | | | |
|---|---|---|---|
| 427 | 428 | RRKLRVYLH | 4 |
| 428 | 431 | LRVYLHCTN | 4 |
| 429 | 435 | LHCTNIDNP | 4 |
| 430 | 440 | TDNPRYKEG | 4 |
| 431 | 457 | LHNVTKYLR | 4 |
| 432 | 473 | KQVDKYLLR | 4 |
| 433 | 512 | MEKPLRPGS | 4 |
| 434 | 517 | RPGSSLGLP | 4 |
| 435 | 32 | PAQAQDVVD | 3 |
| 436 | 35 | AQDVVDLDF | 3 |
| 437 | 45 | TQEPLHLVS | 3 |
| 438 | 129 | YGSIPPDVE | 3 |
| 439 | 152 | LREHYQKKF | 3 |
| 440 | 185 | IFGLNALLR | 3 |
| 441 | 208 | LDYCSSKGY | 3 |
| 442 | 211 | CSSKGYNIS | 3 |
| 443 | 219 | SWELGNEPN | 3 |
| 444 | 224 | NEPNSFLKK | 3 |
| 445 | 254 | RKSTFKNAK | 3 |
| 446 | 264 | YGPDVGQPR | 3 |
| 447 | 273 | RKTAKMLKS | 3 |
| 448 | 290 | IDSVTWHHY | 3 |
| 449 | 304 | TATREDFLN | 3 |
| 450 | 316 | LDIFISSVQ | 3 |
| 451 | 323 | VQKVFQVVE | 3 |
| 452 | 326 | VFQVVESTR | 3 |
| 453 | 330 | VESTRPGKK | 3 |
| 454 | 341 | LGETSSAYG | 3 |
| 455 | 378 | EVVMRQVFF | 3 |
| 456 | 382 | RQVFFGAGN | 3 |
| 457 | 397 | NFDPLPDYW | 3 |
| 458 | 399 | DPLPDYWLS | 3 |
| 459 | 421 | ASVQGSKRR | 3 |
| 460 | 429 | RKLRVYLHC | 3 |
| 461 | 468 | YPFSNKQVD | 3 |
| 462 | 496 | NGLTLKMVD | 3 |
| 463 | 518 | PGSSLGLPA | 3 |
| 464 | 524 | LPAFSYSFF | 3 |
| 465 | 26 | PGALPRPAQ | 2 |
| 466 | 54 | PSFLSVTID | 2 |
| 467 | 93 | RFGGTKTDF | 2 |
| 468 | 106 | PKKESTFEE | 2 |
| 469 | 107 | KKESTFEER | 2 |
| 470 | 108 | KESTFEERS | 2 |
| 471 | 111 | TFEERSYWQ | 2 |
| 472 | 120 | SQVNQDICK | 2 |
| 473 | 123 | NQDICKYGS | 2 |
| 474 | 126 | ICKYGSIPP | 2 |

TABLE 1 (Continued)

| | | | |
|---|---|---|---|
| 475 | 158 | K K F K N S T Y S | 2 |
| 476 | 160 | F K N S T Y S R S | 2 |
| 477 | 173 | L Y T F A N C S G | 2 |
| 478 | 175 | T F A N C S G L D | 2 |
| 479 | 215 | G Y N I S W E L G | 2 |
| 480 | 223 | G N E P N S F L K | 2 |
| 481 | 269 | G Q P R R K T A K | 2 |
| 482 | 294 | T W H H Y Y L N G | 2 |
| 483 | 300 | L N G R T A T R E | 2 |
| 484 | 342 | G E T S S A Y G G | 2 |
| 485 | 343 | E T S S A Y G G G | 2 |
| 486 | 362 | G F M W L D K L G | 2 |
| 487 | 377 | I E V V M R Q V F | 2 |
| 488 | 381 | M R Q V F F G A G | 2 |
| 489 | 394 | V D E N F D P L P | 2 |
| 490 | 443 | P R Y K E G D L T | 2 |
| 491 | 476 | D K Y L L R P L G | 2 |
| 492 | 486 | H G L L S K S V Q | 2 |
| 493 | 489 | L S K S V Q L N G | 2 |
| 494 | 42 | D F F T Q E P L H | 1 |
| 495 | 80 | L R T L A R G L S | 1 |
| 496 | 99 | T D F L I E D P K | 1 |
| 497 | 115 | R S Y W Q S Q V N | 1 |
| 498 | 122 | V N Q D I C K Y G | 1 |
| 499 | 154 | E H Y Q K K F K N | 1 |
| 500 | 157 | Q K K F K N S T Y | 1 |
| 501 | 238 | N G S Q L G E D F | 1 |
| 502 | 243 | G E D F I Q L H K | 1 |
| 503 | 313 | P D V L D I F I S | 1 |
| 504 | 327 | F Q V V E S T R P | 1 |
| 505 | 441 | D N P R Y K E G D | 1 |

TABLE 2

| | HLA-DRB1*0401 (DR4Dw4) 15 - mers | | |
|---|---|---|---|
| Number | Pos | 1 2 3 4 5 6 7 8 9 0 1 2 3 4 5 | score |
| 1 | 382 | R Q V F F G A G N Y H L V D E | 28 |
| 2 | 528 | S Y S F F V I R N A K V A A C | 28 |
| 3 | 38 | V V D L D F F T Q E P L H L V | 26 |
| 4 | 56 | F L S V T I D A N L A T D P R | 26 |
| 5 | 62 | D A N L A T D P R F L I L L G | 26 |
| 6 | 69 | P R F L I L L G S P K L R T L | 26 |
| 7 | 77 | S P K L R T L A R G L S P A Y | 26 |
| 8 | 167 | R S S V D V L Y T F A N C S G | 26 |
| 9 | 219 | S W E L G N E P N S F L K K A | 26 |
| 10 | 246 | F I Q L H K L L R K S T F K N | 26 |
| 11 | 313 | P D V L D I F I S S V Q K V F | 26 |
| 12 | 41 | L D F F T Q E P L H L V S P S | 22 |
| 13 | 53 | S P S F L S V T I D A N L A T | 22 |
| 14 | 68 | D P R F L I L L G S P K L R T | 22 |
| 15 | 88 | S P A Y L R F G G T K T D F L | 22 |
| 16 | 91 | Y L R F G G T K T D F L I F D | 22 |
| 17 | 115 | R S Y W Q S Q V N Q D I C K Y | 22 |
| 18 | 141 | R L E W P Y Q E Q L L L R E H | 22 |
| 19 | 171 | D V L Y T F A N C S G L D L I | 22 |
| 20 | 279 | L K S F L K A G G E V I D S V | 22 |
| 21 | 295 | W H H Y Y L N G R T A T R E D | 22 |
| 22 | 324 | Q K V F Q V V E S T R P G K K | 22 |
| 23 | 337 | K K V W L G E T S S A Y G G G | 22 |
| 24 | 360 | A A G F M W L D K L G L S A R | 22 |
| 25 | 395 | D E N F D P L P D Y W L S L L | 22 |
| 26 | 402 | P D Y W L S L L F K K L V G T | 22 |
| 27 | 407 | S L L F K K L V G T K V L M A | 22 |
| 28 | 431 | L R V Y L H C T N T D N P R Y | 22 |
| 29 | 450 | L T L Y A I N L H N V T K Y L | 22 |
| 30 | 460 | V T K Y L R L P Y P F S N K Q | 22 |
| 31 | 526 | A F S Y S F F V I R N A K V A | 22 |
| 32 | 10 | P P P L M L L L L G P L G P L | 20 |
| 33 | 18 | L G P L G P L S P G A L P R P | 20 |
| 34 | 35 | A Q D V V D L D F F T Q E P L | 20 |
| 35 | 46 | Q E P L H L V S P S F L S V T | 20 |
| 36 | 99 | T D F L I F D P K K E S T F E | 20 |
| 37 | 129 | Y G S I P P D V E E K L R L E | 20 |
| 38 | 139 | K L R L E W P Y Q E Q L L L R | 20 |
| 39 | 148 | E Q L L L R E H Y Q K K F K N | 20 |
| 40 | 170 | V D V L Y T F A N C S G L D L | 20 |

TABLE 2 (Continued)

| | | | |
|---|---|---|---|
| 41 | 179 | CSGLDLIFGLNALLR | 20 |
| 42 | 181 | GLDLIFGLNALLRTA | 20 |
| 43 | 185 | IFGLNALLRTADLQW | 20 |
| 44 | 189 | NALLRTADLQWNSSN | 20 |
| 45 | 194 | TADLQWNSSNAQLLL | 20 |
| 46 | 203 | NAQLLLDYCSSKGYN | 20 |
| 47 | 227 | NSFLKKADIFINGSQ | 20 |
| 48 | 265 | GPDVGQPRRKTAKML | 20 |
| 49 | 312 | NPDVLDIFISSVQKV | 20 |
| 50 | 317 | DIFISSVQKVFQVVE | 20 |
| 51 | 320 | ISSVQKVFQVVESTR | 20 |
| 52 | 326 | VFQVVESTRPGKKVW | 20 |
| 53 | 336 | GKKVWLGETSSAYGG | 20 |
| 54 | 361 | AGFMWLDKLGLSARM | 20 |
| 55 | 366 | LDKLGLSARMGIEVV | 20 |
| 56 | 372 | SARMGIEVVMRQVFF | 20 |
| 57 | 374 | RMGIEVVMRQVFFGA | 20 |
| 58 | 390 | NYHLVDENFDPLPDY | 20 |
| 59 | 403 | DYWLSLLFKKLVGTK | 20 |
| 60 | 415 | GTKVLMASVQGSKRR | 20 |
| 61 | 416 | TKVLMASVQGSKRRK | 20 |
| 62 | 420 | MASVQGSKRRKLRVY | 20 |
| 63 | 428 | RRKLRVYLHCTNTDN | 20 |
| 64 | 449 | DLTLYAINLHNVTKY | 20 |
| 65 | 463 | YLRLPYPFSNKQVDK | 20 |
| 66 | 477 | KYLLRPLGPHGLLSK | 20 |
| 67 | 492 | SVQLNGLTLKMVDDQ | 20 |
| 68 | 497 | GLTLKMVDDQTLPPL | 20 |
| 69 | 499 | TLKMVDDQTLPPLME | 20 |
| 70 | 505 | DQTLPPLMEKPLRPG | 20 |
| 71 | 509 | PPLMEKPLRPGSSLG | 20 |
| 72 | 513 | EKPLRPGSSLGLPAF | 20 |
| 73 | 23 | PLSPGALPRPAQAQD | 18 |
| 74 | 50 | HLVSPSFLSVTIDAN | 18 |
| 75 | 108 | KESTFEERSYWQSQV | 18 |
| 76 | 186 | FGLNALLRTADLQWN | 18 |
| 77 | 190 | ALLRTADLQWNSSNA | 18 |
| 78 | 216 | YNISWELGNEPNSFL | 18 |
| 79 | 230 | LKKADIFINGSQLGE | 18 |
| 80 | 240 | SQLGEDFIQLHKLLR | 18 |
| 81 | 252 | LLRKSTFKNAKLYGP | 18 |
| 82 | 273 | RKTAKMLKSFLKAGG | 18 |
| 83 | 304 | TATREDFLNPDVLDI | 18 |
| 84 | 314 | DVLDIFISSVQKVFQ | 18 |
| 85 | 408 | LLFKKLVGTKVLMAS | 18 |
| 86 | 443 | PRYKEGDLTLYAINL | 18 |
| 87 | 448 | GDLTLYAINLHNVTK | 18 |
| 88 | 451 | TLYAINLHNVTKYLR | 18 |

TABLE 2 (Continued)

| | | | |
|---|---|---|---|
| 89 | 464 | L R L P Y P F S N K Q V D K Y | 18 |
| 90 | 482 | P L G P H G L L S K S V Q L N | 18 |
| 91 | 527 | F S Y S F F V I R N A K V A A | 18 |
| 92 | 40 | D L D F F T Q E P L H L V S P | 16 |
| 93 | 98 | K T D F L I F D P K K E S T F | 16 |
| 94 | 126 | I C K Y G S I P P D V E E K L | 16 |
| 95 | 157 | Q K K F K N S T Y S R S S V D | 16 |
| 96 | 162 | N S T Y S R S S V D V L Y T F | 16 |
| 97 | 173 | L Y T F A N C S G L D L I F G | 16 |
| 98 | 183 | D L I F G L N A L L R T A D L | 16 |
| 99 | 196 | D L Q W N S S N A Q L L L D Y | 16 |
| 100 | 207 | L L D Y C S S K G Y N I S W E | 16 |
| 101 | 213 | S K G Y N I S W E L G N E P N | 16 |
| 102 | 217 | N I S W E L G N E P N S F L K | 16 |
| 103 | 233 | A D I F I N G S Q L G E D F I | 16 |
| 104 | 243 | G E D F I Q L H K L L R K S T | 16 |
| 105 | 255 | K S T F K N A K L Y G P D V G | 16 |
| 106 | 261 | A K L Y G P D V G Q P R R K T | 16 |
| 107 | 296 | H H Y Y L N G R T A T R E D F | 16 |
| 108 | 307 | R E D F L N P D V L D I F I S | 16 |
| 109 | 316 | L D I F I S S V Q K V F Q V V | 16 |
| 110 | 345 | S S A Y G G G A P L L S D T F | 16 |
| 111 | 383 | Q V F F G A G N Y H L V D E N | 16 |
| 112 | 388 | A G N Y H L V D E N F D P L P | 16 |
| 113 | 401 | L P D Y W L S L L F K K L V G | 16 |
| 114 | 147 | Q E Q L L L R E H Y Q K K F K | 15 |
| 115 | 249 | L H K L L R K S T F K N A K L | 15 |
| 116 | 6 | K P A L P P P L M L L L L G P | 14 |
| 117 | 11 | P P L M L L L L G P L G P L S | 14 |
| 118 | 12 | P L M L L L L G P L G P L S P | 14 |
| 119 | 13 | L M L L L L G P L G P L S P G | 14 |
| 120 | 14 | M L L L L G P L G P L S P G A | 14 |
| 121 | 15 | L L L L G P L G P L S P G A L | 14 |
| 122 | 26 | P G A L P R P A Q A Q D V V D | 14 |
| 123 | 36 | Q D V V D L D F F T Q E P L H | 14 |
| 124 | 48 | P L H L V S P S F L S V T I D | 14 |
| 125 | 49 | L H L V S P S F L S V T I D A | 14 |
| 126 | 54 | P S F L S V T I D A N L A T D | 14 |
| 127 | 71 | F L I L L G S P K L R T L A R | 14 |
| 128 | 72 | L I L L G S P K L R T L A R G | 14 |
| 129 | 80 | L R T L A R G L S P A Y L R F | 14 |
| 130 | 84 | A R G L S P A Y L R F G G T K | 14 |
| 131 | 89 | P A Y L R F G G T K T D F L I | 14 |
| 132 | 100 | D F L I F D P K K E S T F E E | 14 |
| 133 | 119 | Q S Q V N Q D I C K Y G S I P | 14 |
| 134 | 123 | N Q D I C K Y G S I P P D V E | 14 |
| 135 | 137 | E E K L R L E W P Y Q E Q L L | 14 |
| 136 | 149 | Q L L L R E H Y Q K K F K N S | 14 |

TABLE 2 (Continued)

| | | | |
|---|---|---|---|
| 137 | 169 | SVDVLYTFANCSGLD | 14 |
| 138 | 182 | LDLIFGLNALLRTAD | 14 |
| 139 | 204 | AQLLLDYCSSKGYNI | 14 |
| 140 | 205 | QLLLDYCSSKGYNIS | 14 |
| 141 | 215 | GYNISWELGNEPNSF | 14 |
| 142 | 232 | KADIFINGSQLGEDF | 14 |
| 143 | 239 | GSQLGEDFIQLHKLL | 14 |
| 144 | 244 | EDFIQLHKLLRKSTF | 14 |
| 145 | 250 | HKLLRKSTFKNAKLY | 14 |
| 146 | 276 | AKMLKSFLKAGGEVI | 14 |
| 147 | 286 | GGEVIDSVTWHHYYL | 14 |
| 148 | 287 | GEVIDSVTWHHYYLN | 14 |
| 149 | 290 | IDSVTWHHYYLNGRT | 14 |
| 150 | 308 | EDFLNPDVLDIFISS | 14 |
| 151 | 315 | VLDIFISSVQKVFQV | 14 |
| 152 | 323 | VQKVFQVVESTRPGK | 14 |
| 153 | 327 | FQVVESTRPGKKVWL | 14 |
| 154 | 338 | KVWLGETSSAYGGGA | 14 |
| 155 | 351 | GAPLLSDTFAAGFMW | 14 |
| 156 | 363 | FMWLDKLGLSARMGI | 14 |
| 157 | 377 | IEVVMRQVFFGAGNY | 14 |
| 158 | 378 | EVVMRQVFFGAGNYH | 14 |
| 159 | 398 | FDPLPDYWLSLLFKK | 14 |
| 160 | 410 | FKKLVGTKVLMASVQ | 14 |
| 161 | 417 | KVLMASVQGSKRRKL | 14 |
| 162 | 430 | KLRVYLHCTNTDNPR | 14 |
| 163 | 432 | RVYLHCTNTDNPRYK | 14 |
| 164 | 454 | AINLHNVTKYLRLPY | 14 |
| 165 | 457 | LHNVTKYLRLPYPFS | 14 |
| 166 | 461 | TKYLRLPYPFSNKQV | 14 |
| 167 | 472 | NKQVDKYLLRPLGPH | 14 |
| 168 | 480 | LRPLGPHGLLSKSVQ | 14 |
| 169 | 486 | HGLLSKSVQLNGLTL | 14 |
| 170 | 490 | SKSVQLNGLTLKMVD | 14 |
| 171 | 500 | LKMVDDQTLPPLMEK | 14 |
| 172 | 519 | GSSLGLPAFSYSFFV | 14 |
| 173 | 521 | SLGLPAFSYSFFVIR | 14 |
| 174 | 2 | LLRSKPALPPPLMLL | 12 |
| 175 | 3 | LRSKPALPPPLMLLL | 12 |
| 176 | 7 | PALPPPLMLLLLGPL | 12 |
| 177 | 17 | LLGPLGPLSPGALPR | 12 |
| 178 | 22 | GPLSPGALPRPAQAQ | 12 |
| 179 | 27 | GALPRPAQAQDVVDL | 12 |
| 180 | 28 | ALPRPAQAQDVVDLD | 12 |
| 181 | 34 | QAQDVVDLDFFTQEP | 12 |
| 182 | 37 | DVVDLDFFTQEPLHL | 12 |
| 183 | 42 | DFFTQEPLHLVSPSF | 12 |
| 184 | 45 | TQEPLHLVSPSFLSV | 12 |

TABLE 2 (Continued)

| | | | |
|---|---|---|---|
| 185 | 47 | E P L H L V S P S F L S V T I | 12 |
| 186 | 52 | V S P S F L S V T I D A N L A | 12 |
| 187 | 55 | S F L S V T I D A N L A T D P | 12 |
| 188 | 59 | V T I D A N L A T D P R F L I | 12 |
| 189 | 66 | A T D P R F L I L L G S P K L | 12 |
| 190 | 74 | L L G S P K L R T L A R G L S | 12 |
| 191 | 81 | R T L A R G L S P A Y L R F G | 12 |
| 192 | 86 | G L S P A Y L R F G G T K T D | 12 |
| 193 | 96 | G T K T D F L I F D P K K E S | 12 |
| 194 | 97 | T K T D F L I F D P K K E S T | 12 |
| 195 | 103 | I F D P K K E S T F E E R S Y | 12 |
| 196 | 107 | K K E S T F E E R S Y W Q S Q | 12 |
| 197 | 111 | T F E E R S Y W Q S Q V N Q D | 12 |
| 198 | 112 | F E E R S Y W Q S Q V N Q D I | 12 |
| 199 | 113 | E E R S Y W Q S Q V N Q D I C | 12 |
| 200 | 116 | S Y W Q S Q V N Q D I C K Y G | 12 |
| 201 | 120 | S Q V N Q D I C K Y G S I P P | 12 |
| 202 | 131 | S I P P D V E E K L R L E W P | 12 |
| 203 | 136 | V E E K L R L E W P Y Q E Q L | 12 |
| 204 | 145 | P Y Q E Q L L L R E H Y Q K K | 12 |
| 205 | 146 | Y Q E Q L L L R E H Y Q K K F | 12 |
| 206 | 154 | E H Y Q K K F K N S T Y S R S | 12 |
| 207 | 158 | K K F K N S T Y S R S S V D V | 12 |
| 208 | 159 | K F K N S T Y S R S S V D V L | 12 |
| 209 | 164 | T Y S R S S V D V L Y T F A N | 12 |
| 210 | 166 | S R S S V D V L Y T F A N C S | 12 |
| 211 | 177 | A N C S G L D L I F G L N A L | 12 |
| 212 | 178 | N C S G L D L I F G L N A L L | 12 |
| 213 | 180 | S G L D L I F G L N A L L R T | 12 |
| 214 | 184 | L I F G L N A L L R T A D L Q | 12 |
| 215 | 191 | L L R T A D L Q W N S S N A Q | 12 |
| 216 | 192 | L R T A D L Q W N S S N A Q L | 12 |
| 217 | 193 | R T A D L Q W N S S N A Q L L | 12 |
| 218 | 195 | A D L Q W N S S N A Q L L L D | 12 |
| 219 | 197 | L Q W N S S N A Q L L L D Y C | 12 |
| 220 | 201 | S S N A Q L L L D Y C S S K G | 12 |
| 221 | 202 | S N A Q L L L D Y C S S K G Y | 12 |
| 222 | 211 | C S S K G Y N I S W E L G N E | 12 |
| 223 | 220 | W E L G N E P N S F L K K A D | 12 |
| 224 | 224 | N E P N S F L K K A D I F I N | 12 |
| 225 | 229 | F L K K A D I F I N G S Q L G | 12 |
| 226 | 231 | K K A D I F I N G S Q L G E D | 12 |
| 227 | 236 | F I N G S Q L G E D F I Q L H | 12 |
| 228 | 238 | N G S Q L G E D F I Q L H K L | 12 |
| 229 | 241 | Q L G E D F I Q L H K L L R K | 12 |
| 230 | 242 | L G E D F I Q L H K L L R K S | 12 |
| 231 | 257 | T F K N A K L Y G P D V G Q P | 12 |
| 232 | 262 | K L Y G P D V G Q P R R K T A | 12 |

TABLE 2 (Continued)

| 233 | 264 | YGPDVGQPRRKTAKM | 12 |
|---|---|---|---|
| 234 | 270 | QPRRKTAKMLKSFLK | 12 |
| 235 | 282 | FLKAGGEVIDSVTWH | 12 |
| 236 | 283 | LKAGGEVIDSVTWHH | 12 |
| 237 | 284 | KAGGEVIDSVTWHHY | 12 |
| 238 | 289 | VIDSVTWHHYYLNGR | 12 |
| 239 | 293 | VTWHHYYLNGRTATR | 12 |
| 240 | 294 | TWHHYYLNGRTATRE | 12 |
| 241 | 299 | YLNGRTATREDFLNP | 12 |
| 242 | 305 | ATREDFLNPDVLDIF | 12 |
| 243 | 309 | DFLNPDVLDIFISSV | 12 |
| 244 | 310 | FLNPDVLDIFISSVQ | 12 |
| 245 | 311 | LNPDVLDIFISSVQK | 12 |
| 246 | 321 | SSVQKVFQVVESTRP | 12 |
| 247 | 325 | KVFQVVESTRPGKKV | 12 |
| 248 | 333 | TRPGKKVWLGETSSA | 12 |
| 249 | 335 | PGKKVWLGETSSAYG | 12 |
| 250 | 341 | LGETSSAYGGGAPLL | 12 |
| 251 | 348 | YGGGAPLLSDTFAAG | 12 |
| 252 | 349 | GGGAPLLSDTFAAGF | 12 |
| 253 | 350 | GGAPLLSDTFAAGFM | 12 |
| 254 | 353 | PLLSDTFAAGFMWLD | 12 |
| 255 | 355 | LSDTFAAGFMWLDKL | 12 |
| 256 | 357 | DTFAAGFMWLDKLGL | 12 |
| 257 | 364 | MWLDKLGLSARMGIE | 12 |
| 258 | 373 | ARMGIEVVMRQVFFG | 12 |
| 259 | 379 | VVMRQVFFGAGNYHL | 12 |
| 260 | 389 | GNYHLVDENFDPLPD | 12 |
| 261 | 397 | NFDPLPDYWLSLLFK | 12 |
| 262 | 400 | PLPDYWLSLLFKKLV | 12 |
| 263 | 412 | KLVGTKVLMASVQGS | 12 |
| 264 | 413 | LVGTKVLMASVQGSK | 12 |
| 265 | 427 | KRRKLRVYLHCTNTD | 12 |
| 266 | 429 | RKLRVYLHCTNTDNP | 12 |
| 267 | 435 | LHCTNTDNPRYKEGD | 12 |
| 268 | 441 | DNPRYKEGDLTLYAI | 12 |
| 269 | 444 | RYKEGDLTLYAINLH | 12 |
| 270 | 446 | KEGDLTLYAINLHNV | 12 |
| 271 | 453 | YAINLHNVTKYLRLP | 12 |
| 272 | 466 | LPYPFSNKQVDKYLL | 12 |
| 273 | 469 | PFSNKQVDKYLLRPL | 12 |
| 274 | 473 | KQVDKYLLRPLGPHG | 12 |
| 275 | 478 | YLLRPLGPHGLLSKS | 12 |
| 276 | 483 | LGPHGLLSKSVQLNG | 12 |
| 277 | 484 | GPHGLLSKSVQLNGL | 12 |
| 278 | 487 | GLLSKSVQLNGLTLK | 12 |
| 279 | 488 | LLSKSVQLNGLTLKM | 12 |
| 280 | 489 | LSKSVQLNGLTLKMV | 12 |

TABLE 2 (Continued)

| | | | |
|---|---|---|---|
| 281 | 491 | K S V Q L N G L T L K M V D D | 12 |
| 282 | 498 | L T L K M V D D Q T L P P L M | 12 |
| 283 | 510 | P L M E K P L R P G S S L G L | 12 |
| 284 | 520 | S S L G L P A F S Y S F F V I | 12 |
| 285 | 522 | L G L P A F S Y S F F V I R N | 12 |
| 286 | 525 | P A F S Y S F F V I R N A K V | 12 |
| 287 | 109 | E S T F E E R S Y W Q S Q V N | 11 |
| 288 | 153 | R E H Y Q K K F K N S T Y S R | 11 |
| 289 | 226 | P N S F L K K A D I F I N G S | 11 |
| 290 | 362 | G F M W L D K L G L S A R M G | 11 |
| 291 | 529 | Y S F F V I R N A K V A A C I | 11 |
| 292 | 114 | E R S Y W Q S Q V N Q D I C K | 10 |
| 293 | 143 | E W P Y Q E Q L L L R E H Y Q | 10 |
| 294 | 292 | S V T W H H Y Y L N G R T A T | 10 |
| 295 | 356 | S D T F A A G F M W L D K L G | 10 |
| 296 | 442 | N P R Y K E G D L T L Y A I N | 10 |
| 297 | 465 | R L P Y P F S N K Q V D K Y L | 10 |
| 298 | 524 | L P A F S Y S F F V I R N A K | 10 |
| 299 | 133 | P P D V E E K L R L E W P Y Q | 9 |
| 300 | 368 | K L G L S A R M G I E V V M R | 9 |
| 301 | 405 | W L S L L F K K L V G T K V L | 9 |
| 302 | 406 | L S L L F K K L V G T K V L M | 9 |
| 303 | 411 | K K L V G T K V L M A S V Q G | 9 |
| 304 | 485 | P H G L L S K S V Q L N G L T | 9 |
| 305 | 495 | L N G L T L K M V D D Q T L P | 9 |
| 306 | 21 | L G P L S P G A L P R P A Q A | 8 |
| 307 | 58 | S V T I D A N L A T D P R F L | 8 |
| 308 | 70 | R F L I L L G S P K L R T L A | 8 |
| 309 | 188 | L N A L L R T A D L Q W N S S | 8 |
| 310 | 234 | D I F I N G S Q L G E D F I Q | 8 |
| 311 | 260 | N A K L Y G P D V G Q P R R K | 8 |
| 312 | 275 | T A K M L K S F L K A G G E V | 8 |
| 313 | 280 | K S F L K A G G E V I D S V T | 8 |
| 314 | 352 | A P L L S D T F A A G F M W L | 8 |
| 315 | 381 | M R Q V F F G A G N Y H L V D | 8 |
| 316 | 391 | Y H L V D E N F D P L P D Y W | 8 |
| 317 | 447 | E G D L T L Y A I N L H N V T | 8 |
| 318 | 452 | L Y A I N L H N V T K Y L R L | 8 |
| 319 | 476 | D K Y L L R P L G P H G L L S | 8 |
| 320 | 73 | I L L G S P K L R T L A R G L | 7 |
| 321 | 155 | H Y Q K K F K N S T Y S R S S | 7 |
| 322 | 161 | K N S T Y S R S S V D V L Y T | 7 |
| 323 | 248 | Q L H K L L R K S T F K N A K | 7 |
| 324 | 267 | D V G Q P R R K T A K M L K S | 7 |
| 325 | 424 | Q G S K R R K L R V Y L H C T | 7 |
| 326 | 4 | R S K P A L P P P L M L L L L | 6 |
| 327 | 5 | S K P A L P P P L M L L L L G | 6 |
| 328 | 9 | L P P P L M L L L L G P L G P | 6 |

TABLE 2 (Continued)

| | | | |
|---|---|---|---|
| 329 | 24 | LSPGALPRPAQAQDV | 6 |
| 330 | 29 | LPRPAQAQDVVDLDF | 6 |
| 331 | 30 | PRPAQAQDVVDLDFF | 6 |
| 332 | 31 | RPAQAQDVVDLDFFT | 6 |
| 333 | 32 | PAQAQDVVDLDFFTQ | 6 |
| 334 | 33 | AQAQDVVDLDFFTQE | 6 |
| 335 | 43 | FFTQEPLHLVSPSFL | 6 |
| 336 | 44 | FTQEPLHLVSPSFLS | 6 |
| 337 | 51 | LVSPSFLSVTIDANL | 6 |
| 338 | 57 | LSVTIDANLATDPRF | 6 |
| 339 | 60 | TIDANLATDPRFLIL | 6 |
| 340 | 61 | IDANLATDPRFLILL | 6 |
| 341 | 63 | ANLATDPRFLILLGS | 6 |
| 342 | 65 | LATDPRFLILLGSPK | 6 |
| 343 | 67 | TDPRFLILLGSPKLR | 6 |
| 344 | 76 | GSPKLRTLARGLSPA | 6 |
| 345 | 78 | PKLRTLARGLSPAYL | 6 |
| 346 | 85 | RGLSPAYLRFGGTKT | 6 |
| 347 | 94 | FGGTKTDFLIFDPKK | 6 |
| 348 | 95 | GGTKTDFLIFDPKKE | 6 |
| 349 | 105 | DPKKESTFEERSYWQ | 6 |
| 350 | 106 | PKKESTFEERSYWQS | 6 |
| 351 | 110 | STFEERSYWQSQVNQ | 6 |
| 352 | 117 | YWQSQVNQDICKYGS | 6 |
| 353 | 121 | QVNQDICKYGSIPPD | 6 |
| 354 | 125 | DICKYGSIPPDVEEK | 6 |
| 355 | 128 | KYGSIPPDVEEKLRL | 6 |
| 356 | 130 | GSIPPDVEEKLRLEW | 6 |
| 357 | 132 | IPPDVEEKLRLEWPY | 6 |
| 358 | 134 | PDVEEKLRLEWPYQE | 6 |
| 359 | 138 | EKLRLEWPYQEQLLL | 6 |
| 360 | 140 | LRLEWPYQEQLLLRE | 6 |
| 361 | 142 | LEWPYQEQLLLREHY | 6 |
| 362 | 144 | WPYQEQLLLREHYQK | 6 |
| 363 | 150 | LLLREHYQKKFKNST | 6 |
| 364 | 151 | LLREHYQKKFKNSTY | 6 |
| 365 | 156 | YQKKFKNSTYSRSSV | 6 |
| 366 | 160 | FKNSTYSRSSVDVLY | 6 |
| 367 | 165 | YSRSSVDVLYTFANC | 6 |
| 368 | 172 | VLYTFANCSGLDLIF | 6 |
| 369 | 174 | YTFANCSGLDLIFGL | 6 |
| 370 | 176 | FANCSGLDLIFGLNA | 6 |
| 371 | 198 | QWNSSNAQLLLDYCS | 6 |
| 372 | 200 | NSSNAQLLLDYCSSK | 6 |
| 373 | 206 | LLLDYCSSKGYNISW | 6 |
| 374 | 209 | DYCSSKGYNISWELG | 6 |
| 375 | 212 | SSKGYNISWELGNEP | 6 |
| 376 | 221 | ELGNEPNSFLKKADI | 6 |

TABLE 2 (Continued)

| | | | |
|---|---|---|---|
| 377 | 222 | L G N E P N S F L K K A D I F | 6 |
| 378 | 223 | G N E P N S F L K K A D I F I | 6 |
| 379 | 228 | S F L K K A D I F I N G S Q L | 6 |
| 380 | 237 | I N G S Q L G E D F I Q L H K | 6 |
| 381 | 247 | I Q L H K L L R K S T F K N A | 6 |
| 382 | 251 | K L L R K S T F K N A K L Y G | 6 |
| 383 | 259 | K N A K L Y G P D V G Q P R R | 6 |
| 384 | 263 | L Y G P D V G Q P R R K T A K | 6 |
| 385 | 269 | G Q P R R K T A K M L K S F L | 6 |
| 386 | 272 | R R K T A K M L K S F L K A G | 6 |
| 387 | 277 | K M L K S F L K A G G E V I D | 6 |
| 388 | 281 | S F L K A G G E V I D S V T W | 6 |
| 389 | 285 | A G G E V I D S V T W H H Y Y | 6 |
| 390 | 288 | E V I D S V T W H H Y Y L N G | 6 |
| 391 | 298 | Y Y L N G R T A T R E D F L N | 6 |
| 392 | 300 | L N G R T A T R E D F L N P D | 6 |
| 393 | 302 | G R T A T R E D F L N P D V L | 6 |
| 394 | 303 | R T A T R E D F L N P D V L D | 6 |
| 395 | 318 | I F I S S V Q K V F Q V V E S | 6 |
| 396 | 322 | S V Q K V F Q V V E S T R P G | 6 |
| 397 | 330 | V E S T R P G K K V W L G E T | 6 |
| 398 | 334 | R P G K K V W L G E T S S A Y | 6 |
| 399 | 343 | E T S S A Y G G G A P L L S D | 6 |
| 400 | 344 | T S S A Y G G G A P L L S D T | 6 |
| 401 | 346 | S A Y G G G A P L L S D T F A | 6 |
| 402 | 347 | A Y G G G A P L L S D T F A A | 6 |
| 403 | 354 | L L S D T F A A G F M W L D K | 6 |
| 404 | 358 | T F A A G F M W L D K L G L S | 6 |
| 405 | 365 | W L D K L G L S A R M G I E V | 6 |
| 406 | 367 | D K L G L S A R M G I E V V M | 6 |
| 407 | 369 | L G L S A R M G I E V V M R Q | 6 |
| 408 | 370 | G L S A R M G I E V V M R Q V | 6 |
| 409 | 371 | L S A R M G I E V V M R Q V F | 6 |
| 410 | 375 | M G I E V V M R Q V F F G A G | 6 |
| 411 | 380 | V M R Q V F F G A G N Y H L V | 6 |
| 412 | 384 | V F F G A G N Y H L V D E N F | 6 |
| 413 | 386 | F G A G N Y H L V D E N F D P | 6 |
| 414 | 387 | G A G N Y H L V D E N F D P L | 6 |
| 415 | 392 | H L V D E N F D P L P D Y W L | 6 |
| 416 | 393 | L V D E N F D P L P D Y W L S | 6 |
| 417 | 396 | E N F D P L P D Y W L S L L F | 6 |
| 418 | 399 | D P L P D Y W L S L L F K K L | 6 |
| 419 | 404 | Y W L S L L F K K L V G T K V | 6 |
| 420 | 409 | L F K K L V G T K V L M A S V | 6 |
| 421 | 414 | V G T K V L M A S V Q G S K R | 6 |
| 422 | 418 | V L M A S V Q G S K R R K L R | 6 |
| 423 | 419 | L M A S V Q G S K R R K L R V | 6 |
| 424 | 425 | G S K R R K L R V Y L H C T N | 6 |

TABLE 2 (Continued)

| | | | |
|---|---|---|---|
| 425 | 434 | YLHCTNTDNPRYKEG | 6 |
| 426 | 436 | HCTNTDNPRYKEGDL | 6 |
| 427 | 439 | NTDNPRYKEGDLTLY | 6 |
| 428 | 445 | YKEGDLTLYAINLHN | 6 |
| 429 | 455 | INLHNVTKYLRLPYP | 6 |
| 430 | 458 | HNVTKYLRLPYPFSN | 6 |
| 431 | 462 | KYLRLPYPFSNKQVD | 6 |
| 432 | 468 | YPFSNKQVDKYLLRP | 6 |
| 433 | 470 | FSNKQVDKYLLRPLG | 6 |
| 434 | 474 | QVDKYLLRPLGPHGL | 6 |
| 435 | 479 | LLRPLGPHGLLSKSV | 6 |
| 436 | 481 | RPLGPHGLLSKSVQL | 6 |
| 437 | 494 | QLNGLTLKMVDDQTL | 6 |
| 438 | 496 | NGLTLKMVDDQTLPP | 6 |
| 439 | 501 | KMVDDQTLPPLMEKP | 6 |
| 440 | 502 | MVDDQTLPPLMEKPL | 6 |
| 441 | 503 | VDDQTLPPLMEKPLR | 6 |
| 442 | 507 | TLPPLMEKPLRPGSS | 6 |
| 443 | 512 | MEKPLRPGSSLGLPA | 6 |
| 444 | 515 | PLRPGSSLGLPAFSY | 6 |
| 445 | 516 | LRPGSSLGLPAFSYS | 6 |
| 446 | 517 | RPGSSLGLPAFSYSF | 6 |
| 447 | 518 | PGSSLGLPAFSYSFF | 6 |
| 448 | 523 | GLPAFSYSFFVIRNA | 6 |
| 449 | 101 | FLIFDPKKESTFEER | 5 |
| 450 | 467 | PYPFSNKQVDKYLLR | 5 |
| 451 | 475 | VDKYLLRPLGPHGLL | 5 |
| 452 | 297 | HYYLNGRTATREDFL | 3 |
| 453 | 376 | GIEVVMRQVFFGAGN | 3 |
| 454 | 508 | LPPLMEKPLRPGSSL | 3 |
| 455 | 25 | SPGALPRPAQAQDVV | 1 |
| 456 | 64 | NLATDPRFLILLGSP | 1 |
| 457 | 79 | KLRTLARGLSPAYLR | 1 |
| 458 | 87 | LSPAYLRFGGTKTDF | 1 |
| 459 | 92 | LRFGGTKTDFLIFDP | 1 |
| 460 | 102 | LIFDPKKESTFEERS | 1 |
| 461 | 152 | LREHYQKKFKNSTYS | 1 |
| 462 | 187 | GLNALLRTADLQWNS | 1 |
| 463 | 208 | LDYCSSKGYNISWEL | 1 |
| 464 | 245 | DFIQLHKLLRKSTFK | 1 |
| 465 | 266 | PDVGQPRRKTAKMLK | 1 |
| 466 | 268 | VGQPRRKTAKMLKSF | 1 |
| 467 | 274 | KTAKMLKSFLKAGGE | 1 |
| 468 | 278 | MLKSFLKAGGEVIDS | 1 |
| 469 | 301 | NGRTATREDFLNPDV | 1 |
| 470 | 319 | FISSVQKVFQVVEST | 1 |
| 471 | 328 | QVVESTRPGKKVWLG | 1 |
| 472 | 421 | ASVQGSKRRKLRVYL | 1 |

TABLE 2 (Continued)

| 473 | 422 | S V Q G S K R R K L R V Y L H | 1 |
|---|---|---|---|
| 474 | 440 | T D N P R Y K E G D L T L Y A | 1 |
| 475 | 511 | L M E K P L R P G S S L G L P | 1 |

SEQUENCE LISTING

<160> NUMBER OF SEQ ID NOS: 985

<210> SEQ ID NO 1
<211> LENGTH: 9
<212> TYPE: PRT
<213> ORGANISM: Homo sapiens

<400> SEQUENCE: 1

Leu Leu Leu Gly Pro Leu Gly Pro Leu
1               5

<210> SEQ ID NO 2

```
<211> LENGTH: 9
<212> TYPE: PRT
<213> ORGANISM: Homo sapiens

<400> SEQUENCE: 2

Ala Leu Pro Pro Pro Leu Met Leu Leu
1               5

<210> SEQ ID NO 3
<211> LENGTH: 9
<212> TYPE: PRT
<213> ORGANISM: Homo sapiens

<400> SEQUENCE: 3

Asp Leu Ile Phe Gly Leu Asn Ala Leu
1               5

<210> SEQ ID NO 4
<211> LENGTH: 9
<212> TYPE: PRT
<213> ORGANISM: Homo sapiens

<400> SEQUENCE: 4

Val Leu Asp Ile Phe Ile Ser Ser Val
1               5

<210> SEQ ID NO 5
<211> LENGTH: 9
<212> TYPE: PRT
<213> ORGANISM: Homo sapiens

<400> SEQUENCE: 5

Leu Met Leu Leu Leu Leu Gly Pro Leu
1               5

<210> SEQ ID NO 6
<211> LENGTH: 9
<212> TYPE: PRT
<213> ORGANISM: Homo sapiens

<400> SEQUENCE: 6

Leu Ile Leu Leu Gly Ser Pro Lys Leu
1               5

<210> SEQ ID NO 7
<211> LENGTH: 9
<212> TYPE: PRT
<213> ORGANISM: Homo sapiens

<400> SEQUENCE: 7

Phe Leu Asn Pro Asp Val Leu Asp Ile
1               5

<210> SEQ ID NO 8
<211> LENGTH: 9
<212> TYPE: PRT
<213> ORGANISM: Homo sapiens

<400> SEQUENCE: 8

Leu Ile Phe Gly Leu Asn Ala Leu Leu
1               5

<210> SEQ ID NO 9
<211> LENGTH: 9
<212> TYPE: PRT
```

```
<213> ORGANISM: Homo sapiens

<400> SEQUENCE: 9

Gly Leu Leu Ser Lys Ser Val Gln Leu
1               5

<210> SEQ ID NO 10
<211> LENGTH: 9
<212> TYPE: PRT
<213> ORGANISM: Homo sapiens

<400> SEQUENCE: 10

Leu Leu Phe Lys Lys Leu Val Gly Thr
1               5

<210> SEQ ID NO 11
<211> LENGTH: 9
<212> TYPE: PRT
<213> ORGANISM: Homo sapiens

<400> SEQUENCE: 11

Met Leu Leu Arg Ser Lys Pro Ala Leu
1               5

<210> SEQ ID NO 12
<211> LENGTH: 9
<212> TYPE: PRT
<213> ORGANISM: Homo sapiens

<400> SEQUENCE: 12

Phe Thr Gln Glu Pro Leu His Leu Val
1               5

<210> SEQ ID NO 13
<211> LENGTH: 9
<212> TYPE: PRT
<213> ORGANISM: Homo sapiens

<400> SEQUENCE: 13

Lys Leu Arg Thr Leu Ala Arg Gly Leu
1               5

<210> SEQ ID NO 14
<211> LENGTH: 9
<212> TYPE: PRT
<213> ORGANISM: Homo sapiens

<400> SEQUENCE: 14

Gly Leu Asn Ala Leu Leu Arg Thr Ala
1               5

<210> SEQ ID NO 15
<211> LENGTH: 9
<212> TYPE: PRT
<213> ORGANISM: Homo sapiens

<400> SEQUENCE: 15

Ser Ala Tyr Gly Gly Gly Ala Pro Leu
1               5

<210> SEQ ID NO 16
<211> LENGTH: 9
<212> TYPE: PRT
<213> ORGANISM: Homo sapiens
```

```
<400> SEQUENCE: 16

Gln Leu Asn Gly Leu Thr Leu Lys Met
1               5

<210> SEQ ID NO 17
<211> LENGTH: 9
<212> TYPE: PRT
<213> ORGANISM: Homo sapiens

<400> SEQUENCE: 17

Asn Leu Ala Thr Asp Pro Arg Phe Leu
1               5

<210> SEQ ID NO 18
<211> LENGTH: 9
<212> TYPE: PRT
<213> ORGANISM: Homo sapiens

<400> SEQUENCE: 18

Thr Leu Ala Arg Gly Leu Ser Pro Ala
1               5

<210> SEQ ID NO 19
<211> LENGTH: 9
<212> TYPE: PRT
<213> ORGANISM: Homo sapiens

<400> SEQUENCE: 19

Gln Leu Gly Glu Asp Phe Ile Gln Leu
1               5

<210> SEQ ID NO 20
<211> LENGTH: 9
<212> TYPE: PRT
<213> ORGANISM: Homo sapiens

<400> SEQUENCE: 20

Phe Met Trp Leu Asp Lys Leu Gly Leu
1               5

<210> SEQ ID NO 21
<211> LENGTH: 9
<212> TYPE: PRT
<213> ORGANISM: Homo sapiens

<400> SEQUENCE: 21

Ser Ala Arg Met Gly Ile Glu Val Val
1               5

<210> SEQ ID NO 22
<211> LENGTH: 9
<212> TYPE: PRT
<213> ORGANISM: Homo sapiens

<400> SEQUENCE: 22

Pro Leu Pro Asp Tyr Trp Leu Ser Leu
1               5

<210> SEQ ID NO 23
<211> LENGTH: 9
<212> TYPE: PRT
<213> ORGANISM: Homo sapiens

<400> SEQUENCE: 23
```

```
Trp Leu Ser Leu Leu Phe Lys Lys Leu
1               5
```

<210> SEQ ID NO 24
<211> LENGTH: 9
<212> TYPE: PRT
<213> ORGANISM: Homo sapiens
<400> SEQUENCE: 24

```
Leu Val Ser Pro Ser Phe Leu Ser Val
1               5
```

<210> SEQ ID NO 25
<211> LENGTH: 9
<212> TYPE: PRT
<213> ORGANISM: Homo sapiens
<400> SEQUENCE: 25

```
Leu Gly Ser Pro Lys Leu Arg Thr Leu
1               5
```

<210> SEQ ID NO 26
<211> LENGTH: 9
<212> TYPE: PRT
<213> ORGANISM: Homo sapiens
<400> SEQUENCE: 26

```
Ser Gly Leu Asp Leu Ile Phe Gly Leu
1               5
```

<210> SEQ ID NO 27
<211> LENGTH: 9
<212> TYPE: PRT
<213> ORGANISM: Homo sapiens
<400> SEQUENCE: 27

```
Tyr Leu Asn Gly Arg Thr Ala Thr Arg
1               5
```

<210> SEQ ID NO 28
<211> LENGTH: 9
<212> TYPE: PRT
<213> ORGANISM: Homo sapiens
<400> SEQUENCE: 28

```
Lys Leu Arg Val Tyr Leu His Cys Thr
1               5
```

<210> SEQ ID NO 29
<211> LENGTH: 9
<212> TYPE: PRT
<213> ORGANISM: Homo sapiens
<400> SEQUENCE: 29

```
Asn Leu His Asn Val Thr Lys Tyr Leu
1               5
```

<210> SEQ ID NO 30
<211> LENGTH: 9
<212> TYPE: PRT
<213> ORGANISM: Homo sapiens
<400> SEQUENCE: 30

```
Ala Gln Ala Gln Asp Val Val Asp Leu
1               5
```

<210> SEQ ID NO 31
<211> LENGTH: 9
<212> TYPE: PRT
<213> ORGANISM: Homo sapiens

<400> SEQUENCE: 31

Asn Ala Leu Leu Arg Thr Ala Asp Leu
1               5

<210> SEQ ID NO 32
<211> LENGTH: 9
<212> TYPE: PRT
<213> ORGANISM: Homo sapiens

<400> SEQUENCE: 32

Phe Leu Lys Ala Gly Gly Glu Val Ile
1               5

<210> SEQ ID NO 33
<211> LENGTH: 9
<212> TYPE: PRT
<213> ORGANISM: Homo sapiens

<400> SEQUENCE: 33

Ala Gly Gly Glu Val Ile Asp Ser Val
1               5

<210> SEQ ID NO 34
<211> LENGTH: 9
<212> TYPE: PRT
<213> ORGANISM: Homo sapiens

<400> SEQUENCE: 34

Ile Phe Ile Ser Ser Val Gln Lys Val
1               5

<210> SEQ ID NO 35
<211> LENGTH: 9
<212> TYPE: PRT
<213> ORGANISM: Homo sapiens

<400> SEQUENCE: 35

Ala Thr Asp Pro Arg Phe Leu Ile Leu
1               5

<210> SEQ ID NO 36
<211> LENGTH: 9
<212> TYPE: PRT
<213> ORGANISM: Homo sapiens

<400> SEQUENCE: 36

Tyr Leu Arg Phe Gly Gly Thr Lys Thr
1               5

<210> SEQ ID NO 37
<211> LENGTH: 9
<212> TYPE: PRT
<213> ORGANISM: Homo sapiens

<400> SEQUENCE: 37

Ala Gly Phe Met Trp Leu Asp Lys Leu
1               5

```
<210> SEQ ID NO 38
<211> LENGTH: 9
<212> TYPE: PRT
<213> ORGANISM: Homo sapiens

<400> SEQUENCE: 38

Lys Leu Val Gly Thr Lys Val Leu Met
1               5

<210> SEQ ID NO 39
<211> LENGTH: 9
<212> TYPE: PRT
<213> ORGANISM: Homo sapiens

<400> SEQUENCE: 39

Gly Thr Lys Val Leu Met Ala Ser Val
1               5

<210> SEQ ID NO 40
<211> LENGTH: 9
<212> TYPE: PRT
<213> ORGANISM: Homo sapiens

<400> SEQUENCE: 40

Asp Leu Thr Leu Tyr Ala Ile Asn Leu
1               5

<210> SEQ ID NO 41
<211> LENGTH: 9
<212> TYPE: PRT
<213> ORGANISM: Homo sapiens

<400> SEQUENCE: 41

Leu Tyr Ala Ile Asn Leu His Asn Val
1               5

<210> SEQ ID NO 42
<211> LENGTH: 9
<212> TYPE: PRT
<213> ORGANISM: Homo sapiens

<400> SEQUENCE: 42

Tyr Leu Leu Arg Pro Leu Gly Pro His
1               5

<210> SEQ ID NO 43
<211> LENGTH: 9
<212> TYPE: PRT
<213> ORGANISM: Homo sapiens

<400> SEQUENCE: 43

Ser Val Gln Leu Asn Gly Leu Thr Leu
1               5

<210> SEQ ID NO 44
<211> LENGTH: 9
<212> TYPE: PRT
<213> ORGANISM: Homo sapiens

<400> SEQUENCE: 44

Leu Leu Leu Leu Gly Pro Leu Gly Pro
1               5

<210> SEQ ID NO 45
<211> LENGTH: 9
```

```
<212> TYPE: PRT
<213> ORGANISM: Homo sapiens

<400> SEQUENCE: 45

Leu Leu Gly Ser Pro Lys Leu Arg Thr
1               5

<210> SEQ ID NO 46
<211> LENGTH: 9
<212> TYPE: PRT
<213> ORGANISM: Homo sapiens

<400> SEQUENCE: 46

Ser Ile Pro Pro Asp Val Glu Glu Lys
1               5

<210> SEQ ID NO 47
<211> LENGTH: 9
<212> TYPE: PRT
<213> ORGANISM: Homo sapiens

<400> SEQUENCE: 47

Tyr Thr Phe Ala Asn Cys Ser Gly Leu
1               5

<210> SEQ ID NO 48
<211> LENGTH: 9
<212> TYPE: PRT
<213> ORGANISM: Homo sapiens

<400> SEQUENCE: 48

Leu Leu Leu Asp Tyr Cys Ser Ser Lys
1               5

<210> SEQ ID NO 49
<211> LENGTH: 9
<212> TYPE: PRT
<213> ORGANISM: Homo sapiens

<400> SEQUENCE: 49

Phe Leu Lys Lys Ala Asp Ile Phe Ile
1               5

<210> SEQ ID NO 50
<211> LENGTH: 9
<212> TYPE: PRT
<213> ORGANISM: Homo sapiens

<400> SEQUENCE: 50

Asp Ile Phe Ile Asn Gly Ser Gln Leu
1               5

<210> SEQ ID NO 51
<211> LENGTH: 9
<212> TYPE: PRT
<213> ORGANISM: Homo sapiens

<400> SEQUENCE: 51

Lys Leu Tyr Gly Pro Asp Val Gly Gln
1               5

<210> SEQ ID NO 52
<211> LENGTH: 9
<212> TYPE: PRT
<213> ORGANISM: Homo sapiens
```

```
<400> SEQUENCE: 52

Lys Met Leu Lys Ser Phe Leu Lys Ala
1               5

<210> SEQ ID NO 53
<211> LENGTH: 9
<212> TYPE: PRT
<213> ORGANISM: Homo sapiens

<400> SEQUENCE: 53

Trp Leu Asp Lys Leu Gly Leu Ser Ala
1               5

<210> SEQ ID NO 54
<211> LENGTH: 9
<212> TYPE: PRT
<213> ORGANISM: Homo sapiens

<400> SEQUENCE: 54

Gly Ile Glu Val Val Met Arg Gln Val
1               5

<210> SEQ ID NO 55
<211> LENGTH: 9
<212> TYPE: PRT
<213> ORGANISM: Homo sapiens

<400> SEQUENCE: 55

Leu Val Asp Glu Asn Phe Asp Pro Leu
1               5

<210> SEQ ID NO 56
<211> LENGTH: 9
<212> TYPE: PRT
<213> ORGANISM: Homo sapiens

<400> SEQUENCE: 56

Ser Lys Ser Val Gln Leu Asn Gly Leu
1               5

<210> SEQ ID NO 57
<211> LENGTH: 9
<212> TYPE: PRT
<213> ORGANISM: Homo sapiens

<400> SEQUENCE: 57

Pro Ala Leu Pro Pro Pro Leu Met Leu
1               5

<210> SEQ ID NO 58
<211> LENGTH: 9
<212> TYPE: PRT
<213> ORGANISM: Homo sapiens

<400> SEQUENCE: 58

Phe Ala Asn Cys Ser Gly Leu Asp Leu
1               5

<210> SEQ ID NO 59
<211> LENGTH: 9
<212> TYPE: PRT
<213> ORGANISM: Homo sapiens

<400> SEQUENCE: 59
```

```
Gln Leu His Lys Leu Leu Arg Lys Ser
1               5
```

<210> SEQ ID NO 60
<211> LENGTH: 9
<212> TYPE: PRT
<213> ORGANISM: Homo sapiens

<400> SEQUENCE: 60

```
Ser Ser Val Gln Lys Val Phe Gln Val
1               5
```

<210> SEQ ID NO 61
<211> LENGTH: 9
<212> TYPE: PRT
<213> ORGANISM: Homo sapiens

<400> SEQUENCE: 61

```
Ala Tyr Gly Gly Gly Ala Pro Leu Leu
1               5
```

<210> SEQ ID NO 62
<211> LENGTH: 9
<212> TYPE: PRT
<213> ORGANISM: Homo sapiens

<400> SEQUENCE: 62

```
Val Leu Met Ala Ser Val Gln Gly Ser
1               5
```

<210> SEQ ID NO 63
<211> LENGTH: 9
<212> TYPE: PRT
<213> ORGANISM: Homo sapiens

<400> SEQUENCE: 63

```
Leu Pro Pro Pro Leu Met Leu Leu Leu
1               5
```

<210> SEQ ID NO 64
<211> LENGTH: 9
<212> TYPE: PRT
<213> ORGANISM: Homo sapiens

<400> SEQUENCE: 64

```
Leu Leu Gly Pro Leu Gly Pro Leu Ser
1               5
```

<210> SEQ ID NO 65
<211> LENGTH: 9
<212> TYPE: PRT
<213> ORGANISM: Homo sapiens

<400> SEQUENCE: 65

```
Pro Leu Gly Pro Leu Ser Pro Gly Ala
1               5
```

<210> SEQ ID NO 66
<211> LENGTH: 9
<212> TYPE: PRT
<213> ORGANISM: Homo sapiens

<400> SEQUENCE: 66

```
Phe Leu Ser Val Thr Ile Asp Ala Asn
```

```
<210> SEQ ID NO 67
<211> LENGTH: 9
<212> TYPE: PRT
<213> ORGANISM: Homo sapiens

<400> SEQUENCE: 67

Thr Ile Asp Ala Asn Leu Ala Thr Asp
1               5

<210> SEQ ID NO 68
<211> LENGTH: 9
<212> TYPE: PRT
<213> ORGANISM: Homo sapiens

<400> SEQUENCE: 68

Leu Glu Trp Pro Tyr Gln Glu Gln Leu
1               5

<210> SEQ ID NO 69
<211> LENGTH: 9
<212> TYPE: PRT
<213> ORGANISM: Homo sapiens

<400> SEQUENCE: 69

Leu Leu Arg Glu His Tyr Gln Lys Lys
1               5

<210> SEQ ID NO 70
<211> LENGTH: 9
<212> TYPE: PRT
<213> ORGANISM: Homo sapiens

<400> SEQUENCE: 70

Tyr Ser Arg Ser Ser Val Asp Val Leu
1               5

<210> SEQ ID NO 71
<211> LENGTH: 9
<212> TYPE: PRT
<213> ORGANISM: Homo sapiens

<400> SEQUENCE: 71

Ala Asn Cys Ser Gly Leu Asp Leu Ile
1               5

<210> SEQ ID NO 72
<211> LENGTH: 9
<212> TYPE: PRT
<213> ORGANISM: Homo sapiens

<400> SEQUENCE: 72

Leu Gly Asn Glu Pro Asn Ser Phe Leu
1               5

<210> SEQ ID NO 73
<211> LENGTH: 9
<212> TYPE: PRT
<213> ORGANISM: Homo sapiens

<400> SEQUENCE: 73

Leu Leu Arg Lys Ser Thr Phe Lys Asn
1               5
```

<210> SEQ ID NO 74
<211> LENGTH: 9
<212> TYPE: PRT
<213> ORGANISM: Homo sapiens

<400> SEQUENCE: 74

Ser Phe Leu Lys Ala Gly Gly Glu Val
1               5

<210> SEQ ID NO 75
<211> LENGTH: 9
<212> TYPE: PRT
<213> ORGANISM: Homo sapiens

<400> SEQUENCE: 75

Ser Val Thr Trp His His Tyr Tyr Leu
1               5

<210> SEQ ID NO 76
<211> LENGTH: 9
<212> TYPE: PRT
<213> ORGANISM: Homo sapiens

<400> SEQUENCE: 76

Arg Thr Ala Thr Arg Glu Asp Phe Leu
1               5

<210> SEQ ID NO 77
<211> LENGTH: 9
<212> TYPE: PRT
<213> ORGANISM: Homo sapiens

<400> SEQUENCE: 77

Ser Val Gln Lys Val Phe Gln Val Val
1               5

<210> SEQ ID NO 78
<211> LENGTH: 9
<212> TYPE: PRT
<213> ORGANISM: Homo sapiens

<400> SEQUENCE: 78

Lys Val Phe Gln Val Val Glu Ser Thr
1               5

<210> SEQ ID NO 79
<211> LENGTH: 9
<212> TYPE: PRT
<213> ORGANISM: Homo sapiens

<400> SEQUENCE: 79

Pro Leu Leu Ser Asp Thr Phe Ala Ala
1               5

<210> SEQ ID NO 80
<211> LENGTH: 9
<212> TYPE: PRT
<213> ORGANISM: Homo sapiens

<400> SEQUENCE: 80

Leu Leu Ser Asp Thr Phe Ala Ala Gly
1               5

<210> SEQ ID NO 81

```
<211> LENGTH: 9
<212> TYPE: PRT
<213> ORGANISM: Homo sapiens

<400> SEQUENCE: 81

Leu Ser Ala Arg Met Gly Ile Glu Val
1               5

<210> SEQ ID NO 82
<211> LENGTH: 9
<212> TYPE: PRT
<213> ORGANISM: Homo sapiens

<400> SEQUENCE: 82

Phe Gly Ala Gly Asn Tyr His Leu Val
1               5

<210> SEQ ID NO 83
<211> LENGTH: 9
<212> TYPE: PRT
<213> ORGANISM: Homo sapiens

<400> SEQUENCE: 83

Lys Lys Leu Val Gly Thr Lys Val Leu
1               5

<210> SEQ ID NO 84
<211> LENGTH: 9
<212> TYPE: PRT
<213> ORGANISM: Homo sapiens

<400> SEQUENCE: 84

Leu Val Gly Thr Lys Val Leu Met Ala
1               5

<210> SEQ ID NO 85
<211> LENGTH: 9
<212> TYPE: PRT
<213> ORGANISM: Homo sapiens

<400> SEQUENCE: 85

Arg Tyr Lys Glu Gly Asp Leu Thr Leu
1               5

<210> SEQ ID NO 86
<211> LENGTH: 9
<212> TYPE: PRT
<213> ORGANISM: Homo sapiens

<400> SEQUENCE: 86

Leu Leu Arg Pro Leu Gly Pro His Gly
1               5

<210> SEQ ID NO 87
<211> LENGTH: 9
<212> TYPE: PRT
<213> ORGANISM: Homo sapiens

<400> SEQUENCE: 87

Leu Arg Pro Leu Gly Pro His Gly Leu
1               5

<210> SEQ ID NO 88
<211> LENGTH: 9
<212> TYPE: PRT
```

```
<213> ORGANISM: Homo sapiens

<400> SEQUENCE: 88

Leu Leu Ser Lys Ser Val Gln Leu Asn
1               5

<210> SEQ ID NO 89
<211> LENGTH: 9
<212> TYPE: PRT
<213> ORGANISM: Homo sapiens

<400> SEQUENCE: 89

Val Asp Asp Gln Thr Leu Pro Pro Leu
1               5

<210> SEQ ID NO 90
<211> LENGTH: 9
<212> TYPE: PRT
<213> ORGANISM: Homo sapiens

<400> SEQUENCE: 90

Lys Pro Leu Arg Pro Gly Ser Ser Leu
1               5

<210> SEQ ID NO 91
<211> LENGTH: 9
<212> TYPE: PRT
<213> ORGANISM: Homo sapiens

<400> SEQUENCE: 91

Leu Arg Pro Gly Ser Ser Leu Gly Leu
1               5

<210> SEQ ID NO 92
<211> LENGTH: 9
<212> TYPE: PRT
<213> ORGANISM: Homo sapiens

<400> SEQUENCE: 92

Val Ile Arg Asn Ala Lys Val Ala Ala
1               5

<210> SEQ ID NO 93
<211> LENGTH: 9
<212> TYPE: PRT
<213> ORGANISM: Homo sapiens

<400> SEQUENCE: 93

Leu Leu Arg Ser Lys Pro Ala Leu Pro
1               5

<210> SEQ ID NO 94
<211> LENGTH: 9
<212> TYPE: PRT
<213> ORGANISM: Homo sapiens

<400> SEQUENCE: 94

Pro Leu Met Leu Leu Leu Leu Gly Pro
1               5

<210> SEQ ID NO 95
<211> LENGTH: 9
<212> TYPE: PRT
<213> ORGANISM: Homo sapiens
```

```
<400> SEQUENCE: 95

Gly Ala Leu Pro Arg Pro Ala Gln Ala
1               5

<210> SEQ ID NO 96
<211> LENGTH: 9
<212> TYPE: PRT
<213> ORGANISM: Homo sapiens

<400> SEQUENCE: 96

Leu Ala Thr Asp Pro Arg Phe Leu Ile
1               5

<210> SEQ ID NO 97
<211> LENGTH: 9
<212> TYPE: PRT
<213> ORGANISM: Homo sapiens

<400> SEQUENCE: 97

Thr Asp Pro Arg Phe Leu Ile Leu Leu
1               5

<210> SEQ ID NO 98
<211> LENGTH: 9
<212> TYPE: PRT
<213> ORGANISM: Homo sapiens

<400> SEQUENCE: 98

Ile Leu Leu Gly Ser Pro Lys Leu Arg
1               5

<210> SEQ ID NO 99
<211> LENGTH: 9
<212> TYPE: PRT
<213> ORGANISM: Homo sapiens

<400> SEQUENCE: 99

Ile Pro Pro Asp Val Glu Glu Lys Leu
1               5

<210> SEQ ID NO 100
<211> LENGTH: 9
<212> TYPE: PRT
<213> ORGANISM: Homo sapiens

<400> SEQUENCE: 100

Leu Leu Leu Arg Glu His Tyr Gln Lys
1               5

<210> SEQ ID NO 101
<211> LENGTH: 9
<212> TYPE: PRT
<213> ORGANISM: Homo sapiens

<400> SEQUENCE: 101

Glu Asp Phe Ile Gln Leu His Lys Leu
1               5

<210> SEQ ID NO 102
<211> LENGTH: 9
<212> TYPE: PRT
<213> ORGANISM: Homo sapiens

<400> SEQUENCE: 102
```

Asn Ala Lys Leu Tyr Gly Pro Asp Val
1               5

<210> SEQ ID NO 103
<211> LENGTH: 9
<212> TYPE: PRT
<213> ORGANISM: Homo sapiens

<400> SEQUENCE: 103

Thr Arg Pro Gly Lys Lys Val Trp Leu
1               5

<210> SEQ ID NO 104
<211> LENGTH: 9
<212> TYPE: PRT
<213> ORGANISM: Homo sapiens

<400> SEQUENCE: 104

Leu Pro Asp Tyr Trp Leu Ser Leu Leu
1               5

<210> SEQ ID NO 105
<211> LENGTH: 9
<212> TYPE: PRT
<213> ORGANISM: Homo sapiens

<400> SEQUENCE: 105

Ser Leu Leu Phe Lys Lys Leu Val Gly
1               5

<210> SEQ ID NO 106
<211> LENGTH: 9
<212> TYPE: PRT
<213> ORGANISM: Homo sapiens

<400> SEQUENCE: 106

Ala Ile Asn Leu His Asn Val Thr Lys
1               5

<210> SEQ ID NO 107
<211> LENGTH: 9
<212> TYPE: PRT
<213> ORGANISM: Homo sapiens

<400> SEQUENCE: 107

Arg Pro Leu Gly Pro His Gly Leu Leu
1               5

<210> SEQ ID NO 108
<211> LENGTH: 9
<212> TYPE: PRT
<213> ORGANISM: Homo sapiens

<400> SEQUENCE: 108

Leu Asn Gly Leu Thr Leu Lys Met Val
1               5

<210> SEQ ID NO 109
<211> LENGTH: 9
<212> TYPE: PRT
<213> ORGANISM: Homo sapiens

<400> SEQUENCE: 109

Leu Lys Met Val Asp Asp Gln Thr Leu
1               5

<210> SEQ ID NO 110
<211> LENGTH: 9
<212> TYPE: PRT
<213> ORGANISM: Homo sapiens

<400> SEQUENCE: 110

Gln Thr Leu Pro Pro Leu Met Glu Lys
1               5

<210> SEQ ID NO 111
<211> LENGTH: 9
<212> TYPE: PRT
<213> ORGANISM: Homo sapiens

<400> SEQUENCE: 111

Thr Leu Pro Pro Leu Met Glu Lys Pro
1               5

<210> SEQ ID NO 112
<211> LENGTH: 9
<212> TYPE: PRT
<213> ORGANISM: Homo sapiens

<400> SEQUENCE: 112

Ser Leu Gly Leu Pro Ala Phe Ser Tyr
1               5

<210> SEQ ID NO 113
<211> LENGTH: 9
<212> TYPE: PRT
<213> ORGANISM: Homo sapiens

<400> SEQUENCE: 113

Gly Leu Pro Ala Phe Ser Tyr Ser Phe
1               5

<210> SEQ ID NO 114
<211> LENGTH: 9
<212> TYPE: PRT
<213> ORGANISM: Homo sapiens

<400> SEQUENCE: 114

Phe Phe Val Ile Arg Asn Ala Lys Val
1               5

<210> SEQ ID NO 115
<211> LENGTH: 9
<212> TYPE: PRT
<213> ORGANISM: Homo sapiens

<400> SEQUENCE: 115

Ser Lys Pro Ala Leu Pro Pro Pro Leu
1               5

<210> SEQ ID NO 116
<211> LENGTH: 9
<212> TYPE: PRT
<213> ORGANISM: Homo sapiens

<400> SEQUENCE: 116

Met Leu Leu Leu Leu Gly Pro Leu Gly
1               5

```
<210> SEQ ID NO 117
<211> LENGTH: 9
<212> TYPE: PRT
<213> ORGANISM: Homo sapiens

<400> SEQUENCE: 117

Ala Leu Pro Arg Pro Ala Gln Ala Gln
1               5

<210> SEQ ID NO 118
<211> LENGTH: 9
<212> TYPE: PRT
<213> ORGANISM: Homo sapiens

<400> SEQUENCE: 118

Leu His Leu Val Ser Pro Ser Phe Leu
1               5

<210> SEQ ID NO 119
<211> LENGTH: 9
<212> TYPE: PRT
<213> ORGANISM: Homo sapiens

<400> SEQUENCE: 119

Ser Pro Ser Phe Leu Ser Val Thr Ile
1               5

<210> SEQ ID NO 120
<211> LENGTH: 9
<212> TYPE: PRT
<213> ORGANISM: Homo sapiens

<400> SEQUENCE: 120

Leu Ser Val Thr Ile Asp Ala Asn Leu
1               5

<210> SEQ ID NO 121
<211> LENGTH: 9
<212> TYPE: PRT
<213> ORGANISM: Homo sapiens

<400> SEQUENCE: 121

Val Thr Ile Asp Ala Asn Leu Ala Thr
1               5

<210> SEQ ID NO 122
<211> LENGTH: 9
<212> TYPE: PRT
<213> ORGANISM: Homo sapiens

<400> SEQUENCE: 122

Phe Leu Ile Leu Leu Gly Ser Pro Lys
1               5

<210> SEQ ID NO 123
<211> LENGTH: 9
<212> TYPE: PRT
<213> ORGANISM: Homo sapiens

<400> SEQUENCE: 123

Ala Arg Gly Leu Ser Pro Ala Tyr Leu
1               5

<210> SEQ ID NO 124
<211> LENGTH: 9
```

```
<212> TYPE: PRT
<213> ORGANISM: Homo sapiens

<400> SEQUENCE: 124

Gly Leu Ser Pro Ala Tyr Leu Arg Phe
1               5

<210> SEQ ID NO 125
<211> LENGTH: 9
<212> TYPE: PRT
<213> ORGANISM: Homo sapiens

<400> SEQUENCE: 125

Phe Gly Gly Thr Lys Thr Asp Phe Leu
1               5

<210> SEQ ID NO 126
<211> LENGTH: 9
<212> TYPE: PRT
<213> ORGANISM: Homo sapiens

<400> SEQUENCE: 126

Leu Ile Phe Asp Pro Lys Lys Glu Ser
1               5

<210> SEQ ID NO 127
<211> LENGTH: 9
<212> TYPE: PRT
<213> ORGANISM: Homo sapiens

<400> SEQUENCE: 127

Val Leu Tyr Thr Phe Ala Asn Cys Ser
1               5

<210> SEQ ID NO 128
<211> LENGTH: 9
<212> TYPE: PRT
<213> ORGANISM: Homo sapiens

<400> SEQUENCE: 128

Ala Leu Leu Arg Thr Ala Asp Leu Gln
1               5

<210> SEQ ID NO 129
<211> LENGTH: 9
<212> TYPE: PRT
<213> ORGANISM: Homo sapiens

<400> SEQUENCE: 129

Gln Leu Leu Leu Asp Tyr Cys Ser Ser
1               5

<210> SEQ ID NO 130
<211> LENGTH: 9
<212> TYPE: PRT
<213> ORGANISM: Homo sapiens

<400> SEQUENCE: 130

Lys Gly Tyr Asn Ile Ser Trp Glu Leu
1               5

<210> SEQ ID NO 131
<211> LENGTH: 9
<212> TYPE: PRT
<213> ORGANISM: Homo sapiens
```

```
<400> SEQUENCE: 131

Phe Ile Asn Gly Ser Gln Leu Gly Glu
1               5

<210> SEQ ID NO 132
<211> LENGTH: 9
<212> TYPE: PRT
<213> ORGANISM: Homo sapiens

<400> SEQUENCE: 132

Lys Leu Leu Arg Lys Ser Thr Phe Lys
1               5

<210> SEQ ID NO 133
<211> LENGTH: 9
<212> TYPE: PRT
<213> ORGANISM: Homo sapiens

<400> SEQUENCE: 133

Lys Ser Thr Phe Lys Asn Ala Lys Leu
1               5

<210> SEQ ID NO 134
<211> LENGTH: 9
<212> TYPE: PRT
<213> ORGANISM: Homo sapiens

<400> SEQUENCE: 134

Thr Ala Lys Met Leu Lys Ser Phe Leu
1               5

<210> SEQ ID NO 135
<211> LENGTH: 9
<212> TYPE: PRT
<213> ORGANISM: Homo sapiens

<400> SEQUENCE: 135

Met Leu Lys Ser Phe Leu Lys Ala Gly
1               5

<210> SEQ ID NO 136
<211> LENGTH: 9
<212> TYPE: PRT
<213> ORGANISM: Homo sapiens

<400> SEQUENCE: 136

Gly Gly Ala Pro Leu Leu Ser Asp Thr
1               5

<210> SEQ ID NO 137
<211> LENGTH: 9
<212> TYPE: PRT
<213> ORGANISM: Homo sapiens

<400> SEQUENCE: 137

Thr Phe Ala Ala Gly Phe Met Trp Leu
1               5

<210> SEQ ID NO 138
<211> LENGTH: 9
<212> TYPE: PRT
<213> ORGANISM: Homo sapiens

<400> SEQUENCE: 138
```

```
Arg Met Gly Ile Glu Val Val Met Arg
1               5
```

<210> SEQ ID NO 139
<211> LENGTH: 9
<212> TYPE: PRT
<213> ORGANISM: Homo sapiens

<400> SEQUENCE: 139

```
Val Met Arg Gln Val Phe Phe Gly Ala
1               5
```

<210> SEQ ID NO 140
<211> LENGTH: 9
<212> TYPE: PRT
<213> ORGANISM: Homo sapiens

<400> SEQUENCE: 140

```
Phe Phe Gly Ala Gly Asn Tyr His Leu
1               5
```

<210> SEQ ID NO 141
<211> LENGTH: 9
<212> TYPE: PRT
<213> ORGANISM: Homo sapiens

<400> SEQUENCE: 141

```
Leu Ser Leu Leu Phe Lys Lys Leu Val
1               5
```

<210> SEQ ID NO 142
<211> LENGTH: 9
<212> TYPE: PRT
<213> ORGANISM: Homo sapiens

<400> SEQUENCE: 142

```
Leu Met Ala Ser Val Gln Gly Ser Lys
1               5
```

<210> SEQ ID NO 143
<211> LENGTH: 9
<212> TYPE: PRT
<213> ORGANISM: Homo sapiens

<400> SEQUENCE: 143

```
Val Gln Gly Ser Lys Arg Arg Lys Leu
1               5
```

<210> SEQ ID NO 144
<211> LENGTH: 9
<212> TYPE: PRT
<213> ORGANISM: Homo sapiens

<400> SEQUENCE: 144

```
Lys Arg Arg Lys Leu Arg Val Tyr Leu
1               5
```

<210> SEQ ID NO 145
<211> LENGTH: 9
<212> TYPE: PRT
<213> ORGANISM: Homo sapiens

<400> SEQUENCE: 145

```
Tyr Ala Ile Asn Leu His Asn Val Thr
```

```
<210> SEQ ID NO 146
<211> LENGTH: 9
<212> TYPE: PRT
<213> ORGANISM: Homo sapiens

<400> SEQUENCE: 146

Tyr Leu Arg Leu Pro Tyr Pro Phe Ser
1               5

<210> SEQ ID NO 147
<211> LENGTH: 9
<212> TYPE: PRT
<213> ORGANISM: Homo sapiens

<400> SEQUENCE: 147

Val Asp Lys Tyr Leu Leu Arg Pro Leu
1               5

<210> SEQ ID NO 148
<211> LENGTH: 9
<212> TYPE: PRT
<213> ORGANISM: Homo sapiens

<400> SEQUENCE: 148

Leu Met Glu Lys Pro Leu Arg Pro Gly
1               5

<210> SEQ ID NO 149
<211> LENGTH: 9
<212> TYPE: PRT
<213> ORGANISM: Homo sapiens

<400> SEQUENCE: 149

Leu Gly Pro Leu Ser Pro Gly Ala Leu
1               5

<210> SEQ ID NO 150
<211> LENGTH: 9
<212> TYPE: PRT
<213> ORGANISM: Homo sapiens

<400> SEQUENCE: 150

Asp Leu Asp Phe Phe Thr Gln Glu Pro
1               5

<210> SEQ ID NO 151
<211> LENGTH: 9
<212> TYPE: PRT
<213> ORGANISM: Homo sapiens

<400> SEQUENCE: 151

Phe Leu Ile Phe Asp Pro Lys Lys Glu
1               5

<210> SEQ ID NO 152
<211> LENGTH: 9
<212> TYPE: PRT
<213> ORGANISM: Homo sapiens

<400> SEQUENCE: 152

Gln Asp Ile Cys Lys Tyr Gly Ser Ile
1               5
```

```
<210> SEQ ID NO 153
<211> LENGTH: 9
<212> TYPE: PRT
<213> ORGANISM: Homo sapiens

<400> SEQUENCE: 153

Gln Leu Leu Leu Arg Glu His Tyr Gln
1               5

<210> SEQ ID NO 154
<211> LENGTH: 9
<212> TYPE: PRT
<213> ORGANISM: Homo sapiens

<400> SEQUENCE: 154

Leu Leu Arg Thr Ala Asp Leu Gln Trp
1               5

<210> SEQ ID NO 155
<211> LENGTH: 9
<212> TYPE: PRT
<213> ORGANISM: Homo sapiens

<400> SEQUENCE: 155

Asp Leu Gln Trp Asn Ser Ser Asn Ala
1               5

<210> SEQ ID NO 156
<211> LENGTH: 9
<212> TYPE: PRT
<213> ORGANISM: Homo sapiens

<400> SEQUENCE: 156

Gln Trp Asn Ser Ser Asn Ala Gln Leu
1               5

<210> SEQ ID NO 157
<211> LENGTH: 9
<212> TYPE: PRT
<213> ORGANISM: Homo sapiens

<400> SEQUENCE: 157

Leu Leu Asp Tyr Cys Ser Ser Lys Gly
1               5

<210> SEQ ID NO 158
<211> LENGTH: 9
<212> TYPE: PRT
<213> ORGANISM: Homo sapiens

<400> SEQUENCE: 158

Val Trp Leu Gly Glu Thr Ser Ser Ala
1               5

<210> SEQ ID NO 159
<211> LENGTH: 9
<212> TYPE: PRT
<213> ORGANISM: Homo sapiens

<400> SEQUENCE: 159

Trp Leu Gly Glu Thr Ser Ser Ala Tyr
1               5

<210> SEQ ID NO 160
```

```
<211> LENGTH: 9
<212> TYPE: PRT
<213> ORGANISM: Homo sapiens

<400> SEQUENCE: 160

Leu Gly Leu Ser Ala Arg Met Gly Ile
1               5

<210> SEQ ID NO 161
<211> LENGTH: 9
<212> TYPE: PRT
<213> ORGANISM: Homo sapiens

<400> SEQUENCE: 161

Phe Asp Pro Leu Pro Asp Tyr Trp Leu
1               5

<210> SEQ ID NO 162
<211> LENGTH: 9
<212> TYPE: PRT
<213> ORGANISM: Homo sapiens

<400> SEQUENCE: 162

Gly Leu Thr Leu Lys Met Val Asp Asp
1               5

<210> SEQ ID NO 163
<211> LENGTH: 9
<212> TYPE: PRT
<213> ORGANISM: Homo sapiens

<400> SEQUENCE: 163

Thr Leu Lys Met Val Asp Asp Gln Thr
1               5

<210> SEQ ID NO 164
<211> LENGTH: 9
<212> TYPE: PRT
<213> ORGANISM: Homo sapiens

<400> SEQUENCE: 164

Pro Ala Phe Ser Tyr Ser Phe Phe Val
1               5

<210> SEQ ID NO 165
<211> LENGTH: 9
<212> TYPE: PRT
<213> ORGANISM: Homo sapiens

<400> SEQUENCE: 165

Pro Pro Pro Leu Met Leu Leu Leu Leu
1               5

<210> SEQ ID NO 166
<211> LENGTH: 9
<212> TYPE: PRT
<213> ORGANISM: Homo sapiens

<400> SEQUENCE: 166

Pro Leu Ser Pro Gly Ala Leu Pro Arg
1               5

<210> SEQ ID NO 167
<211> LENGTH: 9
<212> TYPE: PRT
```

<213> ORGANISM: Homo sapiens

<400> SEQUENCE: 167

Arg Pro Ala Gln Ala Gln Asp Val Val
1               5

<210> SEQ ID NO 168
<211> LENGTH: 9
<212> TYPE: PRT
<213> ORGANISM: Homo sapiens

<400> SEQUENCE: 168

Leu Asp Phe Phe Thr Gln Glu Pro Leu
1               5

<210> SEQ ID NO 169
<211> LENGTH: 9
<212> TYPE: PRT
<213> ORGANISM: Homo sapiens

<400> SEQUENCE: 169

Lys Tyr Gly Ser Ile Pro Pro Asp Val
1               5

<210> SEQ ID NO 170
<211> LENGTH: 9
<212> TYPE: PRT
<213> ORGANISM: Homo sapiens

<400> SEQUENCE: 170

Lys Leu Arg Leu Glu Trp Pro Tyr Gln
1               5

<210> SEQ ID NO 171
<211> LENGTH: 9
<212> TYPE: PRT
<213> ORGANISM: Homo sapiens

<400> SEQUENCE: 171

Arg Leu Glu Trp Pro Tyr Gln Glu Gln
1               5

<210> SEQ ID NO 172
<211> LENGTH: 9
<212> TYPE: PRT
<213> ORGANISM: Homo sapiens

<400> SEQUENCE: 172

Trp Pro Tyr Gln Glu Gln Leu Leu Leu
1               5

<210> SEQ ID NO 173
<211> LENGTH: 9
<212> TYPE: PRT
<213> ORGANISM: Homo sapiens

<400> SEQUENCE: 173

Thr Tyr Ser Arg Ser Ser Val Asp Val
1               5

<210> SEQ ID NO 174
<211> LENGTH: 9
<212> TYPE: PRT
<213> ORGANISM: Homo sapiens

```
-continued

<400> SEQUENCE: 174

Phe Gly Leu Asn Ala Leu Leu Arg Thr
1               5

<210> SEQ ID NO 175
<211> LENGTH: 9
<212> TYPE: PRT
<213> ORGANISM: Homo sapiens

<400> SEQUENCE: 175

Tyr Cys Ser Ser Lys Gly Tyr Asn Ile
1               5

<210> SEQ ID NO 176
<211> LENGTH: 9
<212> TYPE: PRT
<213> ORGANISM: Homo sapiens

<400> SEQUENCE: 176

Asn Ile Ser Trp Glu Leu Gly Asn Glu
1               5

<210> SEQ ID NO 177
<211> LENGTH: 9
<212> TYPE: PRT
<213> ORGANISM: Homo sapiens

<400> SEQUENCE: 177

Asn Ser Phe Leu Lys Lys Ala Asp Ile
1               5

<210> SEQ ID NO 178
<211> LENGTH: 9
<212> TYPE: PRT
<213> ORGANISM: Homo sapiens

<400> SEQUENCE: 178

Lys Ala Asp Ile Phe Ile Asn Gly Ser
1               5

<210> SEQ ID NO 179
<211> LENGTH: 9
<212> TYPE: PRT
<213> ORGANISM: Homo sapiens

<400> SEQUENCE: 179

Lys Thr Ala Lys Met Leu Lys Ser Phe
1               5

<210> SEQ ID NO 180
<211> LENGTH: 9
<212> TYPE: PRT
<213> ORGANISM: Homo sapiens

<400> SEQUENCE: 180

Phe Lys Lys Leu Val Gly Thr Lys Val
1               5

<210> SEQ ID NO 181
<211> LENGTH: 9
<212> TYPE: PRT
<213> ORGANISM: Homo sapiens

<400> SEQUENCE: 181
```

```
Tyr Leu His Cys Thr Asn Thr Asp Asn
1               5

<210> SEQ ID NO 182
<211> LENGTH: 9
<212> TYPE: PRT
<213> ORGANISM: Homo sapiens

<400> SEQUENCE: 182

Leu Thr Leu Tyr Ala Ile Asn Leu His
1               5

<210> SEQ ID NO 183
<211> LENGTH: 9
<212> TYPE: PRT
<213> ORGANISM: Homo sapiens

<400> SEQUENCE: 183

Thr Leu Tyr Ala Ile Asn Leu His Asn
1               5

<210> SEQ ID NO 184
<211> LENGTH: 9
<212> TYPE: PRT
<213> ORGANISM: Homo sapiens

<400> SEQUENCE: 184

His Asn Val Thr Lys Tyr Leu Arg Leu
1               5

<210> SEQ ID NO 185
<211> LENGTH: 9
<212> TYPE: PRT
<213> ORGANISM: Homo sapiens

<400> SEQUENCE: 185

Leu Thr Leu Lys Met Val Asp Asp Gln
1               5

<210> SEQ ID NO 186
<211> LENGTH: 9
<212> TYPE: PRT
<213> ORGANISM: Homo sapiens

<400> SEQUENCE: 186

Pro Leu Met Glu Lys Pro Leu Arg Pro
1               5

<210> SEQ ID NO 187
<211> LENGTH: 9
<212> TYPE: PRT
<213> ORGANISM: Homo sapiens

<400> SEQUENCE: 187

Arg Asn Ala Lys Val Ala Ala Cys Ile
1               5

<210> SEQ ID NO 188
<211> LENGTH: 9
<212> TYPE: PRT
<213> ORGANISM: Homo sapiens

<400> SEQUENCE: 188

Phe Phe Thr Gln Glu Pro Leu His Leu
1               5
```

<210> SEQ ID NO 189
<211> LENGTH: 9
<212> TYPE: PRT
<213> ORGANISM: Homo sapiens

<400> SEQUENCE: 189

His Leu Val Ser Pro Ser Phe Leu Ser
1               5

<210> SEQ ID NO 190
<211> LENGTH: 9
<212> TYPE: PRT
<213> ORGANISM: Homo sapiens

<400> SEQUENCE: 190

Leu Ala Arg Gly Leu Ser Pro Ala Tyr
1               5

<210> SEQ ID NO 191
<211> LENGTH: 9
<212> TYPE: PRT
<213> ORGANISM: Homo sapiens

<400> SEQUENCE: 191

Ile Phe Asp Pro Lys Lys Glu Ser Thr
1               5

<210> SEQ ID NO 192
<211> LENGTH: 9
<212> TYPE: PRT
<213> ORGANISM: Homo sapiens

<400> SEQUENCE: 192

Gln Val Asn Gln Asp Ile Cys Lys Tyr
1               5

<210> SEQ ID NO 193
<211> LENGTH: 9
<212> TYPE: PRT
<213> ORGANISM: Homo sapiens

<400> SEQUENCE: 193

Ser Val Asp Val Leu Tyr Thr Phe Ala
1               5

<210> SEQ ID NO 194
<211> LENGTH: 9
<212> TYPE: PRT
<213> ORGANISM: Homo sapiens

<400> SEQUENCE: 194

Gly Leu Asp Leu Ile Phe Gly Leu Asn
1               5

<210> SEQ ID NO 195
<211> LENGTH: 9
<212> TYPE: PRT
<213> ORGANISM: Homo sapiens

<400> SEQUENCE: 195

Asn Ser Ser Asn Ala Gln Leu Leu Leu
1               5

```
<210> SEQ ID NO 196
<211> LENGTH: 9
<212> TYPE: PRT
<213> ORGANISM: Homo sapiens

<400> SEQUENCE: 196

Gly Ser Gln Leu Gly Glu Asp Phe Ile
1               5

<210> SEQ ID NO 197
<211> LENGTH: 9
<212> TYPE: PRT
<213> ORGANISM: Homo sapiens

<400> SEQUENCE: 197

Asp Phe Ile Gln Leu His Lys Leu Leu
1               5

<210> SEQ ID NO 198
<211> LENGTH: 9
<212> TYPE: PRT
<213> ORGANISM: Homo sapiens

<400> SEQUENCE: 198

Gln Pro Arg Arg Lys Thr Ala Lys Met
1               5

<210> SEQ ID NO 199
<211> LENGTH: 9
<212> TYPE: PRT
<213> ORGANISM: Homo sapiens

<400> SEQUENCE: 199

Lys Ala Gly Gly Glu Val Ile Asp Ser
1               5

<210> SEQ ID NO 200
<211> LENGTH: 9
<212> TYPE: PRT
<213> ORGANISM: Homo sapiens

<400> SEQUENCE: 200

Val Ile Asp Ser Val Thr Trp His His
1               5

<210> SEQ ID NO 201
<211> LENGTH: 9
<212> TYPE: PRT
<213> ORGANISM: Homo sapiens

<400> SEQUENCE: 201

Tyr Tyr Leu Asn Gly Arg Thr Ala Thr
1               5

<210> SEQ ID NO 202
<211> LENGTH: 9
<212> TYPE: PRT
<213> ORGANISM: Homo sapiens

<400> SEQUENCE: 202

Arg Glu Asp Phe Leu Asn Pro Asp Val
1               5

<210> SEQ ID NO 203
<211> LENGTH: 9
```

```
<212> TYPE: PRT
<213> ORGANISM: Homo sapiens

<400> SEQUENCE: 203

Lys Leu Gly Leu Ser Ala Arg Met Gly
1               5

<210> SEQ ID NO 204
<211> LENGTH: 9
<212> TYPE: PRT
<213> ORGANISM: Homo sapiens

<400> SEQUENCE: 204

Gly Leu Ser Ala Arg Met Gly Ile Glu
1               5

<210> SEQ ID NO 205
<211> LENGTH: 9
<212> TYPE: PRT
<213> ORGANISM: Homo sapiens

<400> SEQUENCE: 205

Ala Arg Met Gly Ile Glu Val Val Met
1               5

<210> SEQ ID NO 206
<211> LENGTH: 9
<212> TYPE: PRT
<213> ORGANISM: Homo sapiens

<400> SEQUENCE: 206

His Leu Val Asp Glu Asn Phe Asp Pro
1               5

<210> SEQ ID NO 207
<211> LENGTH: 9
<212> TYPE: PRT
<213> ORGANISM: Homo sapiens

<400> SEQUENCE: 207

Tyr Trp Leu Ser Leu Leu Phe Lys Lys
1               5

<210> SEQ ID NO 208
<211> LENGTH: 9
<212> TYPE: PRT
<213> ORGANISM: Homo sapiens

<400> SEQUENCE: 208

Gly Ser Lys Arg Arg Lys Leu Arg Val
1               5

<210> SEQ ID NO 209
<211> LENGTH: 9
<212> TYPE: PRT
<213> ORGANISM: Homo sapiens

<400> SEQUENCE: 209

Glu Gly Asp Leu Thr Leu Tyr Ala Ile
1               5

<210> SEQ ID NO 210
<211> LENGTH: 9
<212> TYPE: PRT
<213> ORGANISM: Homo sapiens
```

```
<400> SEQUENCE: 210

Asn Lys Gln Val Asp Lys Tyr Leu Leu
1               5

<210> SEQ ID NO 211
<211> LENGTH: 9
<212> TYPE: PRT
<213> ORGANISM: Homo sapiens

<400> SEQUENCE: 211

Leu Gly Pro His Gly Leu Leu Ser Lys
1               5

<210> SEQ ID NO 212
<211> LENGTH: 9
<212> TYPE: PRT
<213> ORGANISM: Homo sapiens

<400> SEQUENCE: 212

Leu Pro Pro Leu Met Glu Lys Pro Leu
1               5

<210> SEQ ID NO 213
<211> LENGTH: 9
<212> TYPE: PRT
<213> ORGANISM: Homo sapiens

<400> SEQUENCE: 213

Pro Leu Arg Pro Gly Ser Ser Leu Gly
1               5

<210> SEQ ID NO 214
<211> LENGTH: 9
<212> TYPE: PRT
<213> ORGANISM: Homo sapiens

<400> SEQUENCE: 214

Ile Arg Asn Ala Lys Val Ala Ala Cys
1               5

<210> SEQ ID NO 215
<211> LENGTH: 9
<212> TYPE: PRT
<213> ORGANISM: Homo sapiens

<400> SEQUENCE: 215

Gly Pro Leu Gly Pro Leu Ser Pro Gly
1               5

<210> SEQ ID NO 216
<211> LENGTH: 9
<212> TYPE: PRT
<213> ORGANISM: Homo sapiens

<400> SEQUENCE: 216

Pro Leu His Leu Val Ser Pro Ser Phe
1               5

<210> SEQ ID NO 217
<211> LENGTH: 9
<212> TYPE: PRT
<213> ORGANISM: Homo sapiens

<400> SEQUENCE: 217
```

```
Val Ser Pro Ser Phe Leu Ser Val Thr
1               5

<210> SEQ ID NO 218
<211> LENGTH: 9
<212> TYPE: PRT
<213> ORGANISM: Homo sapiens

<400> SEQUENCE: 218

Ser Phe Leu Ser Val Thr Ile Asp Ala
1               5

<210> SEQ ID NO 219
<211> LENGTH: 9
<212> TYPE: PRT
<213> ORGANISM: Homo sapiens

<400> SEQUENCE: 219

Ser Val Thr Ile Asp Ala Asn Leu Ala
1               5

<210> SEQ ID NO 220
<211> LENGTH: 9
<212> TYPE: PRT
<213> ORGANISM: Homo sapiens

<400> SEQUENCE: 220

Leu Arg Phe Gly Gly Thr Lys Thr Asp
1               5

<210> SEQ ID NO 221
<211> LENGTH: 9
<212> TYPE: PRT
<213> ORGANISM: Homo sapiens

<400> SEQUENCE: 221

Gly Ser Ile Pro Pro Asp Val Glu Glu
1               5

<210> SEQ ID NO 222
<211> LENGTH: 9
<212> TYPE: PRT
<213> ORGANISM: Homo sapiens

<400> SEQUENCE: 222

Pro Asp Val Glu Glu Lys Leu Arg Leu
1               5

<210> SEQ ID NO 223
<211> LENGTH: 9
<212> TYPE: PRT
<213> ORGANISM: Homo sapiens

<400> SEQUENCE: 223

Asn Ser Thr Tyr Ser Arg Ser Ser Val
1               5

<210> SEQ ID NO 224
<211> LENGTH: 9
<212> TYPE: PRT
<213> ORGANISM: Homo sapiens

<400> SEQUENCE: 224

Ser Ser Val Asp Val Leu Tyr Thr Phe
```

-continued

```
<210> SEQ ID NO 225
<211> LENGTH: 9
<212> TYPE: PRT
<213> ORGANISM: Homo sapiens

<400> SEQUENCE: 225

Leu Asp Leu Ile Phe Gly Leu Asn Ala
1               5

<210> SEQ ID NO 226
<211> LENGTH: 9
<212> TYPE: PRT
<213> ORGANISM: Homo sapiens

<400> SEQUENCE: 226

Trp Asn Ser Ser Asn Ala Gln Leu Leu
1               5

<210> SEQ ID NO 227
<211> LENGTH: 9
<212> TYPE: PRT
<213> ORGANISM: Homo sapiens

<400> SEQUENCE: 227

Ser Asn Ala Gln Leu Leu Leu Asp Tyr
1               5

<210> SEQ ID NO 228
<211> LENGTH: 9
<212> TYPE: PRT
<213> ORGANISM: Homo sapiens

<400> SEQUENCE: 228

Glu Leu Gly Asn Glu Pro Asn Ser Phe
1               5

<210> SEQ ID NO 229
<211> LENGTH: 9
<212> TYPE: PRT
<213> ORGANISM: Homo sapiens

<400> SEQUENCE: 229

Phe Ile Gln Leu His Lys Leu Leu Arg
1               5

<210> SEQ ID NO 230
<211> LENGTH: 9
<212> TYPE: PRT
<213> ORGANISM: Homo sapiens

<400> SEQUENCE: 230

Ile Gln Leu His Lys Leu Leu Arg Lys
1               5

<210> SEQ ID NO 231
<211> LENGTH: 9
<212> TYPE: PRT
<213> ORGANISM: Homo sapiens

<400> SEQUENCE: 231

Asp Val Gly Gln Pro Arg Arg Lys Thr
1               5
```

```
<210> SEQ ID NO 232
<211> LENGTH: 9
<212> TYPE: PRT
<213> ORGANISM: Homo sapiens

<400> SEQUENCE: 232

Leu Lys Ala Gly Gly Glu Val Ile Asp
1               5

<210> SEQ ID NO 233
<211> LENGTH: 9
<212> TYPE: PRT
<213> ORGANISM: Homo sapiens

<400> SEQUENCE: 233

Asp Ile Phe Ile Ser Ser Val Gln Lys
1               5

<210> SEQ ID NO 234
<211> LENGTH: 9
<212> TYPE: PRT
<213> ORGANISM: Homo sapiens

<400> SEQUENCE: 234

Gly Lys Lys Val Trp Leu Gly Glu Thr
1               5

<210> SEQ ID NO 235
<211> LENGTH: 9
<212> TYPE: PRT
<213> ORGANISM: Homo sapiens

<400> SEQUENCE: 235

Lys Val Trp Leu Gly Glu Thr Ser Ser
1               5

<210> SEQ ID NO 236
<211> LENGTH: 9
<212> TYPE: PRT
<213> ORGANISM: Homo sapiens

<400> SEQUENCE: 236

Phe Ala Ala Gly Phe Met Trp Leu Asp
1               5

<210> SEQ ID NO 237
<211> LENGTH: 9
<212> TYPE: PRT
<213> ORGANISM: Homo sapiens

<400> SEQUENCE: 237

Asp Lys Leu Gly Leu Ser Ala Arg Met
1               5

<210> SEQ ID NO 238
<211> LENGTH: 9
<212> TYPE: PRT
<213> ORGANISM: Homo sapiens

<400> SEQUENCE: 238

Val Val Met Arg Gln Val Phe Phe Gly
1               5

<210> SEQ ID NO 239
```

```
<211> LENGTH: 9
<212> TYPE: PRT
<213> ORGANISM: Homo sapiens

<400> SEQUENCE: 239

Asn Pro Arg Tyr Lys Glu Gly Asp Leu
1               5

<210> SEQ ID NO 240
<211> LENGTH: 9
<212> TYPE: PRT
<213> ORGANISM: Homo sapiens

<400> SEQUENCE: 240

Lys Glu Gly Asp Leu Thr Leu Tyr Ala
1               5

<210> SEQ ID NO 241
<211> LENGTH: 9
<212> TYPE: PRT
<213> ORGANISM: Homo sapiens

<400> SEQUENCE: 241

Ile Asn Leu His Asn Val Thr Lys Tyr
1               5

<210> SEQ ID NO 242
<211> LENGTH: 9
<212> TYPE: PRT
<213> ORGANISM: Homo sapiens

<400> SEQUENCE: 242

Arg Leu Pro Tyr Pro Phe Ser Asn Lys
1               5

<210> SEQ ID NO 243
<211> LENGTH: 9
<212> TYPE: PRT
<213> ORGANISM: Homo sapiens

<400> SEQUENCE: 243

Ser Asn Lys Gln Val Asp Lys Tyr Leu
1               5

<210> SEQ ID NO 244
<211> LENGTH: 9
<212> TYPE: PRT
<213> ORGANISM: Homo sapiens

<400> SEQUENCE: 244

Gln Val Asp Lys Tyr Leu Leu Arg Pro
1               5

<210> SEQ ID NO 245
<211> LENGTH: 9
<212> TYPE: PRT
<213> ORGANISM: Homo sapiens

<400> SEQUENCE: 245

Pro Leu Gly Pro His Gly Leu Leu Ser
1               5

<210> SEQ ID NO 246
<211> LENGTH: 9
<212> TYPE: PRT
```

```
<213> ORGANISM: Homo sapiens

<400> SEQUENCE: 246

Gly Pro His Gly Leu Leu Ser Lys Ser
1               5

<210> SEQ ID NO 247
<211> LENGTH: 9
<212> TYPE: PRT
<213> ORGANISM: Homo sapiens

<400> SEQUENCE: 247

Lys Met Val Asp Asp Gln Thr Leu Pro
1               5

<210> SEQ ID NO 248
<211> LENGTH: 9
<212> TYPE: PRT
<213> ORGANISM: Homo sapiens

<400> SEQUENCE: 248

Tyr Ser Phe Phe Val Ile Arg Asn Ala
1               5

<210> SEQ ID NO 249
<211> LENGTH: 9
<212> TYPE: PRT
<213> ORGANISM: Homo sapiens

<400> SEQUENCE: 249

Phe Val Ile Arg Asn Ala Lys Val Ala
1               5

<210> SEQ ID NO 250
<211> LENGTH: 9
<212> TYPE: PRT
<213> ORGANISM: Homo sapiens

<400> SEQUENCE: 250

Lys Pro Ala Leu Pro Pro Pro Leu Met
1               5

<210> SEQ ID NO 251
<211> LENGTH: 9
<212> TYPE: PRT
<213> ORGANISM: Homo sapiens

<400> SEQUENCE: 251

Leu Ser Pro Gly Ala Leu Pro Arg Pro
1               5

<210> SEQ ID NO 252
<211> LENGTH: 9
<212> TYPE: PRT
<213> ORGANISM: Homo sapiens

<400> SEQUENCE: 252

Gln Ala Gln Asp Val Val Asp Leu Asp
1               5

<210> SEQ ID NO 253
<211> LENGTH: 9
<212> TYPE: PRT
<213> ORGANISM: Homo sapiens
```

<400> SEQUENCE: 253

Asp Val Val Asp Leu Asp Phe Phe Thr
1               5

<210> SEQ ID NO 254
<211> LENGTH: 9
<212> TYPE: PRT
<213> ORGANISM: Homo sapiens

<400> SEQUENCE: 254

Arg Phe Leu Ile Leu Leu Gly Ser Pro
1               5

<210> SEQ ID NO 255
<211> LENGTH: 9
<212> TYPE: PRT
<213> ORGANISM: Homo sapiens

<400> SEQUENCE: 255

Arg Thr Leu Ala Arg Gly Leu Ser Pro
1               5

<210> SEQ ID NO 256
<211> LENGTH: 9
<212> TYPE: PRT
<213> ORGANISM: Homo sapiens

<400> SEQUENCE: 256

Lys Thr Asp Phe Leu Ile Phe Asp Pro
1               5

<210> SEQ ID NO 257
<211> LENGTH: 9
<212> TYPE: PRT
<213> ORGANISM: Homo sapiens

<400> SEQUENCE: 257

Ser Thr Phe Glu Glu Arg Ser Tyr Trp
1               5

<210> SEQ ID NO 258
<211> LENGTH: 9
<212> TYPE: PRT
<213> ORGANISM: Homo sapiens

<400> SEQUENCE: 258

Asp Val Glu Glu Lys Leu Arg Leu Glu
1               5

<210> SEQ ID NO 259
<211> LENGTH: 9
<212> TYPE: PRT
<213> ORGANISM: Homo sapiens

<400> SEQUENCE: 259

Tyr Gln Lys Lys Phe Lys Asn Ser Thr
1               5

<210> SEQ ID NO 260
<211> LENGTH: 9
<212> TYPE: PRT
<213> ORGANISM: Homo sapiens

<400> SEQUENCE: 260

Arg Ser Ser Val Asp Val Leu Tyr Thr
1               5

<210> SEQ ID NO 261
<211> LENGTH: 9
<212> TYPE: PRT
<213> ORGANISM: Homo sapiens

<400> SEQUENCE: 261

Asn Ala Gln Leu Leu Asp Tyr Cys
1               5

<210> SEQ ID NO 262
<211> LENGTH: 9
<212> TYPE: PRT
<213> ORGANISM: Homo sapiens

<400> SEQUENCE: 262

Ile Ser Trp Glu Leu Gly Asn Glu Pro
1               5

<210> SEQ ID NO 263
<211> LENGTH: 9
<212> TYPE: PRT
<213> ORGANISM: Homo sapiens

<400> SEQUENCE: 263

Phe Lys Asn Ala Lys Leu Tyr Gly Pro
1               5

<210> SEQ ID NO 264
<211> LENGTH: 9
<212> TYPE: PRT
<213> ORGANISM: Homo sapiens

<400> SEQUENCE: 264

Ala Thr Arg Glu Asp Phe Leu Asn Pro
1               5

<210> SEQ ID NO 265
<211> LENGTH: 9
<212> TYPE: PRT
<213> ORGANISM: Homo sapiens

<400> SEQUENCE: 265

Asn Pro Asp Val Leu Asp Ile Phe Ile
1               5

<210> SEQ ID NO 266
<211> LENGTH: 9
<212> TYPE: PRT
<213> ORGANISM: Homo sapiens

<400> SEQUENCE: 266

Ser Thr Arg Pro Gly Lys Lys Val Trp
1               5

<210> SEQ ID NO 267
<211> LENGTH: 9
<212> TYPE: PRT
<213> ORGANISM: Homo sapiens

<400> SEQUENCE: 267

Gly Gly Gly Ala Pro Leu Leu Ser Asp
1               5

```
<210> SEQ ID NO 268
<211> LENGTH: 9
<212> TYPE: PRT
<213> ORGANISM: Homo sapiens

<400> SEQUENCE: 268

Gly Asn Tyr His Leu Val Asp Glu Asn
1               5

<210> SEQ ID NO 269
<211> LENGTH: 9
<212> TYPE: PRT
<213> ORGANISM: Homo sapiens

<400> SEQUENCE: 269

Lys Val Leu Met Ala Ser Val Gln Gly
1               5

<210> SEQ ID NO 270
<211> LENGTH: 9
<212> TYPE: PRT
<213> ORGANISM: Homo sapiens

<400> SEQUENCE: 270

Arg Val Tyr Leu His Cys Thr Asn Thr
1               5

<210> SEQ ID NO 271
<211> LENGTH: 9
<212> TYPE: PRT
<213> ORGANISM: Homo sapiens

<400> SEQUENCE: 271

Leu Arg Leu Pro Tyr Pro Phe Ser Asn
1               5

<210> SEQ ID NO 272
<211> LENGTH: 9
<212> TYPE: PRT
<213> ORGANISM: Homo sapiens

<400> SEQUENCE: 272

Leu Pro Tyr Pro Phe Ser Asn Lys Gln
1               5

<210> SEQ ID NO 273
<211> LENGTH: 9
<212> TYPE: PRT
<213> ORGANISM: Homo sapiens

<400> SEQUENCE: 273

Pro His Gly Leu Leu Ser Lys Ser Val
1               5

<210> SEQ ID NO 274
<211> LENGTH: 9
<212> TYPE: PRT
<213> ORGANISM: Homo sapiens

<400> SEQUENCE: 274

Val Gln Leu Asn Gly Leu Thr Leu Lys
1               5
```

```
<210> SEQ ID NO 275
<211> LENGTH: 9
<212> TYPE: PRT
<213> ORGANISM: Homo sapiens

<400> SEQUENCE: 275

Gly Ser Ser Leu Gly Leu Pro Ala Phe
1               5

<210> SEQ ID NO 276
<211> LENGTH: 9
<212> TYPE: PRT
<213> ORGANISM: Homo sapiens

<400> SEQUENCE: 276

Ser Ser Leu Gly Leu Pro Ala Phe Ser
1               5

<210> SEQ ID NO 277
<211> LENGTH: 9
<212> TYPE: PRT
<213> ORGANISM: Homo sapiens

<400> SEQUENCE: 277

Ala Phe Ser Tyr Ser Phe Phe Val Ile
1               5

<210> SEQ ID NO 278
<211> LENGTH: 9
<212> TYPE: PRT
<213> ORGANISM: Homo sapiens

<400> SEQUENCE: 278

Gln Glu Pro Leu His Leu Val Ser Pro
1               5

<210> SEQ ID NO 279
<211> LENGTH: 9
<212> TYPE: PRT
<213> ORGANISM: Homo sapiens

<400> SEQUENCE: 279

Gly Gly Thr Lys Thr Asp Phe Leu Ile
1               5

<210> SEQ ID NO 280
<211> LENGTH: 9
<212> TYPE: PRT
<213> ORGANISM: Homo sapiens

<400> SEQUENCE: 280

Trp Gln Ser Gln Val Asn Gln Asp Ile
1               5

<210> SEQ ID NO 281
<211> LENGTH: 9
<212> TYPE: PRT
<213> ORGANISM: Homo sapiens

<400> SEQUENCE: 281

Asp Ile Cys Lys Tyr Gly Ser Ile Pro
1               5

<210> SEQ ID NO 282
<211> LENGTH: 9
```

```
<212> TYPE: PRT
<213> ORGANISM: Homo sapiens

<400> SEQUENCE: 282

Cys Lys Tyr Gly Ser Ile Pro Pro Asp
1               5

<210> SEQ ID NO 283
<211> LENGTH: 9
<212> TYPE: PRT
<213> ORGANISM: Homo sapiens

<400> SEQUENCE: 283

Arg Thr Ala Asp Leu Gln Trp Asn Ser
1               5

<210> SEQ ID NO 284
<211> LENGTH: 9
<212> TYPE: PRT
<213> ORGANISM: Homo sapiens

<400> SEQUENCE: 284

Ser Ser Asn Ala Gln Leu Leu Leu Asp
1               5

<210> SEQ ID NO 285
<211> LENGTH: 9
<212> TYPE: PRT
<213> ORGANISM: Homo sapiens

<400> SEQUENCE: 285

Glu Pro Asn Ser Phe Leu Lys Lys Ala
1               5

<210> SEQ ID NO 286
<211> LENGTH: 9
<212> TYPE: PRT
<213> ORGANISM: Homo sapiens

<400> SEQUENCE: 286

Ile Asn Gly Ser Gln Leu Gly Glu Asp
1               5

<210> SEQ ID NO 287
<211> LENGTH: 9
<212> TYPE: PRT
<213> ORGANISM: Homo sapiens

<400> SEQUENCE: 287

Leu Tyr Gly Pro Asp Val Gly Gln Pro
1               5

<210> SEQ ID NO 288
<211> LENGTH: 9
<212> TYPE: PRT
<213> ORGANISM: Homo sapiens

<400> SEQUENCE: 288

Val Gly Gln Pro Arg Arg Lys Thr Ala
1               5

<210> SEQ ID NO 289
<211> LENGTH: 9
<212> TYPE: PRT
<213> ORGANISM: Homo sapiens
```

```
<400> SEQUENCE: 289

Glu Val Ile Asp Ser Val Thr Trp His
1               5

<210> SEQ ID NO 290
<211> LENGTH: 9
<212> TYPE: PRT
<213> ORGANISM: Homo sapiens

<400> SEQUENCE: 290

Glu Asp Phe Leu Asn Pro Asp Val Leu
1               5

<210> SEQ ID NO 291
<211> LENGTH: 9
<212> TYPE: PRT
<213> ORGANISM: Homo sapiens

<400> SEQUENCE: 291

Asp Val Leu Asp Ile Phe Ile Ser Ser
1               5

<210> SEQ ID NO 292
<211> LENGTH: 9
<212> TYPE: PRT
<213> ORGANISM: Homo sapiens

<400> SEQUENCE: 292

Phe Ile Ser Ser Val Gln Lys Val Phe
1               5

<210> SEQ ID NO 293
<211> LENGTH: 9
<212> TYPE: PRT
<213> ORGANISM: Homo sapiens

<400> SEQUENCE: 293

Gln Val Val Glu Ser Thr Arg Pro Gly
1               5

<210> SEQ ID NO 294
<211> LENGTH: 9
<212> TYPE: PRT
<213> ORGANISM: Homo sapiens

<400> SEQUENCE: 294

Glu Ser Thr Arg Pro Gly Lys Lys Val
1               5

<210> SEQ ID NO 295
<211> LENGTH: 9
<212> TYPE: PRT
<213> ORGANISM: Homo sapiens

<400> SEQUENCE: 295

Gly Ala Pro Leu Leu Ser Asp Thr Phe
1               5

<210> SEQ ID NO 296
<211> LENGTH: 9
<212> TYPE: PRT
<213> ORGANISM: Homo sapiens

<400> SEQUENCE: 296
```

Ala Pro Leu Leu Ser Asp Thr Phe Ala
1               5

<210> SEQ ID NO 297
<211> LENGTH: 9
<212> TYPE: PRT
<213> ORGANISM: Homo sapiens

<400> SEQUENCE: 297

Met Trp Leu Asp Lys Leu Gly Leu Ser
1               5

<210> SEQ ID NO 298
<211> LENGTH: 9
<212> TYPE: PRT
<213> ORGANISM: Homo sapiens

<400> SEQUENCE: 298

Leu Asp Lys Leu Gly Leu Ser Ala Arg
1               5

<210> SEQ ID NO 299
<211> LENGTH: 9
<212> TYPE: PRT
<213> ORGANISM: Homo sapiens

<400> SEQUENCE: 299

Met Gly Ile Glu Val Val Met Arg Gln
1               5

<210> SEQ ID NO 300
<211> LENGTH: 9
<212> TYPE: PRT
<213> ORGANISM: Homo sapiens

<400> SEQUENCE: 300

Ala Gly Asn Tyr His Leu Val Asp Glu
1               5

<210> SEQ ID NO 301
<211> LENGTH: 9
<212> TYPE: PRT
<213> ORGANISM: Homo sapiens

<400> SEQUENCE: 301

Leu Phe Lys Lys Leu Val Gly Thr Lys
1               5

<210> SEQ ID NO 302
<211> LENGTH: 9
<212> TYPE: PRT
<213> ORGANISM: Homo sapiens

<400> SEQUENCE: 302

Ser Val Gln Gly Ser Lys Arg Arg Lys
1               5

<210> SEQ ID NO 303
<211> LENGTH: 9
<212> TYPE: PRT
<213> ORGANISM: Homo sapiens

<400> SEQUENCE: 303

Val Tyr Leu His Cys Thr Asn Thr Asp

-continued

```
1               5

<210> SEQ ID NO 304
<211> LENGTH: 9
<212> TYPE: PRT
<213> ORGANISM: Homo sapiens

<400> SEQUENCE: 304

Asn Thr Asp Asn Pro Arg Tyr Lys Glu
1               5

<210> SEQ ID NO 305
<211> LENGTH: 9
<212> TYPE: PRT
<213> ORGANISM: Homo sapiens

<400> SEQUENCE: 305

Asn Val Thr Lys Tyr Leu Arg Leu Pro
1               5

<210> SEQ ID NO 306
<211> LENGTH: 9
<212> TYPE: PRT
<213> ORGANISM: Homo sapiens

<400> SEQUENCE: 306

Phe Ser Asn Lys Gln Val Asp Lys Tyr
1               5

<210> SEQ ID NO 307
<211> LENGTH: 9
<212> TYPE: PRT
<213> ORGANISM: Homo sapiens

<400> SEQUENCE: 307

Met Val Asp Asp Gln Thr Leu Pro Pro
1               5

<210> SEQ ID NO 308
<211> LENGTH: 9
<212> TYPE: PRT
<213> ORGANISM: Homo sapiens

<400> SEQUENCE: 308

Leu Gly Pro Leu Gly Pro Leu Ser Pro
1               5

<210> SEQ ID NO 309
<211> LENGTH: 9
<212> TYPE: PRT
<213> ORGANISM: Homo sapiens

<400> SEQUENCE: 309

Ser Pro Gly Ala Leu Pro Arg Pro Ala
1               5

<210> SEQ ID NO 310
<211> LENGTH: 9
<212> TYPE: PRT
<213> ORGANISM: Homo sapiens

<400> SEQUENCE: 310

Pro Arg Pro Ala Gln Ala Gln Asp Val
1               5
```

```
<210> SEQ ID NO 311
<211> LENGTH: 9
<212> TYPE: PRT
<213> ORGANISM: Homo sapiens

<400> SEQUENCE: 311

Val Val Asp Leu Asp Phe Phe Thr Gln
1               5

<210> SEQ ID NO 312
<211> LENGTH: 9
<212> TYPE: PRT
<213> ORGANISM: Homo sapiens

<400> SEQUENCE: 312

Leu Ser Pro Ala Tyr Leu Arg Phe Gly
1               5

<210> SEQ ID NO 313
<211> LENGTH: 9
<212> TYPE: PRT
<213> ORGANISM: Homo sapiens

<400> SEQUENCE: 313

Pro Ala Tyr Leu Arg Phe Gly Gly Thr
1               5

<210> SEQ ID NO 314
<211> LENGTH: 9
<212> TYPE: PRT
<213> ORGANISM: Homo sapiens

<400> SEQUENCE: 314

Ala Tyr Leu Arg Phe Gly Gly Thr Lys
1               5

<210> SEQ ID NO 315
<211> LENGTH: 9
<212> TYPE: PRT
<213> ORGANISM: Homo sapiens

<400> SEQUENCE: 315

Tyr Trp Gln Ser Gln Val Asn Gln Asp
1               5

<210> SEQ ID NO 316
<211> LENGTH: 9
<212> TYPE: PRT
<213> ORGANISM: Homo sapiens

<400> SEQUENCE: 316

Leu Arg Leu Glu Trp Pro Tyr Gln Glu
1               5

<210> SEQ ID NO 317
<211> LENGTH: 9
<212> TYPE: PRT
<213> ORGANISM: Homo sapiens

<400> SEQUENCE: 317

Tyr Gln Glu Gln Leu Leu Leu Arg Glu
1               5

<210> SEQ ID NO 318
```

```
<211> LENGTH: 9
<212> TYPE: PRT
<213> ORGANISM: Homo sapiens

<400> SEQUENCE: 318

Gln Glu Gln Leu Leu Leu Arg Glu His
1               5

<210> SEQ ID NO 319
<211> LENGTH: 9
<212> TYPE: PRT
<213> ORGANISM: Homo sapiens

<400> SEQUENCE: 319

Ser Thr Tyr Ser Arg Ser Ser Val Asp
1               5

<210> SEQ ID NO 320
<211> LENGTH: 9
<212> TYPE: PRT
<213> ORGANISM: Homo sapiens

<400> SEQUENCE: 320

Thr Ala Asp Leu Gln Trp Asn Ser Ser
1               5

<210> SEQ ID NO 321
<211> LENGTH: 9
<212> TYPE: PRT
<213> ORGANISM: Homo sapiens

<400> SEQUENCE: 321

Leu Gly Glu Asp Phe Ile Gln Leu His
1               5

<210> SEQ ID NO 322
<211> LENGTH: 9
<212> TYPE: PRT
<213> ORGANISM: Homo sapiens

<400> SEQUENCE: 322

Leu His Lys Leu Leu Arg Lys Ser Thr
1               5

<210> SEQ ID NO 323
<211> LENGTH: 9
<212> TYPE: PRT
<213> ORGANISM: Homo sapiens

<400> SEQUENCE: 323

Val Thr Trp His His Tyr Tyr Leu Asn
1               5

<210> SEQ ID NO 324
<211> LENGTH: 9
<212> TYPE: PRT
<213> ORGANISM: Homo sapiens

<400> SEQUENCE: 324

His Tyr Tyr Leu Asn Gly Arg Thr Ala
1               5

<210> SEQ ID NO 325
<211> LENGTH: 9
<212> TYPE: PRT
```

-continued

<213> ORGANISM: Homo sapiens

<400> SEQUENCE: 325

Leu Asn Pro Asp Val Leu Asp Ile Phe
1               5

<210> SEQ ID NO 326
<211> LENGTH: 9
<212> TYPE: PRT
<213> ORGANISM: Homo sapiens

<400> SEQUENCE: 326

Gln Lys Val Phe Gln Val Val Glu Ser
1               5

<210> SEQ ID NO 327
<211> LENGTH: 9
<212> TYPE: PRT
<213> ORGANISM: Homo sapiens

<400> SEQUENCE: 327

Gly Ala Gly Asn Tyr His Leu Val Asp
1               5

<210> SEQ ID NO 328
<211> LENGTH: 9
<212> TYPE: PRT
<213> ORGANISM: Homo sapiens

<400> SEQUENCE: 328

Ser Lys Arg Arg Lys Leu Arg Val Tyr
1               5

<210> SEQ ID NO 329
<211> LENGTH: 9
<212> TYPE: PRT
<213> ORGANISM: Homo sapiens

<400> SEQUENCE: 329

Tyr Lys Glu Gly Asp Leu Thr Leu Tyr
1               5

<210> SEQ ID NO 330
<211> LENGTH: 9
<212> TYPE: PRT
<213> ORGANISM: Homo sapiens

<400> SEQUENCE: 330

Arg Ser Lys Pro Ala Leu Pro Pro Pro
1               5

<210> SEQ ID NO 331
<211> LENGTH: 9
<212> TYPE: PRT
<213> ORGANISM: Homo sapiens

<400> SEQUENCE: 331

Gly Pro Leu Ser Pro Gly Ala Leu Pro
1               5

<210> SEQ ID NO 332
<211> LENGTH: 9
<212> TYPE: PRT
<213> ORGANISM: Homo sapiens

```
<400> SEQUENCE: 332

Leu Pro Arg Pro Ala Gln Ala Gln Asp
1               5

<210> SEQ ID NO 333
<211> LENGTH: 9
<212> TYPE: PRT
<213> ORGANISM: Homo sapiens

<400> SEQUENCE: 333

Asp Ala Asn Leu Ala Thr Asp Pro Arg
1               5

<210> SEQ ID NO 334
<211> LENGTH: 9
<212> TYPE: PRT
<213> ORGANISM: Homo sapiens

<400> SEQUENCE: 334

Gly Ser Pro Lys Leu Arg Thr Leu Ala
1               5

<210> SEQ ID NO 335
<211> LENGTH: 9
<212> TYPE: PRT
<213> ORGANISM: Homo sapiens

<400> SEQUENCE: 335

Glu Arg Ser Tyr Trp Gln Ser Gln Val
1               5

<210> SEQ ID NO 336
<211> LENGTH: 9
<212> TYPE: PRT
<213> ORGANISM: Homo sapiens

<400> SEQUENCE: 336

Glu Trp Pro Tyr Gln Glu Gln Leu Leu
1               5

<210> SEQ ID NO 337
<211> LENGTH: 9
<212> TYPE: PRT
<213> ORGANISM: Homo sapiens

<400> SEQUENCE: 337

Asp Val Leu Tyr Thr Phe Ala Asn Cys
1               5

<210> SEQ ID NO 338
<211> LENGTH: 9
<212> TYPE: PRT
<213> ORGANISM: Homo sapiens

<400> SEQUENCE: 338

Leu Asn Ala Leu Leu Arg Thr Ala Asp
1               5

<210> SEQ ID NO 339
<211> LENGTH: 9
<212> TYPE: PRT
<213> ORGANISM: Homo sapiens

<400> SEQUENCE: 339
```

Ala Asp Leu Gln Trp Asn Ser Ser Asn
1               5

<210> SEQ ID NO 340
<211> LENGTH: 9
<212> TYPE: PRT
<213> ORGANISM: Homo sapiens

<400> SEQUENCE: 340

Ala Gln Leu Leu Leu Asp Tyr Cys Ser
1               5

<210> SEQ ID NO 341
<211> LENGTH: 9
<212> TYPE: PRT
<213> ORGANISM: Homo sapiens

<400> SEQUENCE: 341

Ser Ser Lys Gly Tyr Asn Ile Ser Trp
1               5

<210> SEQ ID NO 342
<211> LENGTH: 9
<212> TYPE: PRT
<213> ORGANISM: Homo sapiens

<400> SEQUENCE: 342

Tyr Asn Ile Ser Trp Glu Leu Gly Asn
1               5

<210> SEQ ID NO 343
<211> LENGTH: 9
<212> TYPE: PRT
<213> ORGANISM: Homo sapiens

<400> SEQUENCE: 343

Ile Phe Ile Asn Gly Ser Gln Leu Gly
1               5

<210> SEQ ID NO 344
<211> LENGTH: 9
<212> TYPE: PRT
<213> ORGANISM: Homo sapiens

<400> SEQUENCE: 344

Ser Gln Leu Gly Glu Asp Phe Ile Gln
1               5

<210> SEQ ID NO 345
<211> LENGTH: 9
<212> TYPE: PRT
<213> ORGANISM: Homo sapiens

<400> SEQUENCE: 345

Ser Thr Phe Lys Asn Ala Lys Leu Tyr
1               5

<210> SEQ ID NO 346
<211> LENGTH: 9
<212> TYPE: PRT
<213> ORGANISM: Homo sapiens

<400> SEQUENCE: 346

Pro Arg Arg Lys Thr Ala Lys Met Leu
1               5

<210> SEQ ID NO 347
<211> LENGTH: 9
<212> TYPE: PRT
<213> ORGANISM: Homo sapiens

<400> SEQUENCE: 347

Trp His His Tyr Tyr Leu Asn Gly Arg
1               5

<210> SEQ ID NO 348
<211> LENGTH: 9
<212> TYPE: PRT
<213> ORGANISM: Homo sapiens

<400> SEQUENCE: 348

Thr Arg Glu Asp Phe Leu Asn Pro Asp
1               5

<210> SEQ ID NO 349
<211> LENGTH: 9
<212> TYPE: PRT
<213> ORGANISM: Homo sapiens

<400> SEQUENCE: 349

Val Val Glu Ser Thr Arg Pro Gly Lys
1               5

<210> SEQ ID NO 350
<211> LENGTH: 9
<212> TYPE: PRT
<213> ORGANISM: Homo sapiens

<400> SEQUENCE: 350

Thr Ser Ser Ala Tyr Gly Gly Gly Ala
1               5

<210> SEQ ID NO 351
<211> LENGTH: 9
<212> TYPE: PRT
<213> ORGANISM: Homo sapiens

<400> SEQUENCE: 351

Ser Ser Ala Tyr Gly Gly Gly Ala Pro
1               5

<210> SEQ ID NO 352
<211> LENGTH: 9
<212> TYPE: PRT
<213> ORGANISM: Homo sapiens

<400> SEQUENCE: 352

Leu Ser Asp Thr Phe Ala Ala Gly Phe
1               5

<210> SEQ ID NO 353
<211> LENGTH: 9
<212> TYPE: PRT
<213> ORGANISM: Homo sapiens

<400> SEQUENCE: 353

Ala Ala Gly Phe Met Trp Leu Asp Lys
1               5

<210> SEQ ID NO 354
<211> LENGTH: 9
<212> TYPE: PRT
<213> ORGANISM: Homo sapiens

<400> SEQUENCE: 354

Gln Val Phe Phe Gly Ala Gly Asn Tyr
1               5

<210> SEQ ID NO 355
<211> LENGTH: 9
<212> TYPE: PRT
<213> ORGANISM: Homo sapiens

<400> SEQUENCE: 355

Met Ala Ser Val Gln Gly Ser Lys Arg
1               5

<210> SEQ ID NO 356
<211> LENGTH: 9
<212> TYPE: PRT
<213> ORGANISM: Homo sapiens

<400> SEQUENCE: 356

Cys Thr Asn Thr Asp Asn Pro Arg Tyr
1               5

<210> SEQ ID NO 357
<211> LENGTH: 9
<212> TYPE: PRT
<213> ORGANISM: Homo sapiens

<400> SEQUENCE: 357

Gly Asp Leu Thr Leu Tyr Ala Ile Asn
1               5

<210> SEQ ID NO 358
<211> LENGTH: 9
<212> TYPE: PRT
<213> ORGANISM: Homo sapiens

<400> SEQUENCE: 358

Thr Lys Tyr Leu Arg Leu Pro Tyr Pro
1               5

<210> SEQ ID NO 359
<211> LENGTH: 9
<212> TYPE: PRT
<213> ORGANISM: Homo sapiens

<400> SEQUENCE: 359

Lys Ser Val Gln Leu Asn Gly Leu Thr
1               5

<210> SEQ ID NO 360
<211> LENGTH: 9
<212> TYPE: PRT
<213> ORGANISM: Homo sapiens

<400> SEQUENCE: 360

Leu Gly Leu Pro Ala Phe Ser Tyr Ser
1               5

<210> SEQ ID NO 361
<211> LENGTH: 9

<212> TYPE: PRT
<213> ORGANISM: Homo sapiens

<400> SEQUENCE: 361

Ser Tyr Ser Phe Phe Val Ile Arg Asn
1               5

<210> SEQ ID NO 362
<211> LENGTH: 9
<212> TYPE: PRT
<213> ORGANISM: Homo sapiens

<400> SEQUENCE: 362

Pro Pro Leu Met Leu Leu Leu Leu Gly
1               5

<210> SEQ ID NO 363
<211> LENGTH: 9
<212> TYPE: PRT
<213> ORGANISM: Homo sapiens

<400> SEQUENCE: 363

Val Asp Leu Asp Phe Phe Thr Gln Glu
1               5

<210> SEQ ID NO 364
<211> LENGTH: 9
<212> TYPE: PRT
<213> ORGANISM: Homo sapiens

<400> SEQUENCE: 364

Ile Asp Ala Asn Leu Ala Thr Asp Pro
1               5

<210> SEQ ID NO 365
<211> LENGTH: 9
<212> TYPE: PRT
<213> ORGANISM: Homo sapiens

<400> SEQUENCE: 365

Ala Asn Leu Ala Thr Asp Pro Arg Phe
1               5

<210> SEQ ID NO 366
<211> LENGTH: 9
<212> TYPE: PRT
<213> ORGANISM: Homo sapiens

<400> SEQUENCE: 366

Ser Pro Lys Leu Arg Thr Leu Ala Arg
1               5

<210> SEQ ID NO 367
<211> LENGTH: 9
<212> TYPE: PRT
<213> ORGANISM: Homo sapiens

<400> SEQUENCE: 367

Pro Lys Leu Arg Thr Leu Ala Arg Gly
1               5

<210> SEQ ID NO 368
<211> LENGTH: 9
<212> TYPE: PRT
<213> ORGANISM: Homo sapiens -continued

<400> SEQUENCE: 368

Ser Pro Ala Tyr Leu Arg Phe Gly Gly
1               5

<210> SEQ ID NO 369
<211> LENGTH: 9
<212> TYPE: PRT
<213> ORGANISM: Homo sapiens

<400> SEQUENCE: 369

Gly Thr Lys Thr Asp Phe Leu Ile Phe
1               5

<210> SEQ ID NO 370
<211> LENGTH: 9
<212> TYPE: PRT
<213> ORGANISM: Homo sapiens

<400> SEQUENCE: 370

Thr Lys Thr Asp Phe Leu Ile Phe Asp
1               5

<210> SEQ ID NO 371
<211> LENGTH: 9
<212> TYPE: PRT
<213> ORGANISM: Homo sapiens

<400> SEQUENCE: 371

Asp Phe Leu Ile Phe Asp Pro Lys Lys
1               5

<210> SEQ ID NO 372
<211> LENGTH: 9
<212> TYPE: PRT
<213> ORGANISM: Homo sapiens

<400> SEQUENCE: 372

Ser Tyr Trp Gln Ser Gln Val Asn Gln
1               5

<210> SEQ ID NO 373
<211> LENGTH: 9
<212> TYPE: PRT
<213> ORGANISM: Homo sapiens

<400> SEQUENCE: 373

Lys Phe Lys Asn Ser Thr Tyr Ser Arg
1               5

<210> SEQ ID NO 374
<211> LENGTH: 9
<212> TYPE: PRT
<213> ORGANISM: Homo sapiens

<400> SEQUENCE: 374

Val Asp Val Leu Tyr Thr Phe Ala Asn
1               5

<210> SEQ ID NO 375
<211> LENGTH: 9
<212> TYPE: PRT
<213> ORGANISM: Homo sapiens

<400> SEQUENCE: 375

```
Leu Arg Thr Ala Asp Leu Gln Trp Asn
1               5

<210> SEQ ID NO 376
<211> LENGTH: 9
<212> TYPE: PRT
<213> ORGANISM: Homo sapiens

<400> SEQUENCE: 376

Leu Gln Trp Asn Ser Ser Asn Ala Gln
1               5

<210> SEQ ID NO 377
<211> LENGTH: 9
<212> TYPE: PRT
<213> ORGANISM: Homo sapiens

<400> SEQUENCE: 377

Ser Lys Gly Tyr Asn Ile Ser Trp Glu
1               5

<210> SEQ ID NO 378
<211> LENGTH: 9
<212> TYPE: PRT
<213> ORGANISM: Homo sapiens

<400> SEQUENCE: 378

Trp Glu Leu Gly Asn Glu Pro Asn Ser
1               5

<210> SEQ ID NO 379
<211> LENGTH: 9
<212> TYPE: PRT
<213> ORGANISM: Homo sapiens

<400> SEQUENCE: 379

Ser Phe Leu Lys Lys Ala Asp Ile Phe
1               5

<210> SEQ ID NO 380
<211> LENGTH: 9
<212> TYPE: PRT
<213> ORGANISM: Homo sapiens

<400> SEQUENCE: 380

Leu Lys Lys Ala Asp Ile Phe Ile Asn
1               5

<210> SEQ ID NO 381
<211> LENGTH: 9
<212> TYPE: PRT
<213> ORGANISM: Homo sapiens

<400> SEQUENCE: 381

Ala Asp Ile Phe Ile Asn Gly Ser Gln
1               5

<210> SEQ ID NO 382
<211> LENGTH: 9
<212> TYPE: PRT
<213> ORGANISM: Homo sapiens

<400> SEQUENCE: 382

Ala Lys Leu Tyr Gly Pro Asp Val Gly
```

```
1               5
```

<210> SEQ ID NO 383
<211> LENGTH: 9
<212> TYPE: PRT
<213> ORGANISM: Homo sapiens

<400> SEQUENCE: 383

```
Leu Lys Ser Phe Leu Lys Ala Gly Gly
1               5
```

<210> SEQ ID NO 384
<211> LENGTH: 9
<212> TYPE: PRT
<213> ORGANISM: Homo sapiens

<400> SEQUENCE: 384

```
Gly Glu Val Ile Asp Ser Val Thr Trp
1               5
```

<210> SEQ ID NO 385
<211> LENGTH: 9
<212> TYPE: PRT
<213> ORGANISM: Homo sapiens

<400> SEQUENCE: 385

```
His His Tyr Tyr Leu Asn Gly Arg Thr
1               5
```

<210> SEQ ID NO 386
<211> LENGTH: 9
<212> TYPE: PRT
<213> ORGANISM: Homo sapiens

<400> SEQUENCE: 386

```
Arg Pro Gly Lys Lys Val Trp Leu Gly
1               5
```

<210> SEQ ID NO 387
<211> LENGTH: 9
<212> TYPE: PRT
<213> ORGANISM: Homo sapiens

<400> SEQUENCE: 387

```
Tyr Gly Gly Gly Ala Pro Leu Leu Ser
1               5
```

<210> SEQ ID NO 388
<211> LENGTH: 9
<212> TYPE: PRT
<213> ORGANISM: Homo sapiens

<400> SEQUENCE: 388

```
Val Phe Phe Gly Ala Gly Asn Tyr His
1               5
```

<210> SEQ ID NO 389
<211> LENGTH: 9
<212> TYPE: PRT
<213> ORGANISM: Homo sapiens

<400> SEQUENCE: 389

```
Tyr His Leu Val Asp Glu Asn Phe Asp
1               5
```

```
<210> SEQ ID NO 390
<211> LENGTH: 9
<212> TYPE: PRT
<213> ORGANISM: Homo sapiens

<400> SEQUENCE: 390

Glu Asn Phe Asp Pro Leu Pro Asp Tyr
1               5

<210> SEQ ID NO 391
<211> LENGTH: 9
<212> TYPE: PRT
<213> ORGANISM: Homo sapiens

<400> SEQUENCE: 391

Asp Tyr Trp Leu Ser Leu Leu Phe Lys
1               5

<210> SEQ ID NO 392
<211> LENGTH: 9
<212> TYPE: PRT
<213> ORGANISM: Homo sapiens

<400> SEQUENCE: 392

Val Gly Thr Lys Val Leu Met Ala Ser
1               5

<210> SEQ ID NO 393
<211> LENGTH: 9
<212> TYPE: PRT
<213> ORGANISM: Homo sapiens

<400> SEQUENCE: 393

Val Thr Lys Tyr Leu Arg Leu Pro Tyr
1               5

<210> SEQ ID NO 394
<211> LENGTH: 9
<212> TYPE: PRT
<213> ORGANISM: Homo sapiens

<400> SEQUENCE: 394

Lys Tyr Leu Arg Leu Pro Tyr Pro Phe
1               5

<210> SEQ ID NO 395
<211> LENGTH: 9
<212> TYPE: PRT
<213> ORGANISM: Homo sapiens

<400> SEQUENCE: 395

Pro Tyr Pro Phe Ser Asn Lys Gln Val
1               5

<210> SEQ ID NO 396
<211> LENGTH: 9
<212> TYPE: PRT
<213> ORGANISM: Homo sapiens

<400> SEQUENCE: 396

Lys Tyr Leu Leu Arg Pro Leu Gly Pro
1               5

<210> SEQ ID NO 397
```

-continued

<211> LENGTH: 9
<212> TYPE: PRT
<213> ORGANISM: Homo sapiens

<400> SEQUENCE: 397

Asp Asp Gln Thr Leu Pro Pro Leu Met
1               5

<210> SEQ ID NO 398
<211> LENGTH: 9
<212> TYPE: PRT
<213> ORGANISM: Homo sapiens

<400> SEQUENCE: 398

Phe Ser Tyr Ser Phe Phe Val Ile Arg
1               5

<210> SEQ ID NO 399
<211> LENGTH: 9
<212> TYPE: PRT
<213> ORGANISM: Homo sapiens

<400> SEQUENCE: 399

Ser Phe Phe Val Ile Arg Asn Ala Lys
1               5

<210> SEQ ID NO 400
<211> LENGTH: 9
<212> TYPE: PRT
<213> ORGANISM: Homo sapiens

<400> SEQUENCE: 400

Leu Arg Ser Lys Pro Ala Leu Pro Pro
1               5

<210> SEQ ID NO 401
<211> LENGTH: 9
<212> TYPE: PRT
<213> ORGANISM: Homo sapiens

<400> SEQUENCE: 401

Gln Asp Val Val Asp Leu Asp Phe Phe
1               5

<210> SEQ ID NO 402
<211> LENGTH: 9
<212> TYPE: PRT
<213> ORGANISM: Homo sapiens

<400> SEQUENCE: 402

Glu Pro Leu His Leu Val Ser Pro Ser
1               5

<210> SEQ ID NO 403
<211> LENGTH: 9
<212> TYPE: PRT
<213> ORGANISM: Homo sapiens

<400> SEQUENCE: 403

Asp Pro Arg Phe Leu Ile Leu Leu Gly
1               5

<210> SEQ ID NO 404
<211> LENGTH: 9
<212> TYPE: PRT

-continued

<213> ORGANISM: Homo sapiens

<400> SEQUENCE: 404

Pro Arg Phe Leu Ile Leu Leu Gly Ser
1               5

<210> SEQ ID NO 405
<211> LENGTH: 9
<212> TYPE: PRT
<213> ORGANISM: Homo sapiens

<400> SEQUENCE: 405

Arg Gly Leu Ser Pro Ala Tyr Leu Arg
1               5

<210> SEQ ID NO 406
<211> LENGTH: 9
<212> TYPE: PRT
<213> ORGANISM: Homo sapiens

<400> SEQUENCE: 406

Phe Asp Pro Lys Lys Glu Ser Thr Phe
1               5

<210> SEQ ID NO 407
<211> LENGTH: 9
<212> TYPE: PRT
<213> ORGANISM: Homo sapiens

<400> SEQUENCE: 407

Val Glu Glu Lys Leu Arg Leu Glu Trp
1               5

<210> SEQ ID NO 408
<211> LENGTH: 9
<212> TYPE: PRT
<213> ORGANISM: Homo sapiens

<400> SEQUENCE: 408

Pro Tyr Gln Glu Gln Leu Leu Leu Arg
1               5

<210> SEQ ID NO 409
<211> LENGTH: 9
<212> TYPE: PRT
<213> ORGANISM: Homo sapiens

<400> SEQUENCE: 409

Lys Asn Ser Thr Tyr Ser Arg Ser Ser
1               5

<210> SEQ ID NO 410
<211> LENGTH: 9
<212> TYPE: PRT
<213> ORGANISM: Homo sapiens

<400> SEQUENCE: 410

Ser Arg Ser Ser Val Asp Val Leu Tyr
1               5

<210> SEQ ID NO 411
<211> LENGTH: 9
<212> TYPE: PRT
<213> ORGANISM: Homo sapiens

```
<400> SEQUENCE: 411

Asn Cys Ser Gly Leu Asp Leu Ile Phe
1               5

<210> SEQ ID NO 412
<211> LENGTH: 9
<212> TYPE: PRT
<213> ORGANISM: Homo sapiens

<400> SEQUENCE: 412

Cys Ser Gly Leu Asp Leu Ile Phe Gly
1               5

<210> SEQ ID NO 413
<211> LENGTH: 9
<212> TYPE: PRT
<213> ORGANISM: Homo sapiens

<400> SEQUENCE: 413

Lys Lys Ala Asp Ile Phe Ile Asn Gly
1               5

<210> SEQ ID NO 414
<211> LENGTH: 9
<212> TYPE: PRT
<213> ORGANISM: Homo sapiens

<400> SEQUENCE: 414

His Lys Leu Leu Arg Lys Ser Thr Phe
1               5

<210> SEQ ID NO 415
<211> LENGTH: 9
<212> TYPE: PRT
<213> ORGANISM: Homo sapiens

<400> SEQUENCE: 415

Leu Arg Lys Ser Thr Phe Lys Asn Ala
1               5

<210> SEQ ID NO 416
<211> LENGTH: 9
<212> TYPE: PRT
<213> ORGANISM: Homo sapiens

<400> SEQUENCE: 416

Lys Asn Ala Lys Leu Tyr Gly Pro Asp
1               5

<210> SEQ ID NO 417
<211> LENGTH: 9
<212> TYPE: PRT
<213> ORGANISM: Homo sapiens

<400> SEQUENCE: 417

Gly Pro Asp Val Gly Gln Pro Arg Arg
1               5

<210> SEQ ID NO 418
<211> LENGTH: 9
<212> TYPE: PRT
<213> ORGANISM: Homo sapiens

<400> SEQUENCE: 418
```

Ala Lys Met Leu Lys Ser Phe Leu Lys
1               5

<210> SEQ ID NO 419
<211> LENGTH: 9
<212> TYPE: PRT
<213> ORGANISM: Homo sapiens

<400> SEQUENCE: 419

Lys Ser Phe Leu Lys Ala Gly Gly Glu
1               5

<210> SEQ ID NO 420
<211> LENGTH: 9
<212> TYPE: PRT
<213> ORGANISM: Homo sapiens

<400> SEQUENCE: 420

Gly Gly Glu Val Ile Asp Ser Val Thr
1               5

<210> SEQ ID NO 421
<211> LENGTH: 9
<212> TYPE: PRT
<213> ORGANISM: Homo sapiens

<400> SEQUENCE: 421

Asn Gly Arg Thr Ala Thr Arg Glu Asp
1               5

<210> SEQ ID NO 422
<211> LENGTH: 9
<212> TYPE: PRT
<213> ORGANISM: Homo sapiens

<400> SEQUENCE: 422

Asp Phe Leu Asn Pro Asp Val Leu Asp
1               5

<210> SEQ ID NO 423
<211> LENGTH: 9
<212> TYPE: PRT
<213> ORGANISM: Homo sapiens

<400> SEQUENCE: 423

Ile Ser Ser Val Gln Lys Val Phe Gln
1               5

<210> SEQ ID NO 424
<211> LENGTH: 9
<212> TYPE: PRT
<213> ORGANISM: Homo sapiens

<400> SEQUENCE: 424

Lys Lys Val Trp Leu Gly Glu Thr Ser
1               5

<210> SEQ ID NO 425
<211> LENGTH: 9
<212> TYPE: PRT
<213> ORGANISM: Homo sapiens

<400> SEQUENCE: 425

Ser Asp Thr Phe Ala Ala Gly Phe Met
1               5

<210> SEQ ID NO 426
<211> LENGTH: 9
<212> TYPE: PRT
<213> ORGANISM: Homo sapiens

<400> SEQUENCE: 426

Asp Thr Phe Ala Ala Gly Phe Met Trp
1               5

<210> SEQ ID NO 427
<211> LENGTH: 9
<212> TYPE: PRT
<213> ORGANISM: Homo sapiens

<400> SEQUENCE: 427

Arg Arg Lys Leu Arg Val Tyr Leu His
1               5

<210> SEQ ID NO 428
<211> LENGTH: 9
<212> TYPE: PRT
<213> ORGANISM: Homo sapiens

<400> SEQUENCE: 428

Leu Arg Val Tyr Leu His Cys Thr Asn
1               5

<210> SEQ ID NO 429
<211> LENGTH: 9
<212> TYPE: PRT
<213> ORGANISM: Homo sapiens

<400> SEQUENCE: 429

Leu His Cys Thr Asn Thr Asp Asn Pro
1               5

<210> SEQ ID NO 430
<211> LENGTH: 9
<212> TYPE: PRT
<213> ORGANISM: Homo sapiens

<400> SEQUENCE: 430

Thr Asp Asn Pro Arg Tyr Lys Glu Gly
1               5

<210> SEQ ID NO 431
<211> LENGTH: 9
<212> TYPE: PRT
<213> ORGANISM: Homo sapiens

<400> SEQUENCE: 431

Leu His Asn Val Thr Lys Tyr Leu Arg
1               5

<210> SEQ ID NO 432
<211> LENGTH: 9
<212> TYPE: PRT
<213> ORGANISM: Homo sapiens

<400> SEQUENCE: 432

Lys Gln Val Asp Lys Tyr Leu Leu Arg
1               5

```
<210> SEQ ID NO 433
<211> LENGTH: 9
<212> TYPE: PRT
<213> ORGANISM: Homo sapiens

<400> SEQUENCE: 433

Met Glu Lys Pro Leu Arg Pro Gly Ser
1               5

<210> SEQ ID NO 434
<211> LENGTH: 9
<212> TYPE: PRT
<213> ORGANISM: Homo sapiens

<400> SEQUENCE: 434

Arg Pro Gly Ser Ser Leu Gly Leu Pro
1               5

<210> SEQ ID NO 435
<211> LENGTH: 9
<212> TYPE: PRT
<213> ORGANISM: Homo sapiens

<400> SEQUENCE: 435

Pro Ala Gln Ala Gln Asp Val Val Asp
1               5

<210> SEQ ID NO 436
<211> LENGTH: 9
<212> TYPE: PRT
<213> ORGANISM: Homo sapiens

<400> SEQUENCE: 436

Ala Gln Asp Val Val Asp Leu Asp Phe
1               5

<210> SEQ ID NO 437
<211> LENGTH: 9
<212> TYPE: PRT
<213> ORGANISM: Homo sapiens

<400> SEQUENCE: 437

Thr Gln Glu Pro Leu His Leu Val Ser
1               5

<210> SEQ ID NO 438
<211> LENGTH: 9
<212> TYPE: PRT
<213> ORGANISM: Homo sapiens

<400> SEQUENCE: 438

Tyr Gly Ser Ile Pro Pro Asp Val Glu
1               5

<210> SEQ ID NO 439
<211> LENGTH: 9
<212> TYPE: PRT
<213> ORGANISM: Homo sapiens

<400> SEQUENCE: 439

Leu Arg Glu His Tyr Gln Lys Lys Phe
1               5

<210> SEQ ID NO 440
<211> LENGTH: 9
```

-continued

<212> TYPE: PRT
<213> ORGANISM: Homo sapiens

<400> SEQUENCE: 440

Ile Phe Gly Leu Asn Ala Leu Leu Arg
1               5

<210> SEQ ID NO 441
<211> LENGTH: 9
<212> TYPE: PRT
<213> ORGANISM: Homo sapiens

<400> SEQUENCE: 441

Leu Asp Tyr Cys Ser Ser Lys Gly Tyr
1               5

<210> SEQ ID NO 442
<211> LENGTH: 9
<212> TYPE: PRT
<213> ORGANISM: Homo sapiens

<400> SEQUENCE: 442

Cys Ser Ser Lys Gly Tyr Asn Ile Ser
1               5

<210> SEQ ID NO 443
<211> LENGTH: 9
<212> TYPE: PRT
<213> ORGANISM: Homo sapiens

<400> SEQUENCE: 443

Ser Trp Glu Leu Gly Asn Glu Pro Asn
1               5

<210> SEQ ID NO 444
<211> LENGTH: 9
<212> TYPE: PRT
<213> ORGANISM: Homo sapiens

<400> SEQUENCE: 444

Asn Glu Pro Asn Ser Phe Leu Lys Lys
1               5

<210> SEQ ID NO 445
<211> LENGTH: 9
<212> TYPE: PRT
<213> ORGANISM: Homo sapiens

<400> SEQUENCE: 445

Arg Lys Ser Thr Phe Lys Asn Ala Lys
1               5

<210> SEQ ID NO 446
<211> LENGTH: 9
<212> TYPE: PRT
<213> ORGANISM: Homo sapiens

<400> SEQUENCE: 446

Tyr Gly Pro Asp Val Gly Gln Pro Arg
1               5

<210> SEQ ID NO 447
<211> LENGTH: 9
<212> TYPE: PRT
<213> ORGANISM: Homo sapiens

```
<400> SEQUENCE: 447

Arg Lys Thr Ala Lys Met Leu Lys Ser
1               5

<210> SEQ ID NO 448
<211> LENGTH: 9
<212> TYPE: PRT
<213> ORGANISM: Homo sapiens

<400> SEQUENCE: 448

Ile Asp Ser Val Thr Trp His His Tyr
1               5

<210> SEQ ID NO 449
<211> LENGTH: 9
<212> TYPE: PRT
<213> ORGANISM: Homo sapiens

<400> SEQUENCE: 449

Thr Ala Thr Arg Glu Asp Phe Leu Asn
1               5

<210> SEQ ID NO 450
<211> LENGTH: 9
<212> TYPE: PRT
<213> ORGANISM: Homo sapiens

<400> SEQUENCE: 450

Leu Asp Ile Phe Ile Ser Ser Val Gln
1               5

<210> SEQ ID NO 451
<211> LENGTH: 9
<212> TYPE: PRT
<213> ORGANISM: Homo sapiens

<400> SEQUENCE: 451

Val Gln Lys Val Phe Gln Val Val Glu
1               5

<210> SEQ ID NO 452
<211> LENGTH: 9
<212> TYPE: PRT
<213> ORGANISM: Homo sapiens

<400> SEQUENCE: 452

Val Phe Gln Val Val Glu Ser Thr Arg
1               5

<210> SEQ ID NO 453
<211> LENGTH: 9
<212> TYPE: PRT
<213> ORGANISM: Homo sapiens

<400> SEQUENCE: 453

Val Glu Ser Thr Arg Pro Gly Lys Lys
1               5

<210> SEQ ID NO 454
<211> LENGTH: 9
<212> TYPE: PRT
<213> ORGANISM: Homo sapiens

<400> SEQUENCE: 454
```

```
Leu Gly Glu Thr Ser Ser Ala Tyr Gly
1               5
```

<210> SEQ ID NO 455
<211> LENGTH: 9
<212> TYPE: PRT
<213> ORGANISM: Homo sapiens

<400> SEQUENCE: 455

```
Glu Val Val Met Arg Gln Val Phe Phe
1               5
```

<210> SEQ ID NO 456
<211> LENGTH: 9
<212> TYPE: PRT
<213> ORGANISM: Homo sapiens

<400> SEQUENCE: 456

```
Arg Gln Val Phe Phe Gly Ala Gly Asn
1               5
```

<210> SEQ ID NO 457
<211> LENGTH: 9
<212> TYPE: PRT
<213> ORGANISM: Homo sapiens

<400> SEQUENCE: 457

```
Asn Phe Asp Pro Leu Pro Asp Tyr Trp
1               5
```

<210> SEQ ID NO 458
<211> LENGTH: 9
<212> TYPE: PRT
<213> ORGANISM: Homo sapiens

<400> SEQUENCE: 458

```
Asp Pro Leu Pro Asp Tyr Trp Leu Ser
1               5
```

<210> SEQ ID NO 459
<211> LENGTH: 9
<212> TYPE: PRT
<213> ORGANISM: Homo sapiens

<400> SEQUENCE: 459

```
Ala Ser Val Gln Gly Ser Lys Arg Arg
1               5
```

<210> SEQ ID NO 460
<211> LENGTH: 9
<212> TYPE: PRT
<213> ORGANISM: Homo sapiens

<400> SEQUENCE: 460

```
Arg Lys Leu Arg Val Tyr Leu His Cys
1               5
```

<210> SEQ ID NO 461
<211> LENGTH: 9
<212> TYPE: PRT
<213> ORGANISM: Homo sapiens

<400> SEQUENCE: 461

```
Tyr Pro Phe Ser Asn Lys Gln Val Asp
```

```
<210> SEQ ID NO 462
<211> LENGTH: 9
<212> TYPE: PRT
<213> ORGANISM: Homo sapiens

<400> SEQUENCE: 462

Asn Gly Leu Thr Leu Lys Met Val Asp
1               5

<210> SEQ ID NO 463
<211> LENGTH: 9
<212> TYPE: PRT
<213> ORGANISM: Homo sapiens

<400> SEQUENCE: 463

Pro Gly Ser Ser Leu Gly Leu Pro Ala
1               5

<210> SEQ ID NO 464
<211> LENGTH: 9
<212> TYPE: PRT
<213> ORGANISM: Homo sapiens

<400> SEQUENCE: 464

Leu Pro Ala Phe Ser Tyr Ser Phe Phe
1               5

<210> SEQ ID NO 465
<211> LENGTH: 9
<212> TYPE: PRT
<213> ORGANISM: Homo sapiens

<400> SEQUENCE: 465

Pro Gly Ala Leu Pro Arg Pro Ala Gln
1               5

<210> SEQ ID NO 466
<211> LENGTH: 9
<212> TYPE: PRT
<213> ORGANISM: Homo sapiens

<400> SEQUENCE: 466

Pro Ser Phe Leu Ser Val Thr Ile Asp
1               5

<210> SEQ ID NO 467
<211> LENGTH: 9
<212> TYPE: PRT
<213> ORGANISM: Homo sapiens

<400> SEQUENCE: 467

Arg Phe Gly Gly Thr Lys Thr Asp Phe
1               5

<210> SEQ ID NO 468
<211> LENGTH: 9
<212> TYPE: PRT
<213> ORGANISM: Homo sapiens

<400> SEQUENCE: 468

Pro Lys Lys Glu Ser Thr Phe Glu Glu
1               5
```

```
<210> SEQ ID NO 469
<211> LENGTH: 9
<212> TYPE: PRT
<213> ORGANISM: Homo sapiens

<400> SEQUENCE: 469

Lys Lys Glu Ser Thr Phe Glu Glu Arg
1               5

<210> SEQ ID NO 470
<211> LENGTH: 9
<212> TYPE: PRT
<213> ORGANISM: Homo sapiens

<400> SEQUENCE: 470

Lys Glu Ser Thr Phe Glu Glu Arg Ser
1               5

<210> SEQ ID NO 471
<211> LENGTH: 9
<212> TYPE: PRT
<213> ORGANISM: Homo sapiens

<400> SEQUENCE: 471

Thr Phe Glu Glu Arg Ser Tyr Trp Gln
1               5

<210> SEQ ID NO 472
<211> LENGTH: 9
<212> TYPE: PRT
<213> ORGANISM: Homo sapiens

<400> SEQUENCE: 472

Ser Gln Val Asn Gln Asp Ile Cys Lys
1               5

<210> SEQ ID NO 473
<211> LENGTH: 9
<212> TYPE: PRT
<213> ORGANISM: Homo sapiens

<400> SEQUENCE: 473

Asn Gln Asp Ile Cys Lys Tyr Gly Ser
1               5

<210> SEQ ID NO 474
<211> LENGTH: 9
<212> TYPE: PRT
<213> ORGANISM: Homo sapiens

<400> SEQUENCE: 474

Ile Cys Lys Tyr Gly Ser Ile Pro Pro
1               5

<210> SEQ ID NO 475
<211> LENGTH: 9
<212> TYPE: PRT
<213> ORGANISM: Homo sapiens

<400> SEQUENCE: 475

Lys Lys Phe Lys Asn Ser Thr Tyr Ser
1               5

<210> SEQ ID NO 476
```

```
<211> LENGTH: 9
<212> TYPE: PRT
<213> ORGANISM: Homo sapiens

<400> SEQUENCE: 476

Phe Lys Asn Ser Thr Tyr Ser Arg Ser
1               5

<210> SEQ ID NO 477
<211> LENGTH: 9
<212> TYPE: PRT
<213> ORGANISM: Homo sapiens

<400> SEQUENCE: 477

Leu Tyr Thr Phe Ala Asn Cys Ser Gly
1               5

<210> SEQ ID NO 478
<211> LENGTH: 9
<212> TYPE: PRT
<213> ORGANISM: Homo sapiens

<400> SEQUENCE: 478

Thr Phe Ala Asn Cys Ser Gly Leu Asp
1               5

<210> SEQ ID NO 479
<211> LENGTH: 9
<212> TYPE: PRT
<213> ORGANISM: Homo sapiens

<400> SEQUENCE: 479

Gly Tyr Asn Ile Ser Trp Glu Leu Gly
1               5

<210> SEQ ID NO 480
<211> LENGTH: 9
<212> TYPE: PRT
<213> ORGANISM: Homo sapiens

<400> SEQUENCE: 480

Gly Asn Glu Pro Asn Ser Phe Leu Lys
1               5

<210> SEQ ID NO 481
<211> LENGTH: 9
<212> TYPE: PRT
<213> ORGANISM: Homo sapiens

<400> SEQUENCE: 481

Gly Gln Pro Arg Arg Lys Thr Ala Lys
1               5

<210> SEQ ID NO 482
<211> LENGTH: 9
<212> TYPE: PRT
<213> ORGANISM: Homo sapiens

<400> SEQUENCE: 482

Thr Trp His His Tyr Tyr Leu Asn Gly
1               5

<210> SEQ ID NO 483
<211> LENGTH: 9
<212> TYPE: PRT
```

<213> ORGANISM: Homo sapiens

<400> SEQUENCE: 483

Leu Asn Gly Arg Thr Ala Thr Arg Glu
1               5

<210> SEQ ID NO 484
<211> LENGTH: 9
<212> TYPE: PRT
<213> ORGANISM: Homo sapiens

<400> SEQUENCE: 484

Gly Glu Thr Ser Ser Ala Tyr Gly Gly
1               5

<210> SEQ ID NO 485
<211> LENGTH: 9
<212> TYPE: PRT
<213> ORGANISM: Homo sapiens

<400> SEQUENCE: 485

Glu Thr Ser Ser Ala Tyr Gly Gly Gly
1               5

<210> SEQ ID NO 486
<211> LENGTH: 9
<212> TYPE: PRT
<213> ORGANISM: Homo sapiens

<400> SEQUENCE: 486

Gly Phe Met Trp Leu Asp Lys Leu Gly
1               5

<210> SEQ ID NO 487
<211> LENGTH: 9
<212> TYPE: PRT
<213> ORGANISM: Homo sapiens

<400> SEQUENCE: 487

Ile Glu Val Val Met Arg Gln Val Phe
1               5

<210> SEQ ID NO 488
<211> LENGTH: 9
<212> TYPE: PRT
<213> ORGANISM: Homo sapiens

<400> SEQUENCE: 488

Met Arg Gln Val Phe Phe Gly Ala Gly
1               5

<210> SEQ ID NO 489
<211> LENGTH: 9
<212> TYPE: PRT
<213> ORGANISM: Homo sapiens

<400> SEQUENCE: 489

Val Asp Glu Asn Phe Asp Pro Leu Pro
1               5

<210> SEQ ID NO 490
<211> LENGTH: 9
<212> TYPE: PRT
<213> ORGANISM: Homo sapiens

```
<400> SEQUENCE: 490

Pro Arg Tyr Lys Glu Gly Asp Leu Thr
1               5

<210> SEQ ID NO 491
<211> LENGTH: 9
<212> TYPE: PRT
<213> ORGANISM: Homo sapiens

<400> SEQUENCE: 491

Asp Lys Tyr Leu Leu Arg Pro Leu Gly
1               5

<210> SEQ ID NO 492
<211> LENGTH: 9
<212> TYPE: PRT
<213> ORGANISM: Homo sapiens

<400> SEQUENCE: 492

His Gly Leu Leu Ser Lys Ser Val Gln
1               5

<210> SEQ ID NO 493
<211> LENGTH: 9
<212> TYPE: PRT
<213> ORGANISM: Homo sapiens

<400> SEQUENCE: 493

Leu Ser Lys Ser Val Gln Leu Asn Gly
1               5

<210> SEQ ID NO 494
<211> LENGTH: 9
<212> TYPE: PRT
<213> ORGANISM: Homo sapiens

<400> SEQUENCE: 494

Asp Phe Phe Thr Gln Glu Pro Leu His
1               5

<210> SEQ ID NO 495
<211> LENGTH: 9
<212> TYPE: PRT
<213> ORGANISM: Homo sapiens

<400> SEQUENCE: 495

Leu Arg Thr Leu Ala Arg Gly Leu Ser
1               5

<210> SEQ ID NO 496
<211> LENGTH: 9
<212> TYPE: PRT
<213> ORGANISM: Homo sapiens

<400> SEQUENCE: 496

Thr Asp Phe Leu Ile Phe Asp Pro Lys
1               5

<210> SEQ ID NO 497
<211> LENGTH: 9
<212> TYPE: PRT
<213> ORGANISM: Homo sapiens

<400> SEQUENCE: 497
```

-continued

```
Arg Ser Tyr Trp Gln Ser Gln Val Asn
1               5

<210> SEQ ID NO 498
<211> LENGTH: 9
<212> TYPE: PRT
<213> ORGANISM: Homo sapiens

<400> SEQUENCE: 498

Val Asn Gln Asp Ile Cys Lys Tyr Gly
1               5

<210> SEQ ID NO 499
<211> LENGTH: 9
<212> TYPE: PRT
<213> ORGANISM: Homo sapiens

<400> SEQUENCE: 499

Glu His Tyr Gln Lys Lys Phe Lys Asn
1               5

<210> SEQ ID NO 500
<211> LENGTH: 9
<212> TYPE: PRT
<213> ORGANISM: Homo sapiens

<400> SEQUENCE: 500

Gln Lys Lys Phe Lys Asn Ser Thr Tyr
1               5

<210> SEQ ID NO 501
<211> LENGTH: 9
<212> TYPE: PRT
<213> ORGANISM: Homo sapiens

<400> SEQUENCE: 501

Asn Gly Ser Gln Leu Gly Glu Asp Phe
1               5

<210> SEQ ID NO 502
<211> LENGTH: 9
<212> TYPE: PRT
<213> ORGANISM: Homo sapiens

<400> SEQUENCE: 502

Gly Glu Asp Phe Ile Gln Leu His Lys
1               5

<210> SEQ ID NO 503
<211> LENGTH: 9
<212> TYPE: PRT
<213> ORGANISM: Homo sapiens

<400> SEQUENCE: 503

Pro Asp Val Leu Asp Ile Phe Ile Ser
1               5

<210> SEQ ID NO 504
<211> LENGTH: 9
<212> TYPE: PRT
<213> ORGANISM: Homo sapiens

<400> SEQUENCE: 504

Phe Gln Val Val Glu Ser Thr Arg Pro
1               5
```

<210> SEQ ID NO 505
<211> LENGTH: 9
<212> TYPE: PRT
<213> ORGANISM: Homo sapiens

<400> SEQUENCE: 505

Asp Asn Pro Arg Tyr Lys Glu Gly Asp
1               5

<210> SEQ ID NO 506
<211> LENGTH: 15
<212> TYPE: PRT
<213> ORGANISM: Homo sapiens

<400> SEQUENCE: 506

Arg Gln Val Phe Phe Gly Ala Gly Asn Tyr His Leu Val Asp Glu
1               5                   10                  15

<210> SEQ ID NO 507
<211> LENGTH: 15
<212> TYPE: PRT
<213> ORGANISM: Homo sapiens

<400> SEQUENCE: 507

Ser Tyr Ser Phe Phe Val Ile Arg Asn Ala Lys Val Ala Ala Cys
1               5                   10                  15

<210> SEQ ID NO 508
<211> LENGTH: 15
<212> TYPE: PRT
<213> ORGANISM: Homo sapiens

<400> SEQUENCE: 508

Val Val Asp Leu Asp Phe Phe Thr Gln Glu Pro Leu His Leu Val
1               5                   10                  15

<210> SEQ ID NO 509
<211> LENGTH: 15
<212> TYPE: PRT
<213> ORGANISM: Homo sapiens

<400> SEQUENCE: 509

Phe Leu Ser Val Thr Ile Asp Ala Asn Leu Ala Thr Asp Pro Arg
1               5                   10                  15

<210> SEQ ID NO 510
<211> LENGTH: 15
<212> TYPE: PRT
<213> ORGANISM: Homo sapiens

<400> SEQUENCE: 510

Asp Ala Asn Leu Ala Thr Asp Pro Arg Phe Leu Ile Leu Leu Gly
1               5                   10                  15

<210> SEQ ID NO 511
<211> LENGTH: 15
<212> TYPE: PRT
<213> ORGANISM: Homo sapiens

<400> SEQUENCE: 511

Pro Arg Phe Leu Ile Leu Leu Gly Ser Pro Lys Leu Arg Thr Leu
1               5                   10                  15

```
<210> SEQ ID NO 512
<211> LENGTH: 15
<212> TYPE: PRT
<213> ORGANISM: Homo sapiens

<400> SEQUENCE: 512

Ser Pro Lys Leu Arg Thr Leu Ala Arg Gly Leu Ser Pro Ala Tyr
1               5                   10                  15

<210> SEQ ID NO 513
<211> LENGTH: 15
<212> TYPE: PRT
<213> ORGANISM: Homo sapiens

<400> SEQUENCE: 513

Arg Ser Ser Val Asp Val Leu Tyr Thr Phe Ala Asn Cys Ser Gly
1               5                   10                  15

<210> SEQ ID NO 514
<211> LENGTH: 15
<212> TYPE: PRT
<213> ORGANISM: Homo sapiens

<400> SEQUENCE: 514

Ser Trp Glu Leu Gly Asn Glu Pro Asn Ser Phe Leu Lys Lys Ala
1               5                   10                  15

<210> SEQ ID NO 515
<211> LENGTH: 15
<212> TYPE: PRT
<213> ORGANISM: Homo sapiens

<400> SEQUENCE: 515

Phe Ile Gln Leu His Lys Leu Leu Arg Lys Ser Thr Phe Lys Asn
1               5                   10                  15

<210> SEQ ID NO 516
<211> LENGTH: 15
<212> TYPE: PRT
<213> ORGANISM: Homo sapiens

<400> SEQUENCE: 516

Pro Asp Val Leu Asp Ile Phe Ile Ser Ser Val Gln Lys Val Phe
1               5                   10                  15

<210> SEQ ID NO 517
<211> LENGTH: 15
<212> TYPE: PRT
<213> ORGANISM: Homo sapiens

<400> SEQUENCE: 517

Leu Asp Phe Phe Thr Gln Glu Pro Leu His Leu Val Ser Pro Ser
1               5                   10                  15

<210> SEQ ID NO 518
<211> LENGTH: 15
<212> TYPE: PRT
<213> ORGANISM: Homo sapiens

<400> SEQUENCE: 518

Ser Pro Ser Phe Leu Ser Val Thr Ile Asp Ala Asn Leu Ala Thr
1               5                   10                  15

<210> SEQ ID NO 519
<211> LENGTH: 15
```

```
<212> TYPE: PRT
<213> ORGANISM: Homo sapiens

<400> SEQUENCE: 519

Asp Pro Arg Phe Leu Ile Leu Leu Gly Ser Pro Lys Leu Arg Thr
1               5                   10                  15

<210> SEQ ID NO 520
<211> LENGTH: 15
<212> TYPE: PRT
<213> ORGANISM: Homo sapiens

<400> SEQUENCE: 520

Ser Pro Ala Tyr Leu Arg Phe Gly Gly Thr Lys Thr Asp Phe Leu
1               5                   10                  15

<210> SEQ ID NO 521
<211> LENGTH: 15
<212> TYPE: PRT
<213> ORGANISM: Homo sapiens

<400> SEQUENCE: 521

Tyr Leu Arg Phe Gly Gly Thr Lys Thr Asp Phe Leu Ile Phe Asp
1               5                   10                  15

<210> SEQ ID NO 522
<211> LENGTH: 15
<212> TYPE: PRT
<213> ORGANISM: Homo sapiens

<400> SEQUENCE: 522

Arg Ser Tyr Trp Gln Ser Gln Val Asn Gln Asp Ile Cys Lys Tyr
1               5                   10                  15

<210> SEQ ID NO 523
<211> LENGTH: 15
<212> TYPE: PRT
<213> ORGANISM: Homo sapiens

<400> SEQUENCE: 523

Arg Leu Glu Trp Pro Tyr Gln Glu Gln Leu Leu Leu Arg Glu His
1               5                   10                  15

<210> SEQ ID NO 524
<211> LENGTH: 15
<212> TYPE: PRT
<213> ORGANISM: Homo sapiens

<400> SEQUENCE: 524

Asp Val Leu Tyr Thr Phe Ala Asn Cys Ser Gly Leu Asp Leu Ile
1               5                   10                  15

<210> SEQ ID NO 525
<211> LENGTH: 15
<212> TYPE: PRT
<213> ORGANISM: Homo sapiens

<400> SEQUENCE: 525

Leu Lys Ser Phe Leu Lys Ala Gly Gly Glu Val Ile Asp Ser Val
1               5                   10                  15

<210> SEQ ID NO 526
<211> LENGTH: 15
<212> TYPE: PRT
<213> ORGANISM: Homo sapiens
```

```
<400> SEQUENCE: 526

Trp His His Tyr Tyr Leu Asn Gly Arg Thr Ala Thr Arg Glu Asp
1               5                   10                  15

<210> SEQ ID NO 527
<211> LENGTH: 15
<212> TYPE: PRT
<213> ORGANISM: Homo sapiens

<400> SEQUENCE: 527

Gln Lys Val Phe Gln Val Val Glu Ser Thr Arg Pro Gly Lys Lys
1               5                   10                  15

<210> SEQ ID NO 528
<211> LENGTH: 15
<212> TYPE: PRT
<213> ORGANISM: Homo sapiens

<400> SEQUENCE: 528

Lys Lys Val Trp Leu Gly Glu Thr Ser Ser Ala Tyr Gly Gly Gly
1               5                   10                  15

<210> SEQ ID NO 529
<211> LENGTH: 15
<212> TYPE: PRT
<213> ORGANISM: Homo sapiens

<400> SEQUENCE: 529

Ala Ala Gly Phe Met Trp Leu Asp Lys Leu Gly Leu Ser Ala Arg
1               5                   10                  15

<210> SEQ ID NO 530
<211> LENGTH: 15
<212> TYPE: PRT
<213> ORGANISM: Homo sapiens

<400> SEQUENCE: 530

Asp Glu Asn Phe Asp Pro Leu Pro Asp Tyr Trp Leu Ser Leu Leu
1               5                   10                  15

<210> SEQ ID NO 531
<211> LENGTH: 15
<212> TYPE: PRT
<213> ORGANISM: Homo sapiens

<400> SEQUENCE: 531

Pro Asp Tyr Trp Leu Ser Leu Leu Phe Lys Lys Leu Val Gly Thr
1               5                   10                  15

<210> SEQ ID NO 532
<211> LENGTH: 15
<212> TYPE: PRT
<213> ORGANISM: Homo sapiens

<400> SEQUENCE: 532

Ser Leu Leu Phe Lys Lys Leu Val Gly Thr Lys Val Leu Met Ala
1               5                   10                  15

<210> SEQ ID NO 533
<211> LENGTH: 15
<212> TYPE: PRT
<213> ORGANISM: Homo sapiens

<400> SEQUENCE: 533
```

```
Leu Arg Val Tyr Leu His Cys Thr Asn Thr Asp Asn Pro Arg Tyr
1               5                   10                  15

<210> SEQ ID NO 534
<211> LENGTH: 15
<212> TYPE: PRT
<213> ORGANISM: Homo sapiens

<400> SEQUENCE: 534

Leu Thr Leu Tyr Ala Ile Asn Leu His Asn Val Thr Lys Tyr Leu
1               5                   10                  15

<210> SEQ ID NO 535
<211> LENGTH: 15
<212> TYPE: PRT
<213> ORGANISM: Homo sapiens

<400> SEQUENCE: 535

Val Thr Lys Tyr Leu Arg Leu Pro Tyr Pro Phe Ser Asn Lys Gln
1               5                   10                  15

<210> SEQ ID NO 536
<211> LENGTH: 15
<212> TYPE: PRT
<213> ORGANISM: Homo sapiens

<400> SEQUENCE: 536

Ala Phe Ser Tyr Ser Phe Phe Val Ile Arg Asn Ala Lys Val Ala
1               5                   10                  15

<210> SEQ ID NO 537
<211> LENGTH: 15
<212> TYPE: PRT
<213> ORGANISM: Homo sapiens

<400> SEQUENCE: 537

Pro Pro Pro Leu Met Leu Leu Leu Gly Pro Leu Gly Pro Leu
1               5                   10                  15

<210> SEQ ID NO 538
<211> LENGTH: 15
<212> TYPE: PRT
<213> ORGANISM: Homo sapiens

<400> SEQUENCE: 538

Leu Gly Pro Leu Gly Pro Leu Ser Pro Gly Ala Leu Pro Arg Pro
1               5                   10                  15

<210> SEQ ID NO 539
<211> LENGTH: 15
<212> TYPE: PRT
<213> ORGANISM: Homo sapiens

<400> SEQUENCE: 539

Ala Gln Asp Val Val Asp Leu Asp Phe Phe Thr Gln Glu Pro Leu
1               5                   10                  15

<210> SEQ ID NO 540
<211> LENGTH: 15
<212> TYPE: PRT
<213> ORGANISM: Homo sapiens

<400> SEQUENCE: 540

Gln Glu Pro Leu His Leu Val Ser Pro Ser Phe Leu Ser Val Thr
```

```
                 1               5              10              15
```

<210> SEQ ID NO 541
<211> LENGTH: 15
<212> TYPE: PRT
<213> ORGANISM: Homo sapiens

<400> SEQUENCE: 541

```
Thr Asp Phe Leu Ile Phe Asp Pro Lys Lys Glu Ser Thr Phe Glu
 1               5                  10                  15
```

<210> SEQ ID NO 542
<211> LENGTH: 15
<212> TYPE: PRT
<213> ORGANISM: Homo sapiens

<400> SEQUENCE: 542

```
Tyr Gly Ser Ile Pro Pro Asp Val Glu Glu Lys Leu Arg Leu Glu
 1               5                  10                  15
```

<210> SEQ ID NO 543
<211> LENGTH: 15
<212> TYPE: PRT
<213> ORGANISM: Homo sapiens

<400> SEQUENCE: 543

```
Lys Leu Arg Leu Glu Trp Pro Tyr Gln Glu Gln Leu Leu Leu Arg
 1               5                  10                  15
```

<210> SEQ ID NO 544
<211> LENGTH: 15
<212> TYPE: PRT
<213> ORGANISM: Homo sapiens

<400> SEQUENCE: 544

```
Glu Gln Leu Leu Leu Arg Glu His Tyr Gln Lys Lys Phe Lys Asn
 1               5                  10                  15
```

<210> SEQ ID NO 545
<211> LENGTH: 15
<212> TYPE: PRT
<213> ORGANISM: Homo sapiens

<400> SEQUENCE: 545

```
Val Asp Val Leu Tyr Thr Phe Ala Asn Cys Ser Gly Leu Asp Leu
 1               5                  10                  15
```

<210> SEQ ID NO 546
<211> LENGTH: 15
<212> TYPE: PRT
<213> ORGANISM: Homo sapiens

<400> SEQUENCE: 546

```
Cys Ser Gly Leu Asp Leu Ile Phe Gly Leu Asn Ala Leu Leu Arg
 1               5                  10                  15
```

<210> SEQ ID NO 547
<211> LENGTH: 15
<212> TYPE: PRT
<213> ORGANISM: Homo sapiens

<400> SEQUENCE: 547

```
Gly Leu Asp Leu Ile Phe Gly Leu Asn Ala Leu Leu Arg Thr Ala
 1               5                  10                  15
```

```
<210> SEQ ID NO 548
<211> LENGTH: 15
<212> TYPE: PRT
<213> ORGANISM: Homo sapiens

<400> SEQUENCE: 548

Ile Phe Gly Leu Asn Ala Leu Leu Arg Thr Ala Asp Leu Gln Trp
1               5                   10                  15

<210> SEQ ID NO 549
<211> LENGTH: 15
<212> TYPE: PRT
<213> ORGANISM: Homo sapiens

<400> SEQUENCE: 549

Asn Ala Leu Leu Arg Thr Ala Asp Leu Gln Trp Asn Ser Ser Asn
1               5                   10                  15

<210> SEQ ID NO 550
<211> LENGTH: 15
<212> TYPE: PRT
<213> ORGANISM: Homo sapiens

<400> SEQUENCE: 550

Thr Ala Asp Leu Gln Trp Asn Ser Ser Asn Ala Gln Leu Leu Leu
1               5                   10                  15

<210> SEQ ID NO 551
<211> LENGTH: 15
<212> TYPE: PRT
<213> ORGANISM: Homo sapiens

<400> SEQUENCE: 551

Asn Ala Gln Leu Leu Leu Asp Tyr Cys Ser Ser Lys Gly Tyr Asn
1               5                   10                  15

<210> SEQ ID NO 552
<211> LENGTH: 15
<212> TYPE: PRT
<213> ORGANISM: Homo sapiens

<400> SEQUENCE: 552

Asn Ser Phe Leu Lys Lys Ala Asp Ile Phe Ile Asn Gly Ser Gln
1               5                   10                  15

<210> SEQ ID NO 553
<211> LENGTH: 15
<212> TYPE: PRT
<213> ORGANISM: Homo sapiens

<400> SEQUENCE: 553

Gly Pro Asp Val Gly Gln Pro Arg Arg Lys Thr Ala Lys Met Leu
1               5                   10                  15

<210> SEQ ID NO 554
<211> LENGTH: 15
<212> TYPE: PRT
<213> ORGANISM: Homo sapiens

<400> SEQUENCE: 554

Asn Pro Asp Val Leu Asp Ile Phe Ile Ser Ser Val Gln Lys Val
1               5                   10                  15

<210> SEQ ID NO 555
```

```
<211> LENGTH: 15
<212> TYPE: PRT
<213> ORGANISM: Homo sapiens

<400> SEQUENCE: 555

Asp Ile Phe Ile Ser Ser Val Gln Lys Val Phe Gln Val Val Glu
1               5                   10                  15

<210> SEQ ID NO 556
<211> LENGTH: 15
<212> TYPE: PRT
<213> ORGANISM: Homo sapiens

<400> SEQUENCE: 556

Ile Ser Ser Val Gln Lys Val Phe Gln Val Val Glu Ser Thr Arg
1               5                   10                  15

<210> SEQ ID NO 557
<211> LENGTH: 15
<212> TYPE: PRT
<213> ORGANISM: Homo sapiens

<400> SEQUENCE: 557

Val Phe Gln Val Val Glu Ser Thr Arg Pro Gly Lys Lys Val Trp
1               5                   10                  15

<210> SEQ ID NO 558
<211> LENGTH: 15
<212> TYPE: PRT
<213> ORGANISM: Homo sapiens

<400> SEQUENCE: 558

Gly Lys Lys Val Trp Leu Gly Glu Thr Ser Ser Ala Tyr Gly Gly
1               5                   10                  15

<210> SEQ ID NO 559
<211> LENGTH: 15
<212> TYPE: PRT
<213> ORGANISM: Homo sapiens

<400> SEQUENCE: 559

Ala Gly Phe Met Trp Leu Asp Lys Leu Gly Leu Ser Ala Arg Met
1               5                   10                  15

<210> SEQ ID NO 560
<211> LENGTH: 15
<212> TYPE: PRT
<213> ORGANISM: Homo sapiens

<400> SEQUENCE: 560

Leu Asp Lys Leu Gly Leu Ser Ala Arg Met Gly Ile Glu Val Val
1               5                   10                  15

<210> SEQ ID NO 561
<211> LENGTH: 15
<212> TYPE: PRT
<213> ORGANISM: Homo sapiens

<400> SEQUENCE: 561

Ser Ala Arg Met Gly Ile Glu Val Val Met Arg Gln Val Phe Phe
1               5                   10                  15

<210> SEQ ID NO 562
<211> LENGTH: 15
<212> TYPE: PRT
```

<213> ORGANISM: Homo sapiens

<400> SEQUENCE: 562

Arg Met Gly Ile Glu Val Val Met Arg Gln Val Phe Phe Gly Ala
1               5                   10                  15

<210> SEQ ID NO 563
<211> LENGTH: 15
<212> TYPE: PRT
<213> ORGANISM: Homo sapiens

<400> SEQUENCE: 563

Asn Tyr His Leu Val Asp Glu Asn Phe Asp Pro Leu Pro Asp Tyr
1               5                   10                  15

<210> SEQ ID NO 564
<211> LENGTH: 15
<212> TYPE: PRT
<213> ORGANISM: Homo sapiens

<400> SEQUENCE: 564

Asp Tyr Trp Leu Ser Leu Leu Phe Lys Lys Leu Val Gly Thr Lys
1               5                   10                  15

<210> SEQ ID NO 565
<211> LENGTH: 15
<212> TYPE: PRT
<213> ORGANISM: Homo sapiens

<400> SEQUENCE: 565

Gly Thr Lys Val Leu Met Ala Ser Val Gln Gly Ser Lys Arg Arg
1               5                   10                  15

<210> SEQ ID NO 566
<211> LENGTH: 15
<212> TYPE: PRT
<213> ORGANISM: Homo sapiens

<400> SEQUENCE: 566

Thr Lys Val Leu Met Ala Ser Val Gln Gly Ser Lys Arg Arg Lys
1               5                   10                  15

<210> SEQ ID NO 567
<211> LENGTH: 15
<212> TYPE: PRT
<213> ORGANISM: Homo sapiens

<400> SEQUENCE: 567

Met Ala Ser Val Gln Gly Ser Lys Arg Arg Lys Leu Arg Val Tyr
1               5                   10                  15

<210> SEQ ID NO 568
<211> LENGTH: 15
<212> TYPE: PRT
<213> ORGANISM: Homo sapiens

<400> SEQUENCE: 568

Arg Arg Lys Leu Arg Val Tyr Leu His Cys Thr Asn Thr Asp Asn
1               5                   10                  15

<210> SEQ ID NO 569
<211> LENGTH: 15
<212> TYPE: PRT
<213> ORGANISM: Homo sapiens -continued

```
<400> SEQUENCE: 569

Asp Leu Thr Leu Tyr Ala Ile Asn Leu His Asn Val Thr Lys Tyr
1               5                   10                  15

<210> SEQ ID NO 570
<211> LENGTH: 15
<212> TYPE: PRT
<213> ORGANISM: Homo sapiens

<400> SEQUENCE: 570

Tyr Leu Arg Leu Pro Tyr Pro Phe Ser Asn Lys Gln Val Asp Lys
1               5                   10                  15

<210> SEQ ID NO 571
<211> LENGTH: 15
<212> TYPE: PRT
<213> ORGANISM: Homo sapiens

<400> SEQUENCE: 571

Lys Tyr Leu Leu Arg Pro Leu Gly Pro His Gly Leu Leu Ser Lys
1               5                   10                  15

<210> SEQ ID NO 572
<211> LENGTH: 15
<212> TYPE: PRT
<213> ORGANISM: Homo sapiens

<400> SEQUENCE: 572

Ser Val Gln Leu Asn Gly Leu Thr Leu Lys Met Val Asp Asp Gln
1               5                   10                  15

<210> SEQ ID NO 573
<211> LENGTH: 15
<212> TYPE: PRT
<213> ORGANISM: Homo sapiens

<400> SEQUENCE: 573

Gly Leu Thr Leu Lys Met Val Asp Asp Gln Thr Leu Pro Pro Leu
1               5                   10                  15

<210> SEQ ID NO 574
<211> LENGTH: 15
<212> TYPE: PRT
<213> ORGANISM: Homo sapiens

<400> SEQUENCE: 574

Thr Leu Lys Met Val Asp Asp Gln Thr Leu Pro Pro Leu Met Glu
1               5                   10                  15

<210> SEQ ID NO 575
<211> LENGTH: 15
<212> TYPE: PRT
<213> ORGANISM: Homo sapiens

<400> SEQUENCE: 575

Asp Gln Thr Leu Pro Pro Leu Met Glu Lys Pro Leu Arg Pro Gly
1               5                   10                  15

<210> SEQ ID NO 576
<211> LENGTH: 15
<212> TYPE: PRT
<213> ORGANISM: Homo sapiens

<400> SEQUENCE: 576
```

```
Pro Pro Leu Met Glu Lys Pro Leu Arg Pro Gly Ser Ser Leu Gly
1               5                   10                  15

<210> SEQ ID NO 577
<211> LENGTH: 15
<212> TYPE: PRT
<213> ORGANISM: Homo sapiens

<400> SEQUENCE: 577

Glu Lys Pro Leu Arg Pro Gly Ser Ser Leu Gly Leu Pro Ala Phe
1               5                   10                  15

<210> SEQ ID NO 578
<211> LENGTH: 15
<212> TYPE: PRT
<213> ORGANISM: Homo sapiens

<400> SEQUENCE: 578

Pro Leu Ser Pro Gly Ala Leu Pro Arg Pro Ala Gln Ala Gln Asp
1               5                   10                  15

<210> SEQ ID NO 579
<211> LENGTH: 15
<212> TYPE: PRT
<213> ORGANISM: Homo sapiens

<400> SEQUENCE: 579

His Leu Val Ser Pro Ser Phe Leu Ser Val Thr Ile Asp Ala Asn
1               5                   10                  15

<210> SEQ ID NO 580
<211> LENGTH: 15
<212> TYPE: PRT
<213> ORGANISM: Homo sapiens

<400> SEQUENCE: 580

Lys Glu Ser Thr Phe Glu Glu Arg Ser Tyr Trp Gln Ser Gln Val
1               5                   10                  15

<210> SEQ ID NO 581
<211> LENGTH: 15
<212> TYPE: PRT
<213> ORGANISM: Homo sapiens

<400> SEQUENCE: 581

Phe Gly Leu Asn Ala Leu Leu Arg Thr Ala Asp Leu Gln Trp Asn
1               5                   10                  15

<210> SEQ ID NO 582
<211> LENGTH: 15
<212> TYPE: PRT
<213> ORGANISM: Homo sapiens

<400> SEQUENCE: 582

Ala Leu Leu Arg Thr Ala Asp Leu Gln Trp Asn Ser Ser Asn Ala
1               5                   10                  15

<210> SEQ ID NO 583
<211> LENGTH: 15
<212> TYPE: PRT
<213> ORGANISM: Homo sapiens

<400> SEQUENCE: 583

Tyr Asn Ile Ser Trp Glu Leu Gly Asn Glu Pro Asn Ser Phe Leu
1               5                   10                  15
```

```
<210> SEQ ID NO 584
<211> LENGTH: 15
<212> TYPE: PRT
<213> ORGANISM: Homo sapiens

<400> SEQUENCE: 584

Leu Lys Lys Ala Asp Ile Phe Ile Asn Gly Ser Gln Leu Gly Glu
1               5                   10                  15

<210> SEQ ID NO 585
<211> LENGTH: 15
<212> TYPE: PRT
<213> ORGANISM: Homo sapiens

<400> SEQUENCE: 585

Ser Gln Leu Gly Glu Asp Phe Ile Gln Leu His Lys Leu Leu Arg
1               5                   10                  15

<210> SEQ ID NO 586
<211> LENGTH: 15
<212> TYPE: PRT
<213> ORGANISM: Homo sapiens

<400> SEQUENCE: 586

Leu Leu Arg Lys Ser Thr Phe Lys Asn Ala Lys Leu Tyr Gly Pro
1               5                   10                  15

<210> SEQ ID NO 587
<211> LENGTH: 15
<212> TYPE: PRT
<213> ORGANISM: Homo sapiens

<400> SEQUENCE: 587

Arg Lys Thr Ala Lys Met Leu Lys Ser Phe Leu Lys Ala Gly Gly
1               5                   10                  15

<210> SEQ ID NO 588
<211> LENGTH: 15
<212> TYPE: PRT
<213> ORGANISM: Homo sapiens

<400> SEQUENCE: 588

Thr Ala Thr Arg Glu Asp Phe Leu Asn Pro Asp Val Leu Asp Ile
1               5                   10                  15

<210> SEQ ID NO 589
<211> LENGTH: 15
<212> TYPE: PRT
<213> ORGANISM: Homo sapiens

<400> SEQUENCE: 589

Asp Val Leu Asp Ile Phe Ile Ser Ser Val Gln Lys Val Phe Gln
1               5                   10                  15

<210> SEQ ID NO 590
<211> LENGTH: 15
<212> TYPE: PRT
<213> ORGANISM: Homo sapiens

<400> SEQUENCE: 590

Leu Leu Phe Lys Lys Leu Val Gly Thr Lys Val Leu Met Ala Ser
1               5                   10                  15
```

```
<210> SEQ ID NO 591
<211> LENGTH: 15
<212> TYPE: PRT
<213> ORGANISM: Homo sapiens

<400> SEQUENCE: 591

Pro Arg Tyr Lys Glu Gly Asp Leu Thr Leu Tyr Ala Ile Asn Leu
1               5                   10                  15

<210> SEQ ID NO 592
<211> LENGTH: 15
<212> TYPE: PRT
<213> ORGANISM: Homo sapiens

<400> SEQUENCE: 592

Gly Asp Leu Thr Leu Tyr Ala Ile Asn Leu His Asn Val Thr Lys
1               5                   10                  15

<210> SEQ ID NO 593
<211> LENGTH: 15
<212> TYPE: PRT
<213> ORGANISM: Homo sapiens

<400> SEQUENCE: 593

Thr Leu Tyr Ala Ile Asn Leu His Asn Val Thr Lys Tyr Leu Arg
1               5                   10                  15

<210> SEQ ID NO 594
<211> LENGTH: 15
<212> TYPE: PRT
<213> ORGANISM: Homo sapiens

<400> SEQUENCE: 594

Leu Arg Leu Pro Tyr Pro Phe Ser Asn Lys Gln Val Asp Lys Tyr
1               5                   10                  15

<210> SEQ ID NO 595
<211> LENGTH: 15
<212> TYPE: PRT
<213> ORGANISM: Homo sapiens

<400> SEQUENCE: 595

Pro Leu Gly Pro His Gly Leu Leu Ser Lys Ser Val Gln Leu Asn
1               5                   10                  15

<210> SEQ ID NO 596
<211> LENGTH: 15
<212> TYPE: PRT
<213> ORGANISM: Homo sapiens

<400> SEQUENCE: 596

Phe Ser Tyr Ser Phe Phe Val Ile Arg Asn Ala Lys Val Ala Ala
1               5                   10                  15

<210> SEQ ID NO 597
<211> LENGTH: 15
<212> TYPE: PRT
<213> ORGANISM: Homo sapiens

<400> SEQUENCE: 597

Asp Leu Asp Phe Phe Thr Gln Glu Pro Leu His Leu Val Ser Pro
1               5                   10                  15

<210> SEQ ID NO 598
<211> LENGTH: 15
```

<210> SEQ ID NO 598
<211> LENGTH: 15
<212> TYPE: PRT
<213> ORGANISM: Homo sapiens

<400> SEQUENCE: 598

Lys Thr Asp Phe Leu Ile Phe Asp Pro Lys Lys Glu Ser Thr Phe
1               5                   10                  15

<210> SEQ ID NO 599
<211> LENGTH: 15
<212> TYPE: PRT
<213> ORGANISM: Homo sapiens

<400> SEQUENCE: 599

Ile Cys Lys Tyr Gly Ser Ile Pro Pro Asp Val Glu Glu Lys Leu
1               5                   10                  15

<210> SEQ ID NO 600
<211> LENGTH: 15
<212> TYPE: PRT
<213> ORGANISM: Homo sapiens

<400> SEQUENCE: 600

Gln Lys Lys Phe Lys Asn Ser Thr Tyr Ser Arg Ser Ser Val Asp
1               5                   10                  15

<210> SEQ ID NO 601
<211> LENGTH: 15
<212> TYPE: PRT
<213> ORGANISM: Homo sapiens

<400> SEQUENCE: 601

Asn Ser Thr Tyr Ser Arg Ser Ser Val Asp Val Leu Tyr Thr Phe
1               5                   10                  15

<210> SEQ ID NO 602
<211> LENGTH: 15
<212> TYPE: PRT
<213> ORGANISM: Homo sapiens

<400> SEQUENCE: 602

Leu Tyr Thr Phe Ala Asn Cys Ser Gly Leu Asp Leu Ile Phe Gly
1               5                   10                  15

<210> SEQ ID NO 603
<211> LENGTH: 15
<212> TYPE: PRT
<213> ORGANISM: Homo sapiens

<400> SEQUENCE: 603

Asp Leu Ile Phe Gly Leu Asn Ala Leu Leu Arg Thr Ala Asp Leu
1               5                   10                  15

<210> SEQ ID NO 604
<211> LENGTH: 15
<212> TYPE: PRT
<213> ORGANISM: Homo sapiens

<400> SEQUENCE: 604

Asp Leu Gln Trp Asn Ser Ser Asn Ala Gln Leu Leu Leu Asp Tyr
1               5                   10                  15

<210> SEQ ID NO 605
<211> LENGTH: 15
<212> TYPE: PRT
<213> ORGANISM: Homo sapiens

```
<400> SEQUENCE: 605

Leu Leu Asp Tyr Cys Ser Ser Lys Gly Tyr Asn Ile Ser Trp Glu
1               5                   10                  15

<210> SEQ ID NO 606
<211> LENGTH: 15
<212> TYPE: PRT
<213> ORGANISM: Homo sapiens

<400> SEQUENCE: 606

Ser Lys Gly Tyr Asn Ile Ser Trp Glu Leu Gly Asn Glu Pro Asn
1               5                   10                  15

<210> SEQ ID NO 607
<211> LENGTH: 15
<212> TYPE: PRT
<213> ORGANISM: Homo sapiens

<400> SEQUENCE: 607

Asn Ile Ser Trp Glu Leu Gly Asn Glu Pro Asn Ser Phe Leu Lys
1               5                   10                  15

<210> SEQ ID NO 608
<211> LENGTH: 15
<212> TYPE: PRT
<213> ORGANISM: Homo sapiens

<400> SEQUENCE: 608

Ala Asp Ile Phe Ile Asn Gly Ser Gln Leu Gly Glu Asp Phe Ile
1               5                   10                  15

<210> SEQ ID NO 609
<211> LENGTH: 15
<212> TYPE: PRT
<213> ORGANISM: Homo sapiens

<400> SEQUENCE: 609

Gly Glu Asp Phe Ile Gln Leu His Lys Leu Leu Arg Lys Ser Thr
1               5                   10                  15

<210> SEQ ID NO 610
<211> LENGTH: 15
<212> TYPE: PRT
<213> ORGANISM: Homo sapiens

<400> SEQUENCE: 610

Lys Ser Thr Phe Lys Asn Ala Lys Leu Tyr Gly Pro Asp Val Gly
1               5                   10                  15

<210> SEQ ID NO 611
<211> LENGTH: 15
<212> TYPE: PRT
<213> ORGANISM: Homo sapiens

<400> SEQUENCE: 611

Ala Lys Leu Tyr Gly Pro Asp Val Gly Gln Pro Arg Arg Lys Thr
1               5                   10                  15

<210> SEQ ID NO 612
<211> LENGTH: 15
<212> TYPE: PRT
<213> ORGANISM: Homo sapiens

<400> SEQUENCE: 612
```

His His Tyr Tyr Leu Asn Gly Arg Thr Ala Thr Arg Glu Asp Phe
1               5                   10                  15

<210> SEQ ID NO 613
<211> LENGTH: 15
<212> TYPE: PRT
<213> ORGANISM: Homo sapiens

<400> SEQUENCE: 613

Arg Glu Asp Phe Leu Asn Pro Asp Val Leu Asp Ile Phe Ile Ser
1               5                   10                  15

<210> SEQ ID NO 614
<211> LENGTH: 15
<212> TYPE: PRT
<213> ORGANISM: Homo sapiens

<400> SEQUENCE: 614

Leu Asp Ile Phe Ile Ser Ser Val Gln Lys Val Phe Gln Val Val
1               5                   10                  15

<210> SEQ ID NO 615
<211> LENGTH: 15
<212> TYPE: PRT
<213> ORGANISM: Homo sapiens

<400> SEQUENCE: 615

Ser Ser Ala Tyr Gly Gly Gly Ala Pro Leu Leu Ser Asp Thr Phe
1               5                   10                  15

<210> SEQ ID NO 616
<211> LENGTH: 15
<212> TYPE: PRT
<213> ORGANISM: Homo sapiens

<400> SEQUENCE: 616

Gln Val Phe Phe Gly Ala Gly Asn Tyr His Leu Val Asp Glu Asn
1               5                   10                  15

<210> SEQ ID NO 617
<211> LENGTH: 15
<212> TYPE: PRT
<213> ORGANISM: Homo sapiens

<400> SEQUENCE: 617

Ala Gly Asn Tyr His Leu Val Asp Glu Asn Phe Asp Pro Leu Pro
1               5                   10                  15

<210> SEQ ID NO 618
<211> LENGTH: 15
<212> TYPE: PRT
<213> ORGANISM: Homo sapiens

<400> SEQUENCE: 618

Leu Pro Asp Tyr Trp Leu Ser Leu Leu Phe Lys Lys Leu Val Gly
1               5                   10                  15

<210> SEQ ID NO 619
<211> LENGTH: 15
<212> TYPE: PRT
<213> ORGANISM: Homo sapiens

<400> SEQUENCE: 619

Gln Glu Gln Leu Leu Leu Arg Glu His Tyr Gln Lys Lys Phe Lys

```
                 1               5              10              15

<210> SEQ ID NO 620
<211> LENGTH: 15
<212> TYPE: PRT
<213> ORGANISM: Homo sapiens

<400> SEQUENCE: 620

Leu His Lys Leu Leu Arg Lys Ser Thr Phe Lys Asn Ala Lys Leu
1               5                  10                  15

<210> SEQ ID NO 621
<211> LENGTH: 15
<212> TYPE: PRT
<213> ORGANISM: Homo sapiens

<400> SEQUENCE: 621

Lys Pro Ala Leu Pro Pro Leu Met Leu Leu Leu Leu Gly Pro
1               5                  10                  15

<210> SEQ ID NO 622
<211> LENGTH: 15
<212> TYPE: PRT
<213> ORGANISM: Homo sapiens

<400> SEQUENCE: 622

Pro Pro Leu Met Leu Leu Leu Gly Pro Leu Gly Pro Leu Ser
1               5                  10                  15

<210> SEQ ID NO 623
<211> LENGTH: 15
<212> TYPE: PRT
<213> ORGANISM: Homo sapiens

<400> SEQUENCE: 623

Pro Leu Met Leu Leu Leu Gly Pro Leu Gly Pro Leu Ser Pro
1               5                  10                  15

<210> SEQ ID NO 624
<211> LENGTH: 15
<212> TYPE: PRT
<213> ORGANISM: Homo sapiens

<400> SEQUENCE: 624

Leu Met Leu Leu Leu Leu Gly Pro Leu Gly Pro Leu Ser Pro Gly
1               5                  10                  15

<210> SEQ ID NO 625
<211> LENGTH: 15
<212> TYPE: PRT
<213> ORGANISM: Homo sapiens

<400> SEQUENCE: 625

Met Leu Leu Leu Leu Gly Pro Leu Gly Pro Leu Ser Pro Gly Ala
1               5                  10                  15

<210> SEQ ID NO 626
<211> LENGTH: 15
<212> TYPE: PRT
<213> ORGANISM: Homo sapiens

<400> SEQUENCE: 626

Leu Leu Leu Leu Gly Pro Leu Gly Pro Leu Ser Pro Gly Ala Leu
1               5                  10                  15
```

```
<210> SEQ ID NO 627
<211> LENGTH: 15
<212> TYPE: PRT
<213> ORGANISM: Homo sapiens

<400> SEQUENCE: 627

Pro Gly Ala Leu Pro Arg Pro Ala Gln Ala Gln Asp Val Val Asp
1               5                   10                  15

<210> SEQ ID NO 628
<211> LENGTH: 15
<212> TYPE: PRT
<213> ORGANISM: Homo sapiens

<400> SEQUENCE: 628

Gln Asp Val Val Asp Leu Asp Phe Phe Thr Gln Glu Pro Leu His
1               5                   10                  15

<210> SEQ ID NO 629
<211> LENGTH: 15
<212> TYPE: PRT
<213> ORGANISM: Homo sapiens

<400> SEQUENCE: 629

Pro Leu His Leu Val Ser Pro Ser Phe Leu Ser Val Thr Ile Asp
1               5                   10                  15

<210> SEQ ID NO 630
<211> LENGTH: 15
<212> TYPE: PRT
<213> ORGANISM: Homo sapiens

<400> SEQUENCE: 630

Leu His Leu Val Ser Pro Ser Phe Leu Ser Val Thr Ile Asp Ala
1               5                   10                  15

<210> SEQ ID NO 631
<211> LENGTH: 15
<212> TYPE: PRT
<213> ORGANISM: Homo sapiens

<400> SEQUENCE: 631

Pro Ser Phe Leu Ser Val Thr Ile Asp Ala Asn Leu Ala Thr Asp
1               5                   10                  15

<210> SEQ ID NO 632
<211> LENGTH: 15
<212> TYPE: PRT
<213> ORGANISM: Homo sapiens

<400> SEQUENCE: 632

Phe Leu Ile Leu Leu Gly Ser Pro Lys Leu Arg Thr Leu Ala Arg
1               5                   10                  15

<210> SEQ ID NO 633
<211> LENGTH: 15
<212> TYPE: PRT
<213> ORGANISM: Homo sapiens

<400> SEQUENCE: 633

Leu Ile Leu Leu Gly Ser Pro Lys Leu Arg Thr Leu Ala Arg Gly
1               5                   10                  15

<210> SEQ ID NO 634
```

-continued

```
<211> LENGTH: 15
<212> TYPE: PRT
<213> ORGANISM: Homo sapiens

<400> SEQUENCE: 634

Leu Arg Thr Leu Ala Arg Gly Leu Ser Pro Ala Tyr Leu Arg Phe
1               5                   10                  15

<210> SEQ ID NO 635
<211> LENGTH: 15
<212> TYPE: PRT
<213> ORGANISM: Homo sapiens

<400> SEQUENCE: 635

Ala Arg Gly Leu Ser Pro Ala Tyr Leu Arg Phe Gly Gly Thr Lys
1               5                   10                  15

<210> SEQ ID NO 636
<211> LENGTH: 15
<212> TYPE: PRT
<213> ORGANISM: Homo sapiens

<400> SEQUENCE: 636

Pro Ala Tyr Leu Arg Phe Gly Gly Thr Lys Thr Asp Phe Leu Ile
1               5                   10                  15

<210> SEQ ID NO 637
<211> LENGTH: 15
<212> TYPE: PRT
<213> ORGANISM: Homo sapiens

<400> SEQUENCE: 637

Asp Phe Leu Ile Phe Asp Pro Lys Lys Glu Ser Thr Phe Glu Glu
1               5                   10                  15

<210> SEQ ID NO 638
<211> LENGTH: 15
<212> TYPE: PRT
<213> ORGANISM: Homo sapiens

<400> SEQUENCE: 638

Gln Ser Gln Val Asn Gln Asp Ile Cys Lys Tyr Gly Ser Ile Pro
1               5                   10                  15

<210> SEQ ID NO 639
<211> LENGTH: 15
<212> TYPE: PRT
<213> ORGANISM: Homo sapiens

<400> SEQUENCE: 639

Asn Gln Asp Ile Cys Lys Tyr Gly Ser Ile Pro Pro Asp Val Glu
1               5                   10                  15

<210> SEQ ID NO 640
<211> LENGTH: 15
<212> TYPE: PRT
<213> ORGANISM: Homo sapiens

<400> SEQUENCE: 640

Glu Glu Lys Leu Arg Leu Glu Trp Pro Tyr Gln Glu Gln Leu Leu
1               5                   10                  15

<210> SEQ ID NO 641
<211> LENGTH: 15
<212> TYPE: PRT
```

-continued

<213> ORGANISM: Homo sapiens

<400> SEQUENCE: 641

Gln Leu Leu Leu Arg Glu His Tyr Gln Lys Lys Phe Lys Asn Ser
1               5                   10                  15

<210> SEQ ID NO 642
<211> LENGTH: 15
<212> TYPE: PRT
<213> ORGANISM: Homo sapiens

<400> SEQUENCE: 642

Ser Val Asp Val Leu Tyr Thr Phe Ala Asn Cys Ser Gly Leu Asp
1               5                   10                  15

<210> SEQ ID NO 643
<211> LENGTH: 15
<212> TYPE: PRT
<213> ORGANISM: Homo sapiens

<400> SEQUENCE: 643

Leu Asp Leu Ile Phe Gly Leu Asn Ala Leu Leu Arg Thr Ala Asp
1               5                   10                  15

<210> SEQ ID NO 644
<211> LENGTH: 15
<212> TYPE: PRT
<213> ORGANISM: Homo sapiens

<400> SEQUENCE: 644

Ala Gln Leu Leu Leu Asp Tyr Cys Ser Ser Lys Gly Tyr Asn Ile
1               5                   10                  15

<210> SEQ ID NO 645
<211> LENGTH: 15
<212> TYPE: PRT
<213> ORGANISM: Homo sapiens

<400> SEQUENCE: 645

Gln Leu Leu Leu Asp Tyr Cys Ser Ser Lys Gly Tyr Asn Ile Ser
1               5                   10                  15

<210> SEQ ID NO 646
<211> LENGTH: 15
<212> TYPE: PRT
<213> ORGANISM: Homo sapiens

<400> SEQUENCE: 646

Gly Tyr Asn Ile Ser Trp Glu Leu Gly Asn Glu Pro Asn Ser Phe
1               5                   10                  15

<210> SEQ ID NO 647
<211> LENGTH: 15
<212> TYPE: PRT
<213> ORGANISM: Homo sapiens

<400> SEQUENCE: 647

Lys Ala Asp Ile Phe Ile Asn Gly Ser Gln Leu Gly Glu Asp Phe
1               5                   10                  15

<210> SEQ ID NO 648
<211> LENGTH: 15
<212> TYPE: PRT

```
<400> SEQUENCE: 648

Gly Ser Gln Leu Gly Glu Asp Phe Ile Gln Leu His Lys Leu Leu
1               5                   10                  15

<210> SEQ ID NO 649
<211> LENGTH: 15
<212> TYPE: PRT
<213> ORGANISM: Homo sapiens

<400> SEQUENCE: 649

Glu Asp Phe Ile Gln Leu His Lys Leu Leu Arg Lys Ser Thr Phe
1               5                   10                  15

<210> SEQ ID NO 650
<211> LENGTH: 15
<212> TYPE: PRT
<213> ORGANISM: Homo sapiens

<400> SEQUENCE: 650

His Lys Leu Leu Arg Lys Ser Thr Phe Lys Asn Ala Lys Leu Tyr
1               5                   10                  15

<210> SEQ ID NO 651
<211> LENGTH: 15
<212> TYPE: PRT
<213> ORGANISM: Homo sapiens

<400> SEQUENCE: 651

Ala Lys Met Leu Lys Ser Phe Leu Lys Ala Gly Gly Glu Val Ile
1               5                   10                  15

<210> SEQ ID NO 652
<211> LENGTH: 15
<212> TYPE: PRT
<213> ORGANISM: Homo sapiens

<400> SEQUENCE: 652

Gly Gly Glu Val Ile Asp Ser Val Thr Trp His His Tyr Tyr Leu
1               5                   10                  15

<210> SEQ ID NO 653
<211> LENGTH: 15
<212> TYPE: PRT
<213> ORGANISM: Homo sapiens

<400> SEQUENCE: 653

Gly Glu Val Ile Asp Ser Val Thr Trp His His Tyr Tyr Leu Asn
1               5                   10                  15

<210> SEQ ID NO 654
<211> LENGTH: 15
<212> TYPE: PRT
<213> ORGANISM: Homo sapiens

<400> SEQUENCE: 654

Ile Asp Ser Val Thr Trp His His Tyr Tyr Leu Asn Gly Arg Thr
1               5                   10                  15

<210> SEQ ID NO 655
<211> LENGTH: 15
<212> TYPE: PRT
<213> ORGANISM: Homo sapiens

<400> SEQUENCE: 655
```

-continued

Glu Asp Phe Leu Asn Pro Asp Val Leu Asp Ile Phe Ile Ser Ser
1               5                   10                  15

<210> SEQ ID NO 656
<211> LENGTH: 15
<212> TYPE: PRT
<213> ORGANISM: Homo sapiens

<400> SEQUENCE: 656

Val Leu Asp Ile Phe Ile Ser Ser Val Gln Lys Val Phe Gln Val
1               5                   10                  15

<210> SEQ ID NO 657
<211> LENGTH: 15
<212> TYPE: PRT
<213> ORGANISM: Homo sapiens

<400> SEQUENCE: 657

Val Gln Lys Val Phe Gln Val Val Glu Ser Thr Arg Pro Gly Lys
1               5                   10                  15

<210> SEQ ID NO 658
<211> LENGTH: 15
<212> TYPE: PRT
<213> ORGANISM: Homo sapiens

<400> SEQUENCE: 658

Phe Gln Val Val Glu Ser Thr Arg Pro Gly Lys Lys Val Trp Leu
1               5                   10                  15

<210> SEQ ID NO 659
<211> LENGTH: 15
<212> TYPE: PRT
<213> ORGANISM: Homo sapiens

<400> SEQUENCE: 659

Lys Val Trp Leu Gly Glu Thr Ser Ser Ala Tyr Gly Gly Gly Ala
1               5                   10                  15

<210> SEQ ID NO 660
<211> LENGTH: 15
<212> TYPE: PRT
<213> ORGANISM: Homo sapiens

<400> SEQUENCE: 660

Gly Ala Pro Leu Leu Ser Asp Thr Phe Ala Ala Gly Phe Met Trp
1               5                   10                  15

<210> SEQ ID NO 661
<211> LENGTH: 15
<212> TYPE: PRT
<213> ORGANISM: Homo sapiens

<400> SEQUENCE: 661

Phe Met Trp Leu Asp Lys Leu Gly Leu Ser Ala Arg Met Gly Ile
1               5                   10                  15

<210> SEQ ID NO 662
<211> LENGTH: 15
<212> TYPE: PRT
<213> ORGANISM: Homo sapiens

<400> SEQUENCE: 662

Ile Glu Val Val Met Arg Gln Val Phe Phe Gly Ala Gly Asn Tyr
1               5                   10                  15

<210> SEQ ID NO 663
<211> LENGTH: 15
<212> TYPE: PRT
<213> ORGANISM: Homo sapiens

<400> SEQUENCE: 663

Glu Val Val Met Arg Gln Val Phe Phe Gly Ala Gly Asn Tyr His
1               5                   10                  15

<210> SEQ ID NO 664
<211> LENGTH: 15
<212> TYPE: PRT
<213> ORGANISM: Homo sapiens

<400> SEQUENCE: 664

Phe Asp Pro Leu Pro Asp Tyr Trp Leu Ser Leu Leu Phe Lys Lys
1               5                   10                  15

<210> SEQ ID NO 665
<211> LENGTH: 15
<212> TYPE: PRT
<213> ORGANISM: Homo sapiens

<400> SEQUENCE: 665

Phe Lys Lys Leu Val Gly Thr Lys Val Leu Met Ala Ser Val Gln
1               5                   10                  15

<210> SEQ ID NO 666
<211> LENGTH: 15
<212> TYPE: PRT
<213> ORGANISM: Homo sapiens

<400> SEQUENCE: 666

Lys Val Leu Met Ala Ser Val Gln Gly Ser Lys Arg Arg Lys Leu
1               5                   10                  15

<210> SEQ ID NO 667
<211> LENGTH: 15
<212> TYPE: PRT
<213> ORGANISM: Homo sapiens

<400> SEQUENCE: 667

Lys Leu Arg Val Tyr Leu His Cys Thr Asn Thr Asp Asn Pro Arg
1               5                   10                  15

<210> SEQ ID NO 668
<211> LENGTH: 15
<212> TYPE: PRT
<213> ORGANISM: Homo sapiens

<400> SEQUENCE: 668

Arg Val Tyr Leu His Cys Thr Asn Thr Asp Asn Pro Arg Tyr Lys
1               5                   10                  15

<210> SEQ ID NO 669
<211> LENGTH: 15
<212> TYPE: PRT
<213> ORGANISM: Homo sapiens

<400> SEQUENCE: 669

Ala Ile Asn Leu His Asn Val Thr Lys Tyr Leu Arg Leu Pro Tyr
1               5                   10                  15

<210> SEQ ID NO 670
<211> LENGTH: 15
<212> TYPE: PRT
<213> ORGANISM: Homo sapiens

<400> SEQUENCE: 670

Leu His Asn Val Thr Lys Tyr Leu Arg Leu Pro Tyr Pro Phe Ser
1               5                   10                  15

<210> SEQ ID NO 671
<211> LENGTH: 15
<212> TYPE: PRT
<213> ORGANISM: Homo sapiens

<400> SEQUENCE: 671

Thr Lys Tyr Leu Arg Leu Pro Tyr Pro Phe Ser Asn Lys Gln Val
1               5                   10                  15

<210> SEQ ID NO 672
<211> LENGTH: 15
<212> TYPE: PRT
<213> ORGANISM: Homo sapiens

<400> SEQUENCE: 672

Asn Lys Gln Val Asp Lys Tyr Leu Leu Arg Pro Leu Gly Pro His
1               5                   10                  15

<210> SEQ ID NO 673
<211> LENGTH: 15
<212> TYPE: PRT
<213> ORGANISM: Homo sapiens

<400> SEQUENCE: 673

Leu Arg Pro Leu Gly Pro His Gly Leu Leu Ser Lys Ser Val Gln
1               5                   10                  15

<210> SEQ ID NO 674
<211> LENGTH: 15
<212> TYPE: PRT
<213> ORGANISM: Homo sapiens

<400> SEQUENCE: 674

His Gly Leu Leu Ser Lys Ser Val Gln Leu Asn Gly Leu Thr Leu
1               5                   10                  15

<210> SEQ ID NO 675
<211> LENGTH: 15
<212> TYPE: PRT
<213> ORGANISM: Homo sapiens

<400> SEQUENCE: 675

Ser Lys Ser Val Gln Leu Asn Gly Leu Thr Leu Lys Met Val Asp
1               5                   10                  15

<210> SEQ ID NO 676
<211> LENGTH: 15
<212> TYPE: PRT
<213> ORGANISM: Homo sapiens

<400> SEQUENCE: 676

Leu Lys Met Val Asp Asp Gln Thr Leu Pro Pro Leu Met Glu Lys
1               5                   10                  15

<210> SEQ ID NO 677
<211> LENGTH: 15

```
<212> TYPE: PRT
<213> ORGANISM: Homo sapiens

<400> SEQUENCE: 677

Gly Ser Ser Leu Gly Leu Pro Ala Phe Ser Tyr Ser Phe Phe Val
1               5                   10                  15

<210> SEQ ID NO 678
<211> LENGTH: 15
<212> TYPE: PRT
<213> ORGANISM: Homo sapiens

<400> SEQUENCE: 678

Ser Leu Gly Leu Pro Ala Phe Ser Tyr Ser Phe Phe Val Ile Arg
1               5                   10                  15

<210> SEQ ID NO 679
<211> LENGTH: 15
<212> TYPE: PRT
<213> ORGANISM: Homo sapiens

<400> SEQUENCE: 679

Leu Leu Arg Ser Lys Pro Ala Leu Pro Pro Leu Met Leu Leu Leu
1               5                   10                  15

<210> SEQ ID NO 680
<211> LENGTH: 15
<212> TYPE: PRT
<213> ORGANISM: Homo sapiens

<400> SEQUENCE: 680

Leu Arg Ser Lys Pro Ala Leu Pro Pro Leu Met Leu Leu Leu Leu
1               5                   10                  15

<210> SEQ ID NO 681
<211> LENGTH: 15
<212> TYPE: PRT
<213> ORGANISM: Homo sapiens

<400> SEQUENCE: 681

Pro Ala Leu Pro Pro Leu Met Leu Leu Leu Leu Gly Pro Leu
1               5                   10                  15

<210> SEQ ID NO 682
<211> LENGTH: 15
<212> TYPE: PRT
<213> ORGANISM: Homo sapiens

<400> SEQUENCE: 682

Leu Leu Gly Pro Leu Gly Pro Leu Ser Pro Gly Ala Leu Pro Arg
1               5                   10                  15

<210> SEQ ID NO 683
<211> LENGTH: 15
<212> TYPE: PRT
<213> ORGANISM: Homo sapiens

<400> SEQUENCE: 683

Gly Pro Leu Ser Pro Gly Ala Leu Pro Arg Pro Ala Gln Ala Gln
1               5                   10                  15

<210> SEQ ID NO 684
<211> LENGTH: 15
<212> TYPE: PRT
```

<400> SEQUENCE: 684

Gly Ala Leu Pro Arg Pro Ala Gln Ala Gln Asp Val Val Asp Leu
1               5                   10                  15

<210> SEQ ID NO 685
<211> LENGTH: 15
<212> TYPE: PRT
<213> ORGANISM: Homo sapiens

<400> SEQUENCE: 685

Ala Leu Pro Arg Pro Ala Gln Ala Gln Asp Val Val Asp Leu Asp
1               5                   10                  15

<210> SEQ ID NO 686
<211> LENGTH: 15
<212> TYPE: PRT
<213> ORGANISM: Homo sapiens

<400> SEQUENCE: 686

Gln Ala Gln Asp Val Val Asp Leu Asp Phe Phe Thr Gln Glu Pro
1               5                   10                  15

<210> SEQ ID NO 687
<211> LENGTH: 15
<212> TYPE: PRT
<213> ORGANISM: Homo sapiens

<400> SEQUENCE: 687

Asp Val Val Asp Leu Asp Phe Phe Thr Gln Glu Pro Leu His Leu
1               5                   10                  15

<210> SEQ ID NO 688
<211> LENGTH: 15
<212> TYPE: PRT
<213> ORGANISM: Homo sapiens

<400> SEQUENCE: 688

Asp Phe Phe Thr Gln Glu Pro Leu His Leu Val Ser Pro Ser Phe
1               5                   10                  15

<210> SEQ ID NO 689
<211> LENGTH: 15
<212> TYPE: PRT
<213> ORGANISM: Homo sapiens

<400> SEQUENCE: 689

Thr Gln Glu Pro Leu His Leu Val Ser Pro Ser Phe Leu Ser Val
1               5                   10                  15

<210> SEQ ID NO 690
<211> LENGTH: 15
<212> TYPE: PRT
<213> ORGANISM: Homo sapiens

<400> SEQUENCE: 690

Glu Pro Leu His Leu Val Ser Pro Ser Phe Leu Ser Val Thr Ile
1               5                   10                  15

<210> SEQ ID NO 691
<211> LENGTH: 15
<212> TYPE: PRT
<213> ORGANISM: Homo sapiens

<400> SEQUENCE: 691

```
Val Ser Pro Ser Phe Leu Ser Val Thr Ile Asp Ala Asn Leu Ala
1               5                   10                  15

<210> SEQ ID NO 692
<211> LENGTH: 15
<212> TYPE: PRT
<213> ORGANISM: Homo sapiens

<400> SEQUENCE: 692

Ser Phe Leu Ser Val Thr Ile Asp Ala Asn Leu Ala Thr Asp Pro
1               5                   10                  15

<210> SEQ ID NO 693
<211> LENGTH: 15
<212> TYPE: PRT
<213> ORGANISM: Homo sapiens

<400> SEQUENCE: 693

Val Thr Ile Asp Ala Asn Leu Ala Thr Asp Pro Arg Phe Leu Ile
1               5                   10                  15

<210> SEQ ID NO 694
<211> LENGTH: 15
<212> TYPE: PRT
<213> ORGANISM: Homo sapiens

<400> SEQUENCE: 694

Ala Thr Asp Pro Arg Phe Leu Ile Leu Leu Gly Ser Pro Lys Leu
1               5                   10                  15

<210> SEQ ID NO 695
<211> LENGTH: 15
<212> TYPE: PRT
<213> ORGANISM: Homo sapiens

<400> SEQUENCE: 695

Leu Leu Gly Ser Pro Lys Leu Arg Thr Leu Ala Arg Gly Leu Ser
1               5                   10                  15

<210> SEQ ID NO 696
<211> LENGTH: 15
<212> TYPE: PRT
<213> ORGANISM: Homo sapiens

<400> SEQUENCE: 696

Arg Thr Leu Ala Arg Gly Leu Ser Pro Ala Tyr Leu Arg Phe Gly
1               5                   10                  15

<210> SEQ ID NO 697
<211> LENGTH: 15
<212> TYPE: PRT
<213> ORGANISM: Homo sapiens

<400> SEQUENCE: 697

Gly Leu Ser Pro Ala Tyr Leu Arg Phe Gly Gly Thr Lys Thr Asp
1               5                   10                  15

<210> SEQ ID NO 698
<211> LENGTH: 15
<212> TYPE: PRT
<213> ORGANISM: Homo sapiens

<400> SEQUENCE: 698

Gly Thr Lys Thr Asp Phe Leu Ile Phe Asp Pro Lys Lys Glu Ser
```

-continued

```
                1               5                  10                 15
```

<210> SEQ ID NO 699
<211> LENGTH: 15
<212> TYPE: PRT
<213> ORGANISM: Homo sapiens

<400> SEQUENCE: 699

```
Thr Lys Thr Asp Phe Leu Ile Phe Asp Pro Lys Lys Glu Ser Thr
1               5                  10                 15
```

<210> SEQ ID NO 700
<211> LENGTH: 15
<212> TYPE: PRT
<213> ORGANISM: Homo sapiens

<400> SEQUENCE: 700

```
Ile Phe Asp Pro Lys Lys Glu Ser Thr Phe Glu Glu Arg Ser Tyr
1               5                  10                 15
```

<210> SEQ ID NO 701
<211> LENGTH: 15
<212> TYPE: PRT
<213> ORGANISM: Homo sapiens

<400> SEQUENCE: 701

```
Lys Lys Glu Ser Thr Phe Glu Glu Arg Ser Tyr Trp Gln Ser Gln
1               5                  10                 15
```

<210> SEQ ID NO 702
<211> LENGTH: 15
<212> TYPE: PRT
<213> ORGANISM: Homo sapiens

<400> SEQUENCE: 702

```
Thr Phe Glu Glu Arg Ser Tyr Trp Gln Ser Gln Val Asn Gln Asp
1               5                  10                 15
```

<210> SEQ ID NO 703
<211> LENGTH: 15
<212> TYPE: PRT
<213> ORGANISM: Homo sapiens

<400> SEQUENCE: 703

```
Phe Glu Glu Arg Ser Tyr Trp Gln Ser Gln Val Asn Gln Asp Ile
1               5                  10                 15
```

<210> SEQ ID NO 704
<211> LENGTH: 15
<212> TYPE: PRT
<213> ORGANISM: Homo sapiens

<400> SEQUENCE: 704

```
Glu Glu Arg Ser Tyr Trp Gln Ser Gln Val Asn Gln Asp Ile Cys
1               5                  10                 15
```

<210> SEQ ID NO 705
<211> LENGTH: 15
<212> TYPE: PRT
<213> ORGANISM: Homo sapiens

<400> SEQUENCE: 705

```
Ser Tyr Trp Gln Ser Gln Val Asn Gln Asp Ile Cys Lys Tyr Gly
1               5                  10                 15
```

```
<210> SEQ ID NO 706
<211> LENGTH: 15
<212> TYPE: PRT
<213> ORGANISM: Homo sapiens

<400> SEQUENCE: 706

Ser Gln Val Asn Gln Asp Ile Cys Lys Tyr Gly Ser Ile Pro Pro
1               5                   10                  15

<210> SEQ ID NO 707
<211> LENGTH: 15
<212> TYPE: PRT
<213> ORGANISM: Homo sapiens

<400> SEQUENCE: 707

Ser Ile Pro Pro Asp Val Glu Glu Lys Leu Arg Leu Glu Trp Pro
1               5                   10                  15

<210> SEQ ID NO 708
<211> LENGTH: 15
<212> TYPE: PRT
<213> ORGANISM: Homo sapiens

<400> SEQUENCE: 708

Val Glu Glu Lys Leu Arg Leu Glu Trp Pro Tyr Gln Glu Gln Leu
1               5                   10                  15

<210> SEQ ID NO 709
<211> LENGTH: 15
<212> TYPE: PRT
<213> ORGANISM: Homo sapiens

<400> SEQUENCE: 709

Pro Tyr Gln Glu Gln Leu Leu Leu Arg Glu His Tyr Gln Lys Lys
1               5                   10                  15

<210> SEQ ID NO 710
<211> LENGTH: 15
<212> TYPE: PRT
<213> ORGANISM: Homo sapiens

<400> SEQUENCE: 710

Tyr Gln Glu Gln Leu Leu Leu Arg Glu His Tyr Gln Lys Lys Phe
1               5                   10                  15

<210> SEQ ID NO 711
<211> LENGTH: 15
<212> TYPE: PRT
<213> ORGANISM: Homo sapiens

<400> SEQUENCE: 711

Glu His Tyr Gln Lys Lys Phe Lys Asn Ser Thr Tyr Ser Arg Ser
1               5                   10                  15

<210> SEQ ID NO 712
<211> LENGTH: 15
<212> TYPE: PRT
<213> ORGANISM: Homo sapiens

<400> SEQUENCE: 712

Lys Lys Phe Lys Asn Ser Thr Tyr Ser Arg Ser Ser Val Asp Val
1               5                   10                  15

<210> SEQ ID NO 713
```

```
<211> LENGTH: 15
<212> TYPE: PRT
<213> ORGANISM: Homo sapiens

<400> SEQUENCE: 713

Lys Phe Lys Asn Ser Thr Tyr Ser Arg Ser Ser Val Asp Val Leu
1               5                   10                  15

<210> SEQ ID NO 714
<211> LENGTH: 15
<212> TYPE: PRT
<213> ORGANISM: Homo sapiens

<400> SEQUENCE: 714

Thr Tyr Ser Arg Ser Ser Val Asp Val Leu Tyr Thr Phe Ala Asn
1               5                   10                  15

<210> SEQ ID NO 715
<211> LENGTH: 15
<212> TYPE: PRT
<213> ORGANISM: Homo sapiens

<400> SEQUENCE: 715

Ser Arg Ser Ser Val Asp Val Leu Tyr Thr Phe Ala Asn Cys Ser
1               5                   10                  15

<210> SEQ ID NO 716
<211> LENGTH: 15
<212> TYPE: PRT
<213> ORGANISM: Homo sapiens

<400> SEQUENCE: 716

Ala Asn Cys Ser Gly Leu Asp Leu Ile Phe Gly Leu Asn Ala Leu
1               5                   10                  15

<210> SEQ ID NO 717
<211> LENGTH: 15
<212> TYPE: PRT
<213> ORGANISM: Homo sapiens

<400> SEQUENCE: 717

Asn Cys Ser Gly Leu Asp Leu Ile Phe Gly Leu Asn Ala Leu Leu
1               5                   10                  15

<210> SEQ ID NO 718
<211> LENGTH: 15
<212> TYPE: PRT
<213> ORGANISM: Homo sapiens

<400> SEQUENCE: 718

Ser Gly Leu Asp Leu Ile Phe Gly Leu Asn Ala Leu Leu Arg Thr
1               5                   10                  15

<210> SEQ ID NO 719
<211> LENGTH: 15
<212> TYPE: PRT
<213> ORGANISM: Homo sapiens

<400> SEQUENCE: 719

Leu Ile Phe Gly Leu Asn Ala Leu Leu Arg Thr Ala Asp Leu Gln
1               5                   10                  15

<210> SEQ ID NO 720
<211> LENGTH: 15
<212> TYPE: PRT
```

-continued

<213> ORGANISM: Homo sapiens

<400> SEQUENCE: 720

Leu Leu Arg Thr Ala Asp Leu Gln Trp Asn Ser Ser Asn Ala Gln
1               5                   10                  15

<210> SEQ ID NO 721
<211> LENGTH: 15
<212> TYPE: PRT
<213> ORGANISM: Homo sapiens

<400> SEQUENCE: 721

Leu Arg Thr Ala Asp Leu Gln Trp Asn Ser Ser Asn Ala Gln Leu
1               5                   10                  15

<210> SEQ ID NO 722
<211> LENGTH: 15
<212> TYPE: PRT
<213> ORGANISM: Homo sapiens

<400> SEQUENCE: 722

Arg Thr Ala Asp Leu Gln Trp Asn Ser Ser Asn Ala Gln Leu Leu
1               5                   10                  15

<210> SEQ ID NO 723
<211> LENGTH: 15
<212> TYPE: PRT
<213> ORGANISM: Homo sapiens

<400> SEQUENCE: 723

Ala Asp Leu Gln Trp Asn Ser Ser Asn Ala Gln Leu Leu Leu Asp
1               5                   10                  15

<210> SEQ ID NO 724
<211> LENGTH: 15
<212> TYPE: PRT
<213> ORGANISM: Homo sapiens

<400> SEQUENCE: 724

Leu Gln Trp Asn Ser Ser Asn Ala Gln Leu Leu Leu Asp Tyr Cys
1               5                   10                  15

<210> SEQ ID NO 725
<211> LENGTH: 15
<212> TYPE: PRT
<213> ORGANISM: Homo sapiens

<400> SEQUENCE: 725

Ser Ser Asn Ala Gln Leu Leu Leu Asp Tyr Cys Ser Ser Lys Gly
1               5                   10                  15

<210> SEQ ID NO 726
<211> LENGTH: 15
<212> TYPE: PRT
<213> ORGANISM: Homo sapiens

<400> SEQUENCE: 726

Ser Asn Ala Gln Leu Leu Leu Asp Tyr Cys Ser Ser Lys Gly Tyr
1               5                   10                  15

<210> SEQ ID NO 727
<211> LENGTH: 15
<212> TYPE: PRT
<213> ORGANISM: Homo sapiens

<400> SEQUENCE: 727

Cys Ser Ser Lys Gly Tyr Asn Ile Ser Trp Glu Leu Gly Asn Glu
1               5                   10                  15

<210> SEQ ID NO 728
<211> LENGTH: 15
<212> TYPE: PRT
<213> ORGANISM: Homo sapiens

<400> SEQUENCE: 728

Trp Glu Leu Gly Asn Glu Pro Asn Ser Phe Leu Lys Lys Ala Asp
1               5                   10                  15

<210> SEQ ID NO 729
<211> LENGTH: 15
<212> TYPE: PRT
<213> ORGANISM: Homo sapiens

<400> SEQUENCE: 729

Asn Glu Pro Asn Ser Phe Leu Lys Lys Ala Asp Ile Phe Ile Asn
1               5                   10                  15

<210> SEQ ID NO 730
<211> LENGTH: 15
<212> TYPE: PRT
<213> ORGANISM: Homo sapiens

<400> SEQUENCE: 730

Phe Leu Lys Lys Ala Asp Ile Phe Ile Asn Gly Ser Gln Leu Gly
1               5                   10                  15

<210> SEQ ID NO 731
<211> LENGTH: 15
<212> TYPE: PRT
<213> ORGANISM: Homo sapiens

<400> SEQUENCE: 731

Lys Lys Ala Asp Ile Phe Ile Asn Gly Ser Gln Leu Gly Glu Asp
1               5                   10                  15

<210> SEQ ID NO 732
<211> LENGTH: 15
<212> TYPE: PRT
<213> ORGANISM: Homo sapiens

<400> SEQUENCE: 732

Phe Ile Asn Gly Ser Gln Leu Gly Glu Asp Phe Ile Gln Leu His
1               5                   10                  15

<210> SEQ ID NO 733
<211> LENGTH: 15
<212> TYPE: PRT
<213> ORGANISM: Homo sapiens

<400> SEQUENCE: 733

Asn Gly Ser Gln Leu Gly Glu Asp Phe Ile Gln Leu His Lys Leu
1               5                   10                  15

<210> SEQ ID NO 734
<211> LENGTH: 15
<212> TYPE: PRT
<213> ORGANISM: Homo sapiens

<400> SEQUENCE: 734

-continued

```
Gln Leu Gly Glu Asp Phe Ile Gln Leu His Lys Leu Leu Arg Lys
1               5                   10                  15
```

<210> SEQ ID NO 735
<211> LENGTH: 15
<212> TYPE: PRT
<213> ORGANISM: Homo sapiens

<400> SEQUENCE: 735

```
Leu Gly Glu Asp Phe Ile Gln Leu His Lys Leu Leu Arg Lys Ser
1               5                   10                  15
```

<210> SEQ ID NO 736
<211> LENGTH: 15
<212> TYPE: PRT
<213> ORGANISM: Homo sapiens

<400> SEQUENCE: 736

```
Thr Phe Lys Asn Ala Lys Leu Tyr Gly Pro Asp Val Gly Gln Pro
1               5                   10                  15
```

<210> SEQ ID NO 737
<211> LENGTH: 15
<212> TYPE: PRT
<213> ORGANISM: Homo sapiens

<400> SEQUENCE: 737

```
Lys Leu Tyr Gly Pro Asp Val Gly Gln Pro Arg Arg Lys Thr Ala
1               5                   10                  15
```

<210> SEQ ID NO 738
<211> LENGTH: 15
<212> TYPE: PRT
<213> ORGANISM: Homo sapiens

<400> SEQUENCE: 738

```
Tyr Gly Pro Asp Val Gly Gln Pro Arg Arg Lys Thr Ala Lys Met
1               5                   10                  15
```

<210> SEQ ID NO 739
<211> LENGTH: 15
<212> TYPE: PRT
<213> ORGANISM: Homo sapiens

<400> SEQUENCE: 739

```
Gln Pro Arg Arg Lys Thr Ala Lys Met Leu Lys Ser Phe Leu Lys
1               5                   10                  15
```

<210> SEQ ID NO 740
<211> LENGTH: 15
<212> TYPE: PRT
<213> ORGANISM: Homo sapiens

<400> SEQUENCE: 740

```
Phe Leu Lys Ala Gly Gly Glu Val Ile Asp Ser Val Thr Trp His
1               5                   10                  15
```

<210> SEQ ID NO 741
<211> LENGTH: 15
<212> TYPE: PRT
<213> ORGANISM: Homo sapiens

<400> SEQUENCE: 741

```
Leu Lys Ala Gly Gly Glu Val Ile Asp Ser Val Thr Trp His His
1               5                   10                  15
```

<210> SEQ ID NO 742
<211> LENGTH: 15
<212> TYPE: PRT
<213> ORGANISM: Homo sapiens

<400> SEQUENCE: 742

Lys Ala Gly Gly Glu Val Ile Asp Ser Val Thr Trp His His Tyr
1               5                   10                  15

<210> SEQ ID NO 743
<211> LENGTH: 15
<212> TYPE: PRT
<213> ORGANISM: Homo sapiens

<400> SEQUENCE: 743

Val Ile Asp Ser Val Thr Trp His His Tyr Tyr Leu Asn Gly Arg
1               5                   10                  15

<210> SEQ ID NO 744
<211> LENGTH: 15
<212> TYPE: PRT
<213> ORGANISM: Homo sapiens

<400> SEQUENCE: 744

Val Thr Trp His His Tyr Tyr Leu Asn Gly Arg Thr Ala Thr Arg
1               5                   10                  15

<210> SEQ ID NO 745
<211> LENGTH: 15
<212> TYPE: PRT
<213> ORGANISM: Homo sapiens

<400> SEQUENCE: 745

Thr Trp His His Tyr Tyr Leu Asn Gly Arg Thr Ala Thr Arg Glu
1               5                   10                  15

<210> SEQ ID NO 746
<211> LENGTH: 15
<212> TYPE: PRT
<213> ORGANISM: Homo sapiens

<400> SEQUENCE: 746

Tyr Leu Asn Gly Arg Thr Ala Thr Arg Glu Asp Phe Leu Asn Pro
1               5                   10                  15

<210> SEQ ID NO 747
<211> LENGTH: 15
<212> TYPE: PRT
<213> ORGANISM: Homo sapiens

<400> SEQUENCE: 747

Ala Thr Arg Glu Asp Phe Leu Asn Pro Asp Val Leu Asp Ile Phe
1               5                   10                  15

<210> SEQ ID NO 748
<211> LENGTH: 15
<212> TYPE: PRT
<213> ORGANISM: Homo sapiens

<400> SEQUENCE: 748

Asp Phe Leu Asn Pro Asp Val Leu Asp Ile Phe Ile Ser Ser Val
1               5                   10                  15

```
<210> SEQ ID NO 749
<211> LENGTH: 15
<212> TYPE: PRT
<213> ORGANISM: Homo sapiens

<400> SEQUENCE: 749

Phe Leu Asn Pro Asp Val Leu Asp Ile Phe Ile Ser Ser Val Gln
1               5                   10                  15

<210> SEQ ID NO 750
<211> LENGTH: 15
<212> TYPE: PRT
<213> ORGANISM: Homo sapiens

<400> SEQUENCE: 750

Leu Asn Pro Asp Val Leu Asp Ile Phe Ile Ser Ser Val Gln Lys
1               5                   10                  15

<210> SEQ ID NO 751
<211> LENGTH: 15
<212> TYPE: PRT
<213> ORGANISM: Homo sapiens

<400> SEQUENCE: 751

Ser Ser Val Gln Lys Val Phe Gln Val Val Glu Ser Thr Arg Pro
1               5                   10                  15

<210> SEQ ID NO 752
<211> LENGTH: 15
<212> TYPE: PRT
<213> ORGANISM: Homo sapiens

<400> SEQUENCE: 752

Lys Val Phe Gln Val Val Glu Ser Thr Arg Pro Gly Lys Lys Val
1               5                   10                  15

<210> SEQ ID NO 753
<211> LENGTH: 15
<212> TYPE: PRT
<213> ORGANISM: Homo sapiens

<400> SEQUENCE: 753

Thr Arg Pro Gly Lys Lys Val Trp Leu Gly Glu Thr Ser Ser Ala
1               5                   10                  15

<210> SEQ ID NO 754
<211> LENGTH: 15
<212> TYPE: PRT
<213> ORGANISM: Homo sapiens

<400> SEQUENCE: 754

Pro Gly Lys Lys Val Trp Leu Gly Glu Thr Ser Ser Ala Tyr Gly
1               5                   10                  15

<210> SEQ ID NO 755
<211> LENGTH: 15
<212> TYPE: PRT
<213> ORGANISM: Homo sapiens

<400> SEQUENCE: 755

Leu Gly Glu Thr Ser Ser Ala Tyr Gly Gly Ala Pro Leu Leu
1               5                   10                  15

<210> SEQ ID NO 756
<211> LENGTH: 15
```

```
<212> TYPE: PRT
<213> ORGANISM: Homo sapiens

<400> SEQUENCE: 756

Tyr Gly Gly Gly Ala Pro Leu Leu Ser Asp Thr Phe Ala Ala Gly
1               5                   10                  15

<210> SEQ ID NO 757
<211> LENGTH: 15
<212> TYPE: PRT
<213> ORGANISM: Homo sapiens

<400> SEQUENCE: 757

Gly Gly Gly Ala Pro Leu Leu Ser Asp Thr Phe Ala Ala Gly Phe
1               5                   10                  15

<210> SEQ ID NO 758
<211> LENGTH: 15
<212> TYPE: PRT
<213> ORGANISM: Homo sapiens

<400> SEQUENCE: 758

Gly Gly Ala Pro Leu Leu Ser Asp Thr Phe Ala Ala Gly Phe Met
1               5                   10                  15

<210> SEQ ID NO 759
<211> LENGTH: 15
<212> TYPE: PRT
<213> ORGANISM: Homo sapiens

<400> SEQUENCE: 759

Pro Leu Leu Ser Asp Thr Phe Ala Ala Gly Phe Met Trp Leu Asp
1               5                   10                  15

<210> SEQ ID NO 760
<211> LENGTH: 15
<212> TYPE: PRT
<213> ORGANISM: Homo sapiens

<400> SEQUENCE: 760

Leu Ser Asp Thr Phe Ala Ala Gly Phe Met Trp Leu Asp Lys Leu
1               5                   10                  15

<210> SEQ ID NO 761
<211> LENGTH: 15
<212> TYPE: PRT
<213> ORGANISM: Homo sapiens

<400> SEQUENCE: 761

Asp Thr Phe Ala Ala Gly Phe Met Trp Leu Asp Lys Leu Gly Leu
1               5                   10                  15

<210> SEQ ID NO 762
<211> LENGTH: 15
<212> TYPE: PRT
<213> ORGANISM: Homo sapiens

<400> SEQUENCE: 762

Met Trp Leu Asp Lys Leu Gly Leu Ser Ala Arg Met Gly Ile Glu
1               5                   10                  15

<210> SEQ ID NO 763
<211> LENGTH: 15
<212> TYPE: PRT
<213> ORGANISM: Homo sapiens
```

<400> SEQUENCE: 763

Ala Arg Met Gly Ile Glu Val Val Met Arg Gln Val Phe Phe Gly
1               5                   10                  15

<210> SEQ ID NO 764
<211> LENGTH: 15
<212> TYPE: PRT
<213> ORGANISM: Homo sapiens

<400> SEQUENCE: 764

Val Val Met Arg Gln Val Phe Phe Gly Ala Gly Asn Tyr His Leu
1               5                   10                  15

<210> SEQ ID NO 765
<211> LENGTH: 15
<212> TYPE: PRT
<213> ORGANISM: Homo sapiens

<400> SEQUENCE: 765

Gly Asn Tyr His Leu Val Asp Glu Asn Phe Asp Pro Leu Pro Asp
1               5                   10                  15

<210> SEQ ID NO 766
<211> LENGTH: 15
<212> TYPE: PRT
<213> ORGANISM: Homo sapiens

<400> SEQUENCE: 766

Asn Phe Asp Pro Leu Pro Asp Tyr Trp Leu Ser Leu Leu Phe Lys
1               5                   10                  15

<210> SEQ ID NO 767
<211> LENGTH: 15
<212> TYPE: PRT
<213> ORGANISM: Homo sapiens

<400> SEQUENCE: 767

Pro Leu Pro Asp Tyr Trp Leu Ser Leu Leu Phe Lys Lys Leu Val
1               5                   10                  15

<210> SEQ ID NO 768
<211> LENGTH: 15
<212> TYPE: PRT
<213> ORGANISM: Homo sapiens

<400> SEQUENCE: 768

Lys Leu Val Gly Thr Lys Val Leu Met Ala Ser Val Gln Gly Ser
1               5                   10                  15

<210> SEQ ID NO 769
<211> LENGTH: 15
<212> TYPE: PRT
<213> ORGANISM: Homo sapiens

<400> SEQUENCE: 769

Leu Val Gly Thr Lys Val Leu Met Ala Ser Val Gln Gly Ser Lys
1               5                   10                  15

<210> SEQ ID NO 770
<211> LENGTH: 15
<212> TYPE: PRT
<213> ORGANISM: Homo sapiens

<400> SEQUENCE: 770

Lys Arg Arg Lys Leu Arg Val Tyr Leu His Cys Thr Asn Thr Asp
1               5                   10                  15

<210> SEQ ID NO 771
<211> LENGTH: 15
<212> TYPE: PRT
<213> ORGANISM: Homo sapiens

<400> SEQUENCE: 771

Arg Lys Leu Arg Val Tyr Leu His Cys Thr Asn Thr Asp Asn Pro
1               5                   10                  15

<210> SEQ ID NO 772
<211> LENGTH: 15
<212> TYPE: PRT
<213> ORGANISM: Homo sapiens

<400> SEQUENCE: 772

Leu His Cys Thr Asn Thr Asp Asn Pro Arg Tyr Lys Glu Gly Asp
1               5                   10                  15

<210> SEQ ID NO 773
<211> LENGTH: 15
<212> TYPE: PRT
<213> ORGANISM: Homo sapiens

<400> SEQUENCE: 773

Asp Asn Pro Arg Tyr Lys Glu Gly Asp Leu Thr Leu Tyr Ala Ile
1               5                   10                  15

<210> SEQ ID NO 774
<211> LENGTH: 15
<212> TYPE: PRT
<213> ORGANISM: Homo sapiens

<400> SEQUENCE: 774

Arg Tyr Lys Glu Gly Asp Leu Thr Leu Tyr Ala Ile Asn Leu His
1               5                   10                  15

<210> SEQ ID NO 775
<211> LENGTH: 15
<212> TYPE: PRT
<213> ORGANISM: Homo sapiens

<400> SEQUENCE: 775

Lys Glu Gly Asp Leu Thr Leu Tyr Ala Ile Asn Leu His Asn Val
1               5                   10                  15

<210> SEQ ID NO 776
<211> LENGTH: 15
<212> TYPE: PRT
<213> ORGANISM: Homo sapiens

<400> SEQUENCE: 776

Tyr Ala Ile Asn Leu His Asn Val Thr Lys Tyr Leu Arg Leu Pro
1               5                   10                  15

<210> SEQ ID NO 777
<211> LENGTH: 15
<212> TYPE: PRT
<213> ORGANISM: Homo sapiens

<400> SEQUENCE: 777

Leu Pro Tyr Pro Phe Ser Asn Lys Gln Val Asp Lys Tyr Leu Leu

-continued

```
1               5                  10                  15
```

<210> SEQ ID NO 778
<211> LENGTH: 15
<212> TYPE: PRT
<213> ORGANISM: Homo sapiens

<400> SEQUENCE: 778

```
Pro Phe Ser Asn Lys Gln Val Asp Lys Tyr Leu Leu Arg Pro Leu
1               5                  10                  15
```

<210> SEQ ID NO 779
<211> LENGTH: 15
<212> TYPE: PRT
<213> ORGANISM: Homo sapiens

<400> SEQUENCE: 779

```
Lys Gln Val Asp Lys Tyr Leu Leu Arg Pro Leu Gly Pro His Gly
1               5                  10                  15
```

<210> SEQ ID NO 780
<211> LENGTH: 15
<212> TYPE: PRT
<213> ORGANISM: Homo sapiens

<400> SEQUENCE: 780

```
Tyr Leu Leu Arg Pro Leu Gly Pro His Gly Leu Leu Ser Lys Ser
1               5                  10                  15
```

<210> SEQ ID NO 781
<211> LENGTH: 15
<212> TYPE: PRT
<213> ORGANISM: Homo sapiens

<400> SEQUENCE: 781

```
Leu Gly Pro His Gly Leu Leu Ser Lys Ser Val Gln Leu Asn Gly
1               5                  10                  15
```

<210> SEQ ID NO 782
<211> LENGTH: 15
<212> TYPE: PRT
<213> ORGANISM: Homo sapiens

<400> SEQUENCE: 782

```
Gly Pro His Gly Leu Leu Ser Lys Ser Val Gln Leu Asn Gly Leu
1               5                  10                  15
```

<210> SEQ ID NO 783
<211> LENGTH: 15
<212> TYPE: PRT
<213> ORGANISM: Homo sapiens

<400> SEQUENCE: 783

```
Gly Leu Leu Ser Lys Ser Val Gln Leu Asn Gly Leu Thr Leu Lys
1               5                  10                  15
```

<210> SEQ ID NO 784
<211> LENGTH: 15
<212> TYPE: PRT
<213> ORGANISM: Homo sapiens

<400> SEQUENCE: 784

```
Leu Leu Ser Lys Ser Val Gln Leu Asn Gly Leu Thr Leu Lys Met
1               5                  10                  15
```

```
<210> SEQ ID NO 785
<211> LENGTH: 15
<212> TYPE: PRT
<213> ORGANISM: Homo sapiens

<400> SEQUENCE: 785

Leu Ser Lys Ser Val Gln Leu Asn Gly Leu Thr Leu Lys Met Val
1               5                   10                  15

<210> SEQ ID NO 786
<211> LENGTH: 15
<212> TYPE: PRT
<213> ORGANISM: Homo sapiens

<400> SEQUENCE: 786

Lys Ser Val Gln Leu Asn Gly Leu Thr Leu Lys Met Val Asp Asp
1               5                   10                  15

<210> SEQ ID NO 787
<211> LENGTH: 15
<212> TYPE: PRT
<213> ORGANISM: Homo sapiens

<400> SEQUENCE: 787

Leu Thr Leu Lys Met Val Asp Asp Gln Thr Leu Pro Pro Leu Met
1               5                   10                  15

<210> SEQ ID NO 788
<211> LENGTH: 15
<212> TYPE: PRT
<213> ORGANISM: Homo sapiens

<400> SEQUENCE: 788

Pro Leu Met Glu Lys Pro Leu Arg Pro Gly Ser Ser Leu Gly Leu
1               5                   10                  15

<210> SEQ ID NO 789
<211> LENGTH: 15
<212> TYPE: PRT
<213> ORGANISM: Homo sapiens

<400> SEQUENCE: 789

Ser Ser Leu Gly Leu Pro Ala Phe Ser Tyr Ser Phe Phe Val Ile
1               5                   10                  15

<210> SEQ ID NO 790
<211> LENGTH: 15
<212> TYPE: PRT
<213> ORGANISM: Homo sapiens

<400> SEQUENCE: 790

Leu Gly Leu Pro Ala Phe Ser Tyr Ser Phe Phe Val Ile Arg Asn
1               5                   10                  15

<210> SEQ ID NO 791
<211> LENGTH: 15
<212> TYPE: PRT
<213> ORGANISM: Homo sapiens

<400> SEQUENCE: 791

Pro Ala Phe Ser Tyr Ser Phe Phe Val Ile Arg Asn Ala Lys Val
1               5                   10                  15

<210> SEQ ID NO 792
```

```
<211> LENGTH: 15
<212> TYPE: PRT
<213> ORGANISM: Homo sapiens

<400> SEQUENCE: 792

Glu Ser Thr Phe Glu Glu Arg Ser Tyr Trp Gln Ser Gln Val Asn
1               5                   10                  15

<210> SEQ ID NO 793
<211> LENGTH: 15
<212> TYPE: PRT
<213> ORGANISM: Homo sapiens

<400> SEQUENCE: 793

Arg Glu His Tyr Gln Lys Lys Phe Lys Asn Ser Thr Tyr Ser Arg
1               5                   10                  15

<210> SEQ ID NO 794
<211> LENGTH: 15
<212> TYPE: PRT
<213> ORGANISM: Homo sapiens

<400> SEQUENCE: 794

Pro Asn Ser Phe Leu Lys Lys Ala Asp Ile Phe Ile Asn Gly Ser
1               5                   10                  15

<210> SEQ ID NO 795
<211> LENGTH: 15
<212> TYPE: PRT
<213> ORGANISM: Homo sapiens

<400> SEQUENCE: 795

Gly Phe Met Trp Leu Asp Lys Leu Gly Leu Ser Ala Arg Met Gly
1               5                   10                  15

<210> SEQ ID NO 796
<211> LENGTH: 15
<212> TYPE: PRT
<213> ORGANISM: Homo sapiens

<400> SEQUENCE: 796

Tyr Ser Phe Phe Val Ile Arg Asn Ala Lys Val Ala Ala Cys Ile
1               5                   10                  15

<210> SEQ ID NO 797
<211> LENGTH: 15
<212> TYPE: PRT
<213> ORGANISM: Homo sapiens

<400> SEQUENCE: 797

Glu Arg Ser Tyr Trp Gln Ser Gln Val Asn Gln Asp Ile Cys Lys
1               5                   10                  15

<210> SEQ ID NO 798
<211> LENGTH: 15
<212> TYPE: PRT
<213> ORGANISM: Homo sapiens

<400> SEQUENCE: 798

Glu Trp Pro Tyr Gln Glu Gln Leu Leu Leu Arg Glu His Tyr Gln
1               5                   10                  15

<210> SEQ ID NO 799
<211> LENGTH: 15
<212> TYPE: PRT
```

<213> ORGANISM: Homo sapiens

<400> SEQUENCE: 799

Ser Val Thr Trp His His Tyr Tyr Leu Asn Gly Arg Thr Ala Thr
1               5                   10                  15

<210> SEQ ID NO 800
<211> LENGTH: 15
<212> TYPE: PRT
<213> ORGANISM: Homo sapiens

<400> SEQUENCE: 800

Ser Asp Thr Phe Ala Ala Gly Phe Met Trp Leu Asp Lys Leu Gly
1               5                   10                  15

<210> SEQ ID NO 801
<211> LENGTH: 15
<212> TYPE: PRT
<213> ORGANISM: Homo sapiens

<400> SEQUENCE: 801

Asn Pro Arg Tyr Lys Glu Gly Asp Leu Thr Leu Tyr Ala Ile Asn
1               5                   10                  15

<210> SEQ ID NO 802
<211> LENGTH: 15
<212> TYPE: PRT
<213> ORGANISM: Homo sapiens

<400> SEQUENCE: 802

Arg Leu Pro Tyr Pro Phe Ser Asn Lys Gln Val Asp Lys Tyr Leu
1               5                   10                  15

<210> SEQ ID NO 803
<211> LENGTH: 15
<212> TYPE: PRT
<213> ORGANISM: Homo sapiens

<400> SEQUENCE: 803

Leu Pro Ala Phe Ser Tyr Ser Phe Phe Val Ile Arg Asn Ala Lys
1               5                   10                  15

<210> SEQ ID NO 804
<211> LENGTH: 15
<212> TYPE: PRT
<213> ORGANISM: Homo sapiens

<400> SEQUENCE: 804

Pro Pro Asp Val Glu Glu Lys Leu Arg Leu Glu Trp Pro Tyr Gln
1               5                   10                  15

<210> SEQ ID NO 805
<211> LENGTH: 15
<212> TYPE: PRT
<213> ORGANISM: Homo sapiens

<400> SEQUENCE: 805

Lys Leu Gly Leu Ser Ala Arg Met Gly Ile Glu Val Val Met Arg
1               5                   10                  15

<210> SEQ ID NO 806
<211> LENGTH: 15
<212> TYPE: PRT
<213> ORGANISM: Homo sapiens -continued

```
<400> SEQUENCE: 806

Trp Leu Ser Leu Leu Phe Lys Lys Leu Val Gly Thr Lys Val Leu
1               5                   10                  15

<210> SEQ ID NO 807
<211> LENGTH: 15
<212> TYPE: PRT
<213> ORGANISM: Homo sapiens

<400> SEQUENCE: 807

Leu Ser Leu Leu Phe Lys Lys Leu Val Gly Thr Lys Val Leu Met
1               5                   10                  15

<210> SEQ ID NO 808
<211> LENGTH: 15
<212> TYPE: PRT
<213> ORGANISM: Homo sapiens

<400> SEQUENCE: 808

Lys Lys Leu Val Gly Thr Lys Val Leu Met Ala Ser Val Gln Gly
1               5                   10                  15

<210> SEQ ID NO 809
<211> LENGTH: 15
<212> TYPE: PRT
<213> ORGANISM: Homo sapiens

<400> SEQUENCE: 809

Pro His Gly Leu Leu Ser Lys Ser Val Gln Leu Asn Gly Leu Thr
1               5                   10                  15

<210> SEQ ID NO 810
<211> LENGTH: 15
<212> TYPE: PRT
<213> ORGANISM: Homo sapiens

<400> SEQUENCE: 810

Leu Asn Gly Leu Thr Leu Lys Met Val Asp Asp Gln Thr Leu Pro
1               5                   10                  15

<210> SEQ ID NO 811
<211> LENGTH: 15
<212> TYPE: PRT
<213> ORGANISM: Homo sapiens

<400> SEQUENCE: 811

Leu Gly Pro Leu Ser Pro Gly Ala Leu Pro Arg Pro Ala Gln Ala
1               5                   10                  15

<210> SEQ ID NO 812
<211> LENGTH: 15
<212> TYPE: PRT
<213> ORGANISM: Homo sapiens

<400> SEQUENCE: 812

Ser Val Thr Ile Asp Ala Asn Leu Ala Thr Asp Pro Arg Phe Leu
1               5                   10                  15

<210> SEQ ID NO 813
<211> LENGTH: 15
<212> TYPE: PRT
<213> ORGANISM: Homo sapiens

<400> SEQUENCE: 813
```

-continued

```
Arg Phe Leu Ile Leu Leu Gly Ser Pro Lys Leu Arg Thr Leu Ala
1               5                   10                  15
```

<210> SEQ ID NO 814
<211> LENGTH: 15
<212> TYPE: PRT
<213> ORGANISM: Homo sapiens

<400> SEQUENCE: 814

```
Leu Asn Ala Leu Leu Arg Thr Ala Asp Leu Gln Trp Asn Ser Ser
1               5                   10                  15
```

<210> SEQ ID NO 815
<211> LENGTH: 15
<212> TYPE: PRT
<213> ORGANISM: Homo sapiens

<400> SEQUENCE: 815

```
Asp Ile Phe Ile Asn Gly Ser Gln Leu Gly Glu Asp Phe Ile Gln
1               5                   10                  15
```

<210> SEQ ID NO 816
<211> LENGTH: 15
<212> TYPE: PRT
<213> ORGANISM: Homo sapiens

<400> SEQUENCE: 816

```
Asn Ala Lys Leu Tyr Gly Pro Asp Val Gly Gln Pro Arg Arg Lys
1               5                   10                  15
```

<210> SEQ ID NO 817
<211> LENGTH: 15
<212> TYPE: PRT
<213> ORGANISM: Homo sapiens

<400> SEQUENCE: 817

```
Thr Ala Lys Met Leu Lys Ser Phe Leu Lys Ala Gly Gly Glu Val
1               5                   10                  15
```

<210> SEQ ID NO 818
<211> LENGTH: 15
<212> TYPE: PRT
<213> ORGANISM: Homo sapiens

<400> SEQUENCE: 818

```
Lys Ser Phe Leu Lys Ala Gly Gly Glu Val Ile Asp Ser Val Thr
1               5                   10                  15
```

<210> SEQ ID NO 819
<211> LENGTH: 15
<212> TYPE: PRT
<213> ORGANISM: Homo sapiens

<400> SEQUENCE: 819

```
Ala Pro Leu Leu Ser Asp Thr Phe Ala Ala Gly Phe Met Trp Leu
1               5                   10                  15
```

<210> SEQ ID NO 820
<211> LENGTH: 15
<212> TYPE: PRT
<213> ORGANISM: Homo sapiens

<400> SEQUENCE: 820

```
Met Arg Gln Val Phe Phe Gly Ala Gly Asn Tyr His Leu Val Asp
1               5                   10                  15
```

-continued

<210> SEQ ID NO 821
<211> LENGTH: 15
<212> TYPE: PRT
<213> ORGANISM: Homo sapiens

<400> SEQUENCE: 821

Tyr His Leu Val Asp Glu Asn Phe Asp Pro Leu Pro Asp Tyr Trp
1               5                   10                  15

<210> SEQ ID NO 822
<211> LENGTH: 15
<212> TYPE: PRT
<213> ORGANISM: Homo sapiens

<400> SEQUENCE: 822

Glu Gly Asp Leu Thr Leu Tyr Ala Ile Asn Leu His Asn Val Thr
1               5                   10                  15

<210> SEQ ID NO 823
<211> LENGTH: 15
<212> TYPE: PRT
<213> ORGANISM: Homo sapiens

<400> SEQUENCE: 823

Leu Tyr Ala Ile Asn Leu His Asn Val Thr Lys Tyr Leu Arg Leu
1               5                   10                  15

<210> SEQ ID NO 824
<211> LENGTH: 15
<212> TYPE: PRT
<213> ORGANISM: Homo sapiens

<400> SEQUENCE: 824

Asp Lys Tyr Leu Leu Arg Pro Leu Gly Pro His Gly Leu Leu Ser
1               5                   10                  15

<210> SEQ ID NO 825
<211> LENGTH: 15
<212> TYPE: PRT
<213> ORGANISM: Homo sapiens

<400> SEQUENCE: 825

Ile Leu Leu Gly Ser Pro Lys Leu Arg Thr Leu Ala Arg Gly Leu
1               5                   10                  15

<210> SEQ ID NO 826
<211> LENGTH: 15
<212> TYPE: PRT
<213> ORGANISM: Homo sapiens

<400> SEQUENCE: 826

His Tyr Gln Lys Lys Phe Lys Asn Ser Thr Tyr Ser Arg Ser Ser
1               5                   10                  15

<210> SEQ ID NO 827
<211> LENGTH: 15
<212> TYPE: PRT
<213> ORGANISM: Homo sapiens

<400> SEQUENCE: 827

Lys Asn Ser Thr Tyr Ser Arg Ser Ser Val Asp Val Leu Tyr Thr
1               5                   10                  15

```
<210> SEQ ID NO 828
<211> LENGTH: 15
<212> TYPE: PRT
<213> ORGANISM: Homo sapiens

<400> SEQUENCE: 828

Gln Leu His Lys Leu Leu Arg Lys Ser Thr Phe Lys Asn Ala Lys
1               5                   10                  15

<210> SEQ ID NO 829
<211> LENGTH: 15
<212> TYPE: PRT
<213> ORGANISM: Homo sapiens

<400> SEQUENCE: 829

Asp Val Gly Gln Pro Arg Arg Lys Thr Ala Lys Met Leu Lys Ser
1               5                   10                  15

<210> SEQ ID NO 830
<211> LENGTH: 15
<212> TYPE: PRT
<213> ORGANISM: Homo sapiens

<400> SEQUENCE: 830

Gln Gly Ser Lys Arg Arg Lys Leu Arg Val Tyr Leu His Cys Thr
1               5                   10                  15

<210> SEQ ID NO 831
<211> LENGTH: 15
<212> TYPE: PRT
<213> ORGANISM: Homo sapiens

<400> SEQUENCE: 831

Arg Ser Lys Pro Ala Leu Pro Pro Leu Met Leu Leu Leu Leu Leu
1               5                   10                  15

<210> SEQ ID NO 832
<211> LENGTH: 15
<212> TYPE: PRT
<213> ORGANISM: Homo sapiens

<400> SEQUENCE: 832

Ser Lys Pro Ala Leu Pro Pro Pro Leu Met Leu Leu Leu Leu Gly
1               5                   10                  15

<210> SEQ ID NO 833
<211> LENGTH: 15
<212> TYPE: PRT
<213> ORGANISM: Homo sapiens

<400> SEQUENCE: 833

Leu Pro Pro Pro Leu Met Leu Leu Leu Gly Pro Leu Gly Pro
1               5                   10                  15

<210> SEQ ID NO 834
<211> LENGTH: 15
<212> TYPE: PRT
<213> ORGANISM: Homo sapiens

<400> SEQUENCE: 834

Leu Ser Pro Gly Ala Leu Pro Arg Pro Ala Gln Ala Gln Asp Val
1               5                   10                  15

<210> SEQ ID NO 835
<211> LENGTH: 15
```

<212> TYPE: PRT
<213> ORGANISM: Homo sapiens

<400> SEQUENCE: 835

Leu Pro Arg Pro Ala Gln Ala Gln Asp Val Val Asp Leu Asp Phe
1               5                   10                  15

<210> SEQ ID NO 836
<211> LENGTH: 15
<212> TYPE: PRT
<213> ORGANISM: Homo sapiens

<400> SEQUENCE: 836

Pro Arg Pro Ala Gln Ala Gln Asp Val Val Asp Leu Asp Phe Phe
1               5                   10                  15

<210> SEQ ID NO 837
<211> LENGTH: 15
<212> TYPE: PRT
<213> ORGANISM: Homo sapiens

<400> SEQUENCE: 837

Arg Pro Ala Gln Ala Gln Asp Val Val Asp Leu Asp Phe Phe Thr
1               5                   10                  15

<210> SEQ ID NO 838
<211> LENGTH: 15
<212> TYPE: PRT
<213> ORGANISM: Homo sapiens

<400> SEQUENCE: 838

Pro Ala Gln Ala Gln Asp Val Val Asp Leu Asp Phe Phe Thr Gln
1               5                   10                  15

<210> SEQ ID NO 839
<211> LENGTH: 15
<212> TYPE: PRT
<213> ORGANISM: Homo sapiens

<400> SEQUENCE: 839

Ala Gln Ala Gln Asp Val Val Asp Leu Asp Phe Phe Thr Gln Glu
1               5                   10                  15

<210> SEQ ID NO 840
<211> LENGTH: 15
<212> TYPE: PRT
<213> ORGANISM: Homo sapiens

<400> SEQUENCE: 840

Phe Phe Thr Gln Glu Pro Leu His Leu Val Ser Pro Ser Phe Leu
1               5                   10                  15

<210> SEQ ID NO 841
<211> LENGTH: 15
<212> TYPE: PRT
<213> ORGANISM: Homo sapiens

<400> SEQUENCE: 841

Phe Thr Gln Glu Pro Leu His Leu Val Ser Pro Ser Phe Leu Ser
1               5                   10                  15

<210> SEQ ID NO 842
<211> LENGTH: 15
<212> TYPE: PRT
<213> ORGANISM: Homo sapiens

```
<400> SEQUENCE: 842

Leu Val Ser Pro Ser Phe Leu Ser Val Thr Ile Asp Ala Asn Leu
1               5                   10                  15

<210> SEQ ID NO 843
<211> LENGTH: 15
<212> TYPE: PRT
<213> ORGANISM: Homo sapiens

<400> SEQUENCE: 843

Leu Ser Val Thr Ile Asp Ala Asn Leu Ala Thr Asp Pro Arg Phe
1               5                   10                  15

<210> SEQ ID NO 844
<211> LENGTH: 15
<212> TYPE: PRT
<213> ORGANISM: Homo sapiens

<400> SEQUENCE: 844

Thr Ile Asp Ala Asn Leu Ala Thr Asp Pro Arg Phe Leu Ile Leu
1               5                   10                  15

<210> SEQ ID NO 845
<211> LENGTH: 15
<212> TYPE: PRT
<213> ORGANISM: Homo sapiens

<400> SEQUENCE: 845

Ile Asp Ala Asn Leu Ala Thr Asp Pro Arg Phe Leu Ile Leu Leu
1               5                   10                  15

<210> SEQ ID NO 846
<211> LENGTH: 15
<212> TYPE: PRT
<213> ORGANISM: Homo sapiens

<400> SEQUENCE: 846

Ala Asn Leu Ala Thr Asp Pro Arg Phe Leu Ile Leu Leu Gly Ser
1               5                   10                  15

<210> SEQ ID NO 847
<211> LENGTH: 15
<212> TYPE: PRT
<213> ORGANISM: Homo sapiens

<400> SEQUENCE: 847

Leu Ala Thr Asp Pro Arg Phe Leu Ile Leu Leu Gly Ser Pro Lys
1               5                   10                  15

<210> SEQ ID NO 848
<211> LENGTH: 15
<212> TYPE: PRT
<213> ORGANISM: Homo sapiens

<400> SEQUENCE: 848

Thr Asp Pro Arg Phe Leu Ile Leu Leu Gly Ser Pro Lys Leu Arg
1               5                   10                  15

<210> SEQ ID NO 849
<211> LENGTH: 15
<212> TYPE: PRT
<213> ORGANISM: Homo sapiens

<400> SEQUENCE: 849
```

```
Gly Ser Pro Lys Leu Arg Thr Leu Ala Arg Gly Leu Ser Pro Ala
1               5                   10                  15

<210> SEQ ID NO 850
<211> LENGTH: 15
<212> TYPE: PRT
<213> ORGANISM: Homo sapiens

<400> SEQUENCE: 850

Pro Lys Leu Arg Thr Leu Ala Arg Gly Leu Ser Pro Ala Tyr Leu
1               5                   10                  15

<210> SEQ ID NO 851
<211> LENGTH: 15
<212> TYPE: PRT
<213> ORGANISM: Homo sapiens

<400> SEQUENCE: 851

Arg Gly Leu Ser Pro Ala Tyr Leu Arg Phe Gly Gly Thr Lys Thr
1               5                   10                  15

<210> SEQ ID NO 852
<211> LENGTH: 15
<212> TYPE: PRT
<213> ORGANISM: Homo sapiens

<400> SEQUENCE: 852

Phe Gly Gly Thr Lys Thr Asp Phe Leu Ile Phe Asp Pro Lys Lys
1               5                   10                  15

<210> SEQ ID NO 853
<211> LENGTH: 15
<212> TYPE: PRT
<213> ORGANISM: Homo sapiens

<400> SEQUENCE: 853

Gly Gly Thr Lys Thr Asp Phe Leu Ile Phe Asp Pro Lys Lys Glu
1               5                   10                  15

<210> SEQ ID NO 854
<211> LENGTH: 15
<212> TYPE: PRT
<213> ORGANISM: Homo sapiens

<400> SEQUENCE: 854

Asp Pro Lys Lys Glu Ser Thr Phe Glu Glu Arg Ser Tyr Trp Gln
1               5                   10                  15

<210> SEQ ID NO 855
<211> LENGTH: 15
<212> TYPE: PRT
<213> ORGANISM: Homo sapiens

<400> SEQUENCE: 855

Pro Lys Lys Glu Ser Thr Phe Glu Glu Arg Ser Tyr Trp Gln Ser
1               5                   10                  15

<210> SEQ ID NO 856
<211> LENGTH: 15
<212> TYPE: PRT
<213> ORGANISM: Homo sapiens

<400> SEQUENCE: 856

Ser Thr Phe Glu Glu Arg Ser Tyr Trp Gln Ser Gln Val Asn Gln
```

-continued

```
1               5                   10                  15
```

<210> SEQ ID NO 857
<211> LENGTH: 15
<212> TYPE: PRT
<213> ORGANISM: Homo sapiens

<400> SEQUENCE: 857

```
Tyr Trp Gln Ser Gln Val Asn Gln Asp Ile Cys Lys Tyr Gly Ser
1               5                   10                  15
```

<210> SEQ ID NO 858
<211> LENGTH: 15
<212> TYPE: PRT
<213> ORGANISM: Homo sapiens

<400> SEQUENCE: 858

```
Gln Val Asn Gln Asp Ile Cys Lys Tyr Gly Ser Ile Pro Pro Asp
1               5                   10                  15
```

<210> SEQ ID NO 859
<211> LENGTH: 15
<212> TYPE: PRT
<213> ORGANISM: Homo sapiens

<400> SEQUENCE: 859

```
Asp Ile Cys Lys Tyr Gly Ser Ile Pro Pro Asp Val Glu Glu Lys
1               5                   10                  15
```

<210> SEQ ID NO 860
<211> LENGTH: 15
<212> TYPE: PRT
<213> ORGANISM: Homo sapiens

<400> SEQUENCE: 860

```
Lys Tyr Gly Ser Ile Pro Pro Asp Val Glu Glu Lys Leu Arg Leu
1               5                   10                  15
```

<210> SEQ ID NO 861
<211> LENGTH: 15
<212> TYPE: PRT
<213> ORGANISM: Homo sapiens

<400> SEQUENCE: 861

```
Gly Ser Ile Pro Pro Asp Val Glu Glu Lys Leu Arg Leu Glu Trp
1               5                   10                  15
```

<210> SEQ ID NO 862
<211> LENGTH: 15
<212> TYPE: PRT
<213> ORGANISM: Homo sapiens

<400> SEQUENCE: 862

```
Ile Pro Pro Asp Val Glu Glu Lys Leu Arg Leu Glu Trp Pro Tyr
1               5                   10                  15
```

<210> SEQ ID NO 863
<211> LENGTH: 15
<212> TYPE: PRT
<213> ORGANISM: Homo sapiens

<400> SEQUENCE: 863

```
Pro Asp Val Glu Glu Lys Leu Arg Leu Glu Trp Pro Tyr Gln Glu
1               5                   10                  15
```

-continued

<210> SEQ ID NO 864
<211> LENGTH: 15
<212> TYPE: PRT
<213> ORGANISM: Homo sapiens

<400> SEQUENCE: 864

Glu Lys Leu Arg Leu Glu Trp Pro Tyr Gln Glu Gln Leu Leu Leu
1               5                   10                  15

<210> SEQ ID NO 865
<211> LENGTH: 15
<212> TYPE: PRT
<213> ORGANISM: Homo sapiens

<400> SEQUENCE: 865

Leu Arg Leu Glu Trp Pro Tyr Gln Glu Gln Leu Leu Leu Arg Glu
1               5                   10                  15

<210> SEQ ID NO 866
<211> LENGTH: 15
<212> TYPE: PRT
<213> ORGANISM: Homo sapiens

<400> SEQUENCE: 866

Leu Glu Trp Pro Tyr Gln Glu Gln Leu Leu Leu Arg Glu His Tyr
1               5                   10                  15

<210> SEQ ID NO 867
<211> LENGTH: 15
<212> TYPE: PRT
<213> ORGANISM: Homo sapiens

<400> SEQUENCE: 867

Trp Pro Tyr Gln Glu Gln Leu Leu Leu Arg Glu His Tyr Gln Lys
1               5                   10                  15

<210> SEQ ID NO 868
<211> LENGTH: 15
<212> TYPE: PRT
<213> ORGANISM: Homo sapiens

<400> SEQUENCE: 868

Leu Leu Leu Arg Glu His Tyr Gln Lys Lys Phe Lys Asn Ser Thr
1               5                   10                  15

<210> SEQ ID NO 869
<211> LENGTH: 15
<212> TYPE: PRT
<213> ORGANISM: Homo sapiens

<400> SEQUENCE: 869

Leu Leu Arg Glu His Tyr Gln Lys Lys Phe Lys Asn Ser Thr Tyr
1               5                   10                  15

<210> SEQ ID NO 870
<211> LENGTH: 15
<212> TYPE: PRT
<213> ORGANISM: Homo sapiens

<400> SEQUENCE: 870

Tyr Gln Lys Lys Phe Lys Asn Ser Thr Tyr Ser Arg Ser Ser Val
1               5                   10                  15

<210> SEQ ID NO 871

```
<211> LENGTH: 15
<212> TYPE: PRT
<213> ORGANISM: Homo sapiens

<400> SEQUENCE: 871

Phe Lys Asn Ser Thr Tyr Ser Arg Ser Ser Val Asp Val Leu Tyr
1               5                   10                  15

<210> SEQ ID NO 872
<211> LENGTH: 15
<212> TYPE: PRT
<213> ORGANISM: Homo sapiens

<400> SEQUENCE: 872

Tyr Ser Arg Ser Ser Val Asp Val Leu Tyr Thr Phe Ala Asn Cys
1               5                   10                  15

<210> SEQ ID NO 873
<211> LENGTH: 15
<212> TYPE: PRT
<213> ORGANISM: Homo sapiens

<400> SEQUENCE: 873

Val Leu Tyr Thr Phe Ala Asn Cys Ser Gly Leu Asp Leu Ile Phe
1               5                   10                  15

<210> SEQ ID NO 874
<211> LENGTH: 15
<212> TYPE: PRT
<213> ORGANISM: Homo sapiens

<400> SEQUENCE: 874

Tyr Thr Phe Ala Asn Cys Ser Gly Leu Asp Leu Ile Phe Gly Leu
1               5                   10                  15

<210> SEQ ID NO 875
<211> LENGTH: 15
<212> TYPE: PRT
<213> ORGANISM: Homo sapiens

<400> SEQUENCE: 875

Phe Ala Asn Cys Ser Gly Leu Asp Leu Ile Phe Gly Leu Asn Ala
1               5                   10                  15

<210> SEQ ID NO 876
<211> LENGTH: 15
<212> TYPE: PRT
<213> ORGANISM: Homo sapiens

<400> SEQUENCE: 876

Gln Trp Asn Ser Ser Asn Ala Gln Leu Leu Leu Asp Tyr Cys Ser
1               5                   10                  15

<210> SEQ ID NO 877
<211> LENGTH: 15
<212> TYPE: PRT
<213> ORGANISM: Homo sapiens

<400> SEQUENCE: 877

Asn Ser Ser Asn Ala Gln Leu Leu Leu Asp Tyr Cys Ser Ser Lys
1               5                   10                  15

<210> SEQ ID NO 878
<211> LENGTH: 15
<212> TYPE: PRT
```

-continued

<213> ORGANISM: Homo sapiens

<400> SEQUENCE: 878

Leu Leu Leu Asp Tyr Cys Ser Ser Lys Gly Tyr Asn Ile Ser Trp
1               5                   10                  15

<210> SEQ ID NO 879
<211> LENGTH: 15
<212> TYPE: PRT
<213> ORGANISM: Homo sapiens

<400> SEQUENCE: 879

Asp Tyr Cys Ser Ser Lys Gly Tyr Asn Ile Ser Trp Glu Leu Gly
1               5                   10                  15

<210> SEQ ID NO 880
<211> LENGTH: 15
<212> TYPE: PRT
<213> ORGANISM: Homo sapiens

<400> SEQUENCE: 880

Ser Ser Lys Gly Tyr Asn Ile Ser Trp Glu Leu Gly Asn Glu Pro
1               5                   10                  15

<210> SEQ ID NO 881
<211> LENGTH: 15
<212> TYPE: PRT
<213> ORGANISM: Homo sapiens

<400> SEQUENCE: 881

Glu Leu Gly Asn Glu Pro Asn Ser Phe Leu Lys Lys Ala Asp Ile
1               5                   10                  15

<210> SEQ ID NO 882
<211> LENGTH: 15
<212> TYPE: PRT
<213> ORGANISM: Homo sapiens

<400> SEQUENCE: 882

Leu Gly Asn Glu Pro Asn Ser Phe Leu Lys Lys Ala Asp Ile Phe
1               5                   10                  15

<210> SEQ ID NO 883
<211> LENGTH: 15
<212> TYPE: PRT
<213> ORGANISM: Homo sapiens

<400> SEQUENCE: 883

Gly Asn Glu Pro Asn Ser Phe Leu Lys Lys Ala Asp Ile Phe Ile
1               5                   10                  15

<210> SEQ ID NO 884
<211> LENGTH: 15
<212> TYPE: PRT
<213> ORGANISM: Homo sapiens

<400> SEQUENCE: 884

Ser Phe Leu Lys Lys Ala Asp Ile Phe Ile Asn Gly Ser Gln Leu
1               5                   10                  15

<210> SEQ ID NO 885
<211> LENGTH: 15
<212> TYPE: PRT
<213> ORGANISM: Homo sapiens

<400> SEQUENCE: 885

Ile Asn Gly Ser Gln Leu Gly Glu Asp Phe Ile Gln Leu His Lys
1               5                   10                  15

<210> SEQ ID NO 886
<211> LENGTH: 15
<212> TYPE: PRT
<213> ORGANISM: Homo sapiens

<400> SEQUENCE: 886

Ile Gln Leu His Lys Leu Leu Arg Lys Ser Thr Phe Lys Asn Ala
1               5                   10                  15

<210> SEQ ID NO 887
<211> LENGTH: 15
<212> TYPE: PRT
<213> ORGANISM: Homo sapiens

<400> SEQUENCE: 887

Lys Leu Leu Arg Lys Ser Thr Phe Lys Asn Ala Lys Leu Tyr Gly
1               5                   10                  15

<210> SEQ ID NO 888
<211> LENGTH: 15
<212> TYPE: PRT
<213> ORGANISM: Homo sapiens

<400> SEQUENCE: 888

Lys Asn Ala Lys Leu Tyr Gly Pro Asp Val Gly Gln Pro Arg Arg
1               5                   10                  15

<210> SEQ ID NO 889
<211> LENGTH: 15
<212> TYPE: PRT
<213> ORGANISM: Homo sapiens

<400> SEQUENCE: 889

Leu Tyr Gly Pro Asp Val Gly Gln Pro Arg Arg Lys Thr Ala Lys
1               5                   10                  15

<210> SEQ ID NO 890
<211> LENGTH: 15
<212> TYPE: PRT
<213> ORGANISM: Homo sapiens

<400> SEQUENCE: 890

Gly Gln Pro Arg Arg Lys Thr Ala Lys Met Leu Lys Ser Phe Leu
1               5                   10                  15

<210> SEQ ID NO 891
<211> LENGTH: 15
<212> TYPE: PRT
<213> ORGANISM: Homo sapiens

<400> SEQUENCE: 891

Arg Arg Lys Thr Ala Lys Met Leu Lys Ser Phe Leu Lys Ala Gly
1               5                   10                  15

<210> SEQ ID NO 892
<211> LENGTH: 15
<212> TYPE: PRT
<213> ORGANISM: Homo sapiens

<400> SEQUENCE: 892

-continued

```
Lys Met Lys Ser Phe Leu Lys Ala Gly Gly Glu Val Ile Asp
1               5                   10                  15

<210> SEQ ID NO 893
<211> LENGTH: 15
<212> TYPE: PRT
<213> ORGANISM: Homo sapiens

<400> SEQUENCE: 893

Ser Phe Leu Lys Ala Gly Gly Glu Val Ile Asp Ser Val Thr Trp
1               5                   10                  15

<210> SEQ ID NO 894
<211> LENGTH: 15
<212> TYPE: PRT
<213> ORGANISM: Homo sapiens

<400> SEQUENCE: 894

Ala Gly Gly Glu Val Ile Asp Ser Val Thr Trp His His Tyr Tyr
1               5                   10                  15

<210> SEQ ID NO 895
<211> LENGTH: 15
<212> TYPE: PRT
<213> ORGANISM: Homo sapiens

<400> SEQUENCE: 895

Glu Val Ile Asp Ser Val Thr Trp His His Tyr Tyr Leu Asn Gly
1               5                   10                  15

<210> SEQ ID NO 896
<211> LENGTH: 15
<212> TYPE: PRT
<213> ORGANISM: Homo sapiens

<400> SEQUENCE: 896

Tyr Tyr Leu Asn Gly Arg Thr Ala Thr Arg Glu Asp Phe Leu Asn
1               5                   10                  15

<210> SEQ ID NO 897
<211> LENGTH: 15
<212> TYPE: PRT
<213> ORGANISM: Homo sapiens

<400> SEQUENCE: 897

Leu Asn Gly Arg Thr Ala Thr Arg Glu Asp Phe Leu Asn Pro Asp
1               5                   10                  15

<210> SEQ ID NO 898
<211> LENGTH: 15
<212> TYPE: PRT
<213> ORGANISM: Homo sapiens

<400> SEQUENCE: 898

Gly Arg Thr Ala Thr Arg Glu Asp Phe Leu Asn Pro Asp Val Leu
1               5                   10                  15

<210> SEQ ID NO 899
<211> LENGTH: 15
<212> TYPE: PRT
<213> ORGANISM: Homo sapiens

<400> SEQUENCE: 899

Arg Thr Ala Thr Arg Glu Asp Phe Leu Asn Pro Asp Val Leu Asp
1               5                   10                  15
```

```
<210> SEQ ID NO 900
<211> LENGTH: 15
<212> TYPE: PRT
<213> ORGANISM: Homo sapiens

<400> SEQUENCE: 900

Ile Phe Ile Ser Ser Val Gln Lys Val Phe Gln Val Val Glu Ser
1               5                   10                  15

<210> SEQ ID NO 901
<211> LENGTH: 15
<212> TYPE: PRT
<213> ORGANISM: Homo sapiens

<400> SEQUENCE: 901

Ser Val Gln Lys Val Phe Gln Val Val Glu Ser Thr Arg Pro Gly
1               5                   10                  15

<210> SEQ ID NO 902
<211> LENGTH: 15
<212> TYPE: PRT
<213> ORGANISM: Homo sapiens

<400> SEQUENCE: 902

Val Glu Ser Thr Arg Pro Gly Lys Lys Val Trp Leu Gly Glu Thr
1               5                   10                  15

<210> SEQ ID NO 903
<211> LENGTH: 15
<212> TYPE: PRT
<213> ORGANISM: Homo sapiens

<400> SEQUENCE: 903

Arg Pro Gly Lys Lys Val Trp Leu Gly Glu Thr Ser Ser Ala Tyr
1               5                   10                  15

<210> SEQ ID NO 904
<211> LENGTH: 15
<212> TYPE: PRT
<213> ORGANISM: Homo sapiens

<400> SEQUENCE: 904

Glu Thr Ser Ser Ala Tyr Gly Gly Gly Ala Pro Leu Leu Ser Asp
1               5                   10                  15

<210> SEQ ID NO 905
<211> LENGTH: 15
<212> TYPE: PRT
<213> ORGANISM: Homo sapiens

<400> SEQUENCE: 905

Thr Ser Ser Ala Tyr Gly Gly Gly Ala Pro Leu Leu Ser Asp Thr
1               5                   10                  15

<210> SEQ ID NO 906
<211> LENGTH: 15
<212> TYPE: PRT
<213> ORGANISM: Homo sapiens

<400> SEQUENCE: 906

Ser Ala Tyr Gly Gly Gly Ala Pro Leu Leu Ser Asp Thr Phe Ala
1               5                   10                  15
```

```
<210> SEQ ID NO 907
<211> LENGTH: 15
<212> TYPE: PRT
<213> ORGANISM: Homo sapiens

<400> SEQUENCE: 907

Ala Tyr Gly Gly Gly Ala Pro Leu Leu Ser Asp Thr Phe Ala Ala
1               5                   10                  15

<210> SEQ ID NO 908
<211> LENGTH: 15
<212> TYPE: PRT
<213> ORGANISM: Homo sapiens

<400> SEQUENCE: 908

Leu Leu Ser Asp Thr Phe Ala Ala Gly Phe Met Trp Leu Asp Lys
1               5                   10                  15

<210> SEQ ID NO 909
<211> LENGTH: 15
<212> TYPE: PRT
<213> ORGANISM: Homo sapiens

<400> SEQUENCE: 909

Thr Phe Ala Ala Gly Phe Met Trp Leu Asp Lys Leu Gly Leu Ser
1               5                   10                  15

<210> SEQ ID NO 910
<211> LENGTH: 15
<212> TYPE: PRT
<213> ORGANISM: Homo sapiens

<400> SEQUENCE: 910

Trp Leu Asp Lys Leu Gly Leu Ser Ala Arg Met Gly Ile Glu Val
1               5                   10                  15

<210> SEQ ID NO 911
<211> LENGTH: 15
<212> TYPE: PRT
<213> ORGANISM: Homo sapiens

<400> SEQUENCE: 911

Asp Lys Leu Gly Leu Ser Ala Arg Met Gly Ile Glu Val Val Met
1               5                   10                  15

<210> SEQ ID NO 912
<211> LENGTH: 15
<212> TYPE: PRT
<213> ORGANISM: Homo sapiens

<400> SEQUENCE: 912

Leu Gly Leu Ser Ala Arg Met Gly Ile Glu Val Val Met Arg Gln
1               5                   10                  15

<210> SEQ ID NO 913
<211> LENGTH: 15
<212> TYPE: PRT
<213> ORGANISM: Homo sapiens

<400> SEQUENCE: 913

Gly Leu Ser Ala Arg Met Gly Ile Glu Val Val Met Arg Gln Val
1               5                   10                  15

<210> SEQ ID NO 914
<211> LENGTH: 15
```

<212> TYPE: PRT
<213> ORGANISM: Homo sapiens

<400> SEQUENCE: 914

Leu Ser Ala Arg Met Gly Ile Glu Val Val Met Arg Gln Val Phe
1               5                   10                  15

<210> SEQ ID NO 915
<211> LENGTH: 15
<212> TYPE: PRT
<213> ORGANISM: Homo sapiens

<400> SEQUENCE: 915

Met Gly Ile Glu Val Val Met Arg Gln Val Phe Phe Gly Ala Gly
1               5                   10                  15

<210> SEQ ID NO 916
<211> LENGTH: 15
<212> TYPE: PRT
<213> ORGANISM: Homo sapiens

<400> SEQUENCE: 916

Val Met Arg Gln Val Phe Phe Gly Ala Gly Asn Tyr His Leu Val
1               5                   10                  15

<210> SEQ ID NO 917
<211> LENGTH: 15
<212> TYPE: PRT
<213> ORGANISM: Homo sapiens

<400> SEQUENCE: 917

Val Phe Phe Gly Ala Gly Asn Tyr His Leu Val Asp Glu Asn Phe
1               5                   10                  15

<210> SEQ ID NO 918
<211> LENGTH: 15
<212> TYPE: PRT
<213> ORGANISM: Homo sapiens

<400> SEQUENCE: 918

Phe Gly Ala Gly Asn Tyr His Leu Val Asp Glu Asn Phe Asp Pro
1               5                   10                  15

<210> SEQ ID NO 919
<211> LENGTH: 15
<212> TYPE: PRT
<213> ORGANISM: Homo sapiens

<400> SEQUENCE: 919

Gly Ala Gly Asn Tyr His Leu Val Asp Glu Asn Phe Asp Pro Leu
1               5                   10                  15

<210> SEQ ID NO 920
<211> LENGTH: 15
<212> TYPE: PRT
<213> ORGANISM: Homo sapiens

<400> SEQUENCE: 920

His Leu Val Asp Glu Asn Phe Asp Pro Leu Pro Asp Tyr Trp Leu
1               5                   10                  15

<210> SEQ ID NO 921
<211> LENGTH: 15
<212> TYPE: PRT
<213> ORGANISM: Homo sapiens

```
<400> SEQUENCE: 921

Leu Val Asp Glu Asn Phe Asp Pro Leu Pro Asp Tyr Trp Leu Ser
1               5                   10                  15

<210> SEQ ID NO 922
<211> LENGTH: 15
<212> TYPE: PRT
<213> ORGANISM: Homo sapiens

<400> SEQUENCE: 922

Glu Asn Phe Asp Pro Leu Pro Asp Tyr Trp Leu Ser Leu Leu Phe
1               5                   10                  15

<210> SEQ ID NO 923
<211> LENGTH: 15
<212> TYPE: PRT
<213> ORGANISM: Homo sapiens

<400> SEQUENCE: 923

Asp Pro Leu Pro Asp Tyr Trp Leu Ser Leu Leu Phe Lys Lys Leu
1               5                   10                  15

<210> SEQ ID NO 924
<211> LENGTH: 15
<212> TYPE: PRT
<213> ORGANISM: Homo sapiens

<400> SEQUENCE: 924

Tyr Trp Leu Ser Leu Leu Phe Lys Lys Leu Val Gly Thr Lys Val
1               5                   10                  15

<210> SEQ ID NO 925
<211> LENGTH: 15
<212> TYPE: PRT
<213> ORGANISM: Homo sapiens

<400> SEQUENCE: 925

Leu Phe Lys Lys Leu Val Gly Thr Lys Val Leu Met Ala Ser Val
1               5                   10                  15

<210> SEQ ID NO 926
<211> LENGTH: 15
<212> TYPE: PRT
<213> ORGANISM: Homo sapiens

<400> SEQUENCE: 926

Val Gly Thr Lys Val Leu Met Ala Ser Val Gln Gly Ser Lys Arg
1               5                   10                  15

<210> SEQ ID NO 927
<211> LENGTH: 15
<212> TYPE: PRT
<213> ORGANISM: Homo sapiens

<400> SEQUENCE: 927

Val Leu Met Ala Ser Val Gln Gly Ser Lys Arg Arg Lys Leu Arg
1               5                   10                  15

<210> SEQ ID NO 928
<211> LENGTH: 15
<212> TYPE: PRT
<213> ORGANISM: Homo sapiens

<400> SEQUENCE: 928
```

```
Leu Met Ala Ser Val Gln Gly Ser Lys Arg Arg Lys Leu Arg Val
1               5                   10                  15

<210> SEQ ID NO 929
<211> LENGTH: 15
<212> TYPE: PRT
<213> ORGANISM: Homo sapiens

<400> SEQUENCE: 929

Gly Ser Lys Arg Arg Lys Leu Arg Val Tyr Leu His Cys Thr Asn
1               5                   10                  15

<210> SEQ ID NO 930
<211> LENGTH: 15
<212> TYPE: PRT
<213> ORGANISM: Homo sapiens

<400> SEQUENCE: 930

Tyr Leu His Cys Thr Asn Thr Asp Asn Pro Arg Tyr Lys Glu Gly
1               5                   10                  15

<210> SEQ ID NO 931
<211> LENGTH: 15
<212> TYPE: PRT
<213> ORGANISM: Homo sapiens

<400> SEQUENCE: 931

His Cys Thr Asn Thr Asp Asn Pro Arg Tyr Lys Glu Gly Asp Leu
1               5                   10                  15

<210> SEQ ID NO 932
<211> LENGTH: 15
<212> TYPE: PRT
<213> ORGANISM: Homo sapiens

<400> SEQUENCE: 932

Asn Thr Asp Asn Pro Arg Tyr Lys Glu Gly Asp Leu Thr Leu Tyr
1               5                   10                  15

<210> SEQ ID NO 933
<211> LENGTH: 15
<212> TYPE: PRT
<213> ORGANISM: Homo sapiens

<400> SEQUENCE: 933

Tyr Lys Glu Gly Asp Leu Thr Leu Tyr Ala Ile Asn Leu His Asn
1               5                   10                  15

<210> SEQ ID NO 934
<211> LENGTH: 15
<212> TYPE: PRT
<213> ORGANISM: Homo sapiens

<400> SEQUENCE: 934

Ile Asn Leu His Asn Val Thr Lys Tyr Leu Arg Leu Pro Tyr Pro
1               5                   10                  15

<210> SEQ ID NO 935
<211> LENGTH: 15
<212> TYPE: PRT
<213> ORGANISM: Homo sapiens

<400> SEQUENCE: 935

His Asn Val Thr Lys Tyr Leu Arg Leu Pro Tyr Pro Phe Ser Asn
```

-continued

```
1               5                   10                  15

<210> SEQ ID NO 936
<211> LENGTH: 15
<212> TYPE: PRT
<213> ORGANISM: Homo sapiens

<400> SEQUENCE: 936

Lys Tyr Leu Arg Leu Pro Tyr Pro Phe Ser Asn Lys Gln Val Asp
1               5                   10                  15

<210> SEQ ID NO 937
<211> LENGTH: 15
<212> TYPE: PRT
<213> ORGANISM: Homo sapiens

<400> SEQUENCE: 937

Tyr Pro Phe Ser Asn Lys Gln Val Asp Lys Tyr Leu Leu Arg Pro
1               5                   10                  15

<210> SEQ ID NO 938
<211> LENGTH: 15
<212> TYPE: PRT
<213> ORGANISM: Homo sapiens

<400> SEQUENCE: 938

Phe Ser Asn Lys Gln Val Asp Lys Tyr Leu Leu Arg Pro Leu Gly
1               5                   10                  15

<210> SEQ ID NO 939
<211> LENGTH: 15
<212> TYPE: PRT
<213> ORGANISM: Homo sapiens

<400> SEQUENCE: 939

Gln Val Asp Lys Tyr Leu Leu Arg Pro Leu Gly Pro His Gly Leu
1               5                   10                  15

<210> SEQ ID NO 940
<211> LENGTH: 15
<212> TYPE: PRT
<213> ORGANISM: Homo sapiens

<400> SEQUENCE: 940

Leu Leu Arg Pro Leu Gly Pro His Gly Leu Leu Ser Lys Ser Val
1               5                   10                  15

<210> SEQ ID NO 941
<211> LENGTH: 15
<212> TYPE: PRT
<213> ORGANISM: Homo sapiens

<400> SEQUENCE: 941

Arg Pro Leu Gly Pro His Gly Leu Leu Ser Lys Ser Val Gln Leu
1               5                   10                  15

<210> SEQ ID NO 942
<211> LENGTH: 15
<212> TYPE: PRT
<213> ORGANISM: Homo sapiens

<400> SEQUENCE: 942

Gln Leu Asn Gly Leu Thr Leu Lys Met Val Asp Asp Gln Thr Leu
1               5                   10                  15
```

```
<210> SEQ ID NO 943
<211> LENGTH: 15
<212> TYPE: PRT
<213> ORGANISM: Homo sapiens

<400> SEQUENCE: 943

Asn Gly Leu Thr Leu Lys Met Val Asp Asp Gln Thr Leu Pro Pro
1               5                   10                  15

<210> SEQ ID NO 944
<211> LENGTH: 15
<212> TYPE: PRT
<213> ORGANISM: Homo sapiens

<400> SEQUENCE: 944

Lys Met Val Asp Asp Gln Thr Leu Pro Pro Leu Met Glu Lys Pro
1               5                   10                  15

<210> SEQ ID NO 945
<211> LENGTH: 15
<212> TYPE: PRT
<213> ORGANISM: Homo sapiens

<400> SEQUENCE: 945

Met Val Asp Asp Gln Thr Leu Pro Pro Leu Met Glu Lys Pro Leu
1               5                   10                  15

<210> SEQ ID NO 946
<211> LENGTH: 15
<212> TYPE: PRT
<213> ORGANISM: Homo sapiens

<400> SEQUENCE: 946

Val Asp Asp Gln Thr Leu Pro Pro Leu Met Glu Lys Pro Leu Arg
1               5                   10                  15

<210> SEQ ID NO 947
<211> LENGTH: 15
<212> TYPE: PRT
<213> ORGANISM: Homo sapiens

<400> SEQUENCE: 947

Thr Leu Pro Pro Leu Met Glu Lys Pro Leu Arg Pro Gly Ser Ser
1               5                   10                  15

<210> SEQ ID NO 948
<211> LENGTH: 15
<212> TYPE: PRT
<213> ORGANISM: Homo sapiens

<400> SEQUENCE: 948

Met Glu Lys Pro Leu Arg Pro Gly Ser Ser Leu Gly Leu Pro Ala
1               5                   10                  15

<210> SEQ ID NO 949
<211> LENGTH: 15
<212> TYPE: PRT
<213> ORGANISM: Homo sapiens

<400> SEQUENCE: 949

Pro Leu Arg Pro Gly Ser Ser Leu Gly Leu Pro Ala Phe Ser Tyr
1               5                   10                  15

<210> SEQ ID NO 950
```

```
<211> LENGTH: 15
<212> TYPE: PRT
<213> ORGANISM: Homo sapiens

<400> SEQUENCE: 950

Leu Arg Pro Gly Ser Ser Leu Gly Leu Pro Ala Phe Ser Tyr Ser
1               5                   10                  15

<210> SEQ ID NO 951
<211> LENGTH: 15
<212> TYPE: PRT
<213> ORGANISM: Homo sapiens

<400> SEQUENCE: 951

Arg Pro Gly Ser Ser Leu Gly Leu Pro Ala Phe Ser Tyr Ser Phe
1               5                   10                  15

<210> SEQ ID NO 952
<211> LENGTH: 15
<212> TYPE: PRT
<213> ORGANISM: Homo sapiens

<400> SEQUENCE: 952

Pro Gly Ser Ser Leu Gly Leu Pro Ala Phe Ser Tyr Ser Phe Phe
1               5                   10                  15

<210> SEQ ID NO 953
<211> LENGTH: 15
<212> TYPE: PRT
<213> ORGANISM: Homo sapiens

<400> SEQUENCE: 953

Gly Leu Pro Ala Phe Ser Tyr Ser Phe Phe Val Ile Arg Asn Ala
1               5                   10                  15

<210> SEQ ID NO 954
<211> LENGTH: 15
<212> TYPE: PRT
<213> ORGANISM: Homo sapiens

<400> SEQUENCE: 954

Phe Leu Ile Phe Asp Pro Lys Lys Glu Ser Thr Phe Glu Glu Arg
1               5                   10                  15

<210> SEQ ID NO 955
<211> LENGTH: 15
<212> TYPE: PRT
<213> ORGANISM: Homo sapiens

<400> SEQUENCE: 955

Pro Tyr Pro Phe Ser Asn Lys Gln Val Asp Lys Tyr Leu Leu Arg
1               5                   10                  15

<210> SEQ ID NO 956
<211> LENGTH: 15
<212> TYPE: PRT
<213> ORGANISM: Homo sapiens

<400> SEQUENCE: 956

Val Asp Lys Tyr Leu Leu Arg Pro Leu Gly Pro His Gly Leu Leu
1               5                   10                  15

<210> SEQ ID NO 957
<211> LENGTH: 15
<212> TYPE: PRT
```

<213> ORGANISM: Homo sapiens

<400> SEQUENCE: 957

His Tyr Tyr Leu Asn Gly Arg Thr Ala Thr Arg Glu Asp Phe Leu
1               5                   10                  15

<210> SEQ ID NO 958
<211> LENGTH: 15
<212> TYPE: PRT
<213> ORGANISM: Homo sapiens

<400> SEQUENCE: 958

Gly Ile Glu Val Val Met Arg Gln Val Phe Phe Gly Ala Gly Asn
1               5                   10                  15

<210> SEQ ID NO 959
<211> LENGTH: 15
<212> TYPE: PRT
<213> ORGANISM: Homo sapiens

<400> SEQUENCE: 959

Leu Pro Pro Leu Met Glu Lys Pro Leu Arg Pro Gly Ser Ser Leu
1               5                   10                  15

<210> SEQ ID NO 960
<211> LENGTH: 15
<212> TYPE: PRT
<213> ORGANISM: Homo sapiens

<400> SEQUENCE: 960

Ser Pro Gly Ala Leu Pro Arg Pro Ala Gln Ala Gln Asp Val Val
1               5                   10                  15

<210> SEQ ID NO 961
<211> LENGTH: 15
<212> TYPE: PRT
<213> ORGANISM: Homo sapiens

<400> SEQUENCE: 961

Asn Leu Ala Thr Asp Pro Arg Phe Leu Ile Leu Leu Gly Ser Pro
1               5                   10                  15

<210> SEQ ID NO 962
<211> LENGTH: 15
<212> TYPE: PRT
<213> ORGANISM: Homo sapiens

<400> SEQUENCE: 962

Lys Leu Arg Thr Leu Ala Arg Gly Leu Ser Pro Ala Tyr Leu Arg
1               5                   10                  15

<210> SEQ ID NO 963
<211> LENGTH: 15
<212> TYPE: PRT
<213> ORGANISM: Homo sapiens

<400> SEQUENCE: 963

Leu Ser Pro Ala Tyr Leu Arg Phe Gly Gly Thr Lys Thr Asp Phe
1               5                   10                  15

<210> SEQ ID NO 964
<211> LENGTH: 15
<212> TYPE: PRT
<213> ORGANISM: Homo sapiens -continued

```
<400> SEQUENCE: 964

Leu Arg Phe Gly Gly Thr Lys Thr Asp Phe Leu Ile Phe Asp Pro
1               5                   10                  15

<210> SEQ ID NO 965
<211> LENGTH: 15
<212> TYPE: PRT
<213> ORGANISM: Homo sapiens

<400> SEQUENCE: 965

Leu Ile Phe Asp Pro Lys Lys Glu Ser Thr Phe Glu Glu Arg Ser
1               5                   10                  15

<210> SEQ ID NO 966
<211> LENGTH: 15
<212> TYPE: PRT
<213> ORGANISM: Homo sapiens

<400> SEQUENCE: 966

Leu Arg Glu His Tyr Gln Lys Lys Phe Lys Asn Ser Thr Tyr Ser
1               5                   10                  15

<210> SEQ ID NO 967
<211> LENGTH: 15
<212> TYPE: PRT
<213> ORGANISM: Homo sapiens

<400> SEQUENCE: 967

Gly Leu Asn Ala Leu Leu Arg Thr Ala Asp Leu Gln Trp Asn Ser
1               5                   10                  15

<210> SEQ ID NO 968
<211> LENGTH: 15
<212> TYPE: PRT
<213> ORGANISM: Homo sapiens

<400> SEQUENCE: 968

Leu Asp Tyr Cys Ser Ser Lys Gly Tyr Asn Ile Ser Trp Glu Leu
1               5                   10                  15

<210> SEQ ID NO 969
<211> LENGTH: 15
<212> TYPE: PRT
<213> ORGANISM: Homo sapiens

<400> SEQUENCE: 969

Asp Phe Ile Gln Leu His Lys Leu Leu Arg Lys Ser Thr Phe Lys
1               5                   10                  15

<210> SEQ ID NO 970
<211> LENGTH: 15
<212> TYPE: PRT
<213> ORGANISM: Homo sapiens

<400> SEQUENCE: 970

Pro Asp Val Gly Gln Pro Arg Arg Lys Thr Ala Lys Met Leu Lys
1               5                   10                  15

<210> SEQ ID NO 971
<211> LENGTH: 15
<212> TYPE: PRT
<213> ORGANISM: Homo sapiens

<400> SEQUENCE: 971
```

-continued

Val Gly Gln Pro Arg Lys Thr Ala Lys Met Leu Lys Ser Phe
1               5                   10                  15

<210> SEQ ID NO 972
<211> LENGTH: 15
<212> TYPE: PRT
<213> ORGANISM: Homo sapiens

<400> SEQUENCE: 972

Lys Thr Ala Lys Met Leu Lys Ser Phe Leu Lys Ala Gly Gly Glu
1               5                   10                  15

<210> SEQ ID NO 973
<211> LENGTH: 15
<212> TYPE: PRT
<213> ORGANISM: Homo sapiens

<400> SEQUENCE: 973

Met Leu Lys Ser Phe Leu Lys Ala Gly Gly Glu Val Ile Asp Ser
1               5                   10                  15

<210> SEQ ID NO 974
<211> LENGTH: 15
<212> TYPE: PRT
<213> ORGANISM: Homo sapiens

<400> SEQUENCE: 974

Asn Gly Arg Thr Ala Thr Arg Glu Asp Phe Leu Asn Pro Asp Val
1               5                   10                  15

<210> SEQ ID NO 975
<211> LENGTH: 15
<212> TYPE: PRT
<213> ORGANISM: Homo sapiens

<400> SEQUENCE: 975

Phe Ile Ser Ser Val Gln Lys Val Phe Gln Val Val Glu Ser Thr
1               5                   10                  15

<210> SEQ ID NO 976
<211> LENGTH: 15
<212> TYPE: PRT
<213> ORGANISM: Homo sapiens

<400> SEQUENCE: 976

Gln Val Val Glu Ser Thr Arg Pro Gly Lys Lys Val Trp Leu Gly
1               5                   10                  15

<210> SEQ ID NO 977
<211> LENGTH: 15
<212> TYPE: PRT
<213> ORGANISM: Homo sapiens

<400> SEQUENCE: 977

Ala Ser Val Gln Gly Ser Lys Arg Arg Lys Leu Arg Val Tyr Leu
1               5                   10                  15

<210> SEQ ID NO 978
<211> LENGTH: 15
<212> TYPE: PRT
<213> ORGANISM: Homo sapiens

<400> SEQUENCE: 978

Ser Val Gln Gly Ser Lys Arg Arg Lys Leu Arg Val Tyr Leu His
1               5                   10                  15

```
<210> SEQ ID NO 979
<211> LENGTH: 15
<212> TYPE: PRT
<213> ORGANISM: Homo sapiens

<400> SEQUENCE: 979

Thr Asp Asn Pro Arg Tyr Lys Glu Gly Asp Leu Thr Leu Tyr Ala
1               5                   10                  15

<210> SEQ ID NO 980
<211> LENGTH: 15
<212> TYPE: PRT
<213> ORGANISM: Homo sapiens

<400> SEQUENCE: 980

Leu Met Glu Lys Pro Leu Arg Pro Gly Ser Ser Leu Gly Leu Pro
1               5                   10                  15

<210> SEQ ID NO 981
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Ala Leu Pro Pro Pro Leu Met Leu Leu
1               5

<210> SEQ ID NO 982
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Leu Leu Leu Gly Pro Leu Gly Pro Leu
1               5

<210> SEQ ID NO 983
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Asp Leu Ile Phe Gly Leu Asn Ala Leu
1               5

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

His Leu Val Glu Ala Leu Tyr Leu Val
1               5
```

```
<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Ser Leu Tyr Asn Thr Val Ala Thr Leu
1               5
```

HEPARANASE-DERIVED PEPTIDES FOR VACCINATION OF TUMOR PATIENTS

The present invention refers to nonapeptides derived from human heparanase which are useful for the therapeutic vaccination of tumor patients as well as for generating specific immune cells for cell therapies. Furthermore, the present nonapeptides can be employed in a method to increase the immune reaction of a patient against a key enzyme in metastasis.

The successful invasion of malignant tumor cells into the basement membrane represents an important step for the generation of tumor metastases. The basement membrane and the extracellular matrix (ECM) form the barriers between different tissues. These structures contain complex macromolecules, for example type IV-collagen, laminin, heparan sulfate-proteoglycan and fibronectin. The process of tumor invasion and metastasis involves a variety of proteinases which degrade said components of the ECM and the basement membrane and, as a consequence, enable the migration of foreign cells into the surrounding affected tissue or organ.

Heparan sulfate (HS) and heparan sulfate-proteoglycans (HSPG) are present on the extracellular surface and within the ECM. The HS-chains play a major role in cell to cell and cell to matrix interactions which are involved in various physiological and non-physiological processes. Examples of such processes are adhesion, migration, differentiation and proliferation of cells. Several molecules interact with HS and/or HSPG, like for example growth factors (e.g. FGF, PDGF; VEGF), cytokines (IL-2), extracellular matrix proteins (fibronectin, collagen), factors involved in hemostasis (heparin-cofactor II), or other molecules like e.g. lipoproteins, DNA topoisomerases and a β-amyloid proteins. Thus, it becomes evident that enzymes which modulate HS and/or HSPG may play a pivotal role in any of the above described processes.

A known HS/HSPG-modulating enzyme which has been identified in murine metastatic melanomal cells is heparanase, an endo-β-glucuronidase. Heparanase cleaves HS into characteristic fragments with a high molecular weight. This activity correlates with the metastatic potential of melanoma cells. An increased heparanase activity has also been demonstrated in other mobile, invasive cells, for example in relationship with lymphomas, mastocytomas, adenocarcinomas, leukemias and rheumatoid fibroblasts.

Based on the observations described in a prior art the problem underlying the present invention refers to the identification of new molecules that would interfere with heparanase expression and/or activity and, thus, prevent an undesired migration of cells into the neighboring tissue, like it is the case for metastases.

Heparanase-derived peptides and nucleic acids which may exhibit heparanase-inhibiting properties are known to the person skilled in the art. For example, WO 99/21975 describes an immunologically interactive molecule which is capable of binding to and/or inhibiting the catalytic activity of a heparanase polypeptide. WO-A 99/40207 discloses antagonists and inhibitors of heparanase which inhibit or eliminate the function of a heparanase polypeptide. As an example for an antagonist, an antibody against heparanase is described. As an example of an inhibitor, a small molecule inhibitor which inactivates heparanase by binding to and occupying the catalytic site, thereby making the catalytic site inaccessible to a substrate such that the biological activity of heparanase is prevented, is described. It is further illustrated in WO-A 99/40207 that such antagonists and inhibitors may be used to treat cancer, angiogenesis by preventing heparanase from functioning to breakdown extracellular matrix and release heparan sulfate from extracellular matrix and cell surface.

Furthermore, DE 199 55 803 describes heparanase inhibitors which inhibit the enzymatic activity of heparanase or its expression. According to the invention, these inhibitors bind to heparanase or to heparanase coding nucleic acids in order to be useful in the treatment of disfunctions of the heart.

In none of the documents known in the state of the art peptides were identified which can be employed for vaccination even though the tumor-associated antigen heparanase is highly over-expressed on the surface of tumor cells. Tumor vaccination represents an efficient therapy method which relies on the induction of a tumor-specific immune response. Through vaccination with tumor-specific antigens the own immune system should be enabled to recognize and destroy residual tumor cells. For example, lymphomas are successfully treated with this kind of therapy from the beginning of the eighties. It is known in the art that a vaccination with tumor-specific antigens increases the frequency of tumor-specific T-cells which mediate the destruction of the tumor carrying the antigen on the cellular surface.

Only a small portion of tumor patients possesses pre-formed memory T-cells against the tumor peptides known from the prior art (for example MUC1, or Her2neu). However, it could be assumed that successful therapeutic vaccination strategies may depend on the pre-valence of pre-formed peptide-specific memory T cells. A low number of memory T-cells may be the reason for a rather weak response of tumor patients to peptide vaccination described so far in the prior art.

It is therefore an object of the present invention to provide a vaccine against diseases, preferably tumor diseases, being accompanied with an increased heparanase expression, which overcome the disadvantages of the presently known vaccines namely the relatively weak induction of an immune response and the low abundance of memory T cells. The invention is based on the cognition that such a vaccine can be obtained by identifying heparanase-derived peptides which exhibit a high binding capacity to HLA-A2 (Human Leukocyte Antigen type A2), a type of so-called class I histocompatibility molecules (MHC class I). MHC class I molecules with bound peptides/antigens are commonly presented on the surface of cells, which are then recognized and destroyed by so-called cytotoxic T-cells ($CD8^+$-cells, $T_{KILLER}$ cells) of the immune system.

The applicant has identified characteristic nonapeptides derived from the heparanase molecule against which the majority of female patients with breast cancer possess pre-formed memory T-cells. In contrast, only for 10% of the same female patients memory T-cells with specificity against the currently used peptides derived from MUC1 and Her2neu antigens could be detected. Memory T-cells stay in a resting state, until encountering the peptide-MHC complex they recognize (e.g. during a re-infection with the same antigen), whereupon they become mature $CD8^+$-cells. This indicates a particular immunological relevance and a therapeutic potential of the peptides of the present invention.

Thus, the object of the present invention is a vaccine against a disease being associated with an enhanced heparanase expression and/or activity, wherein the vaccine contains a heparanase peptide, or a functional variant thereof, which binds to a HLA molecule. In a preferred embodiment of the present invention, the disease being associated with an enhanced heparanase expression and/or activity is a metastatic tumor.

The term "HLA molecule" encompasses both MHC class I and MHC class II molecules, both of which are encoded by at least three different HLA genes.

The person skilled in the art knows three HLA genes encoding MHC class I molecules: HLA-A, HLA-B and HLA-C, all of which are included in the present invention.

Preferably, the heparanase peptide binds to HLA-A-encoded molecules. Most preferred it binds to MHC class I molecules from the HLA-A2 allele, which is expressed on the cell surface of 50% of the Northern European population.

In an embodiment of the present invention, the vaccine contains at least one heparanase peptide selected from the group consisting of SEQ ID NOs: 1-505 (see also DRAWING, Table 1). Preferably, the vaccine contains at least one heparanase peptide selected from the group consisting of SEQ ID NOs: 1-187 (binding score 31 to 12). Even more preferably, the vaccine contains at least one heparanase peptide selected from the group consisting of SEQ ID NOs: 1-92 (binding score 31 to 16).

In the most preferred embodiment of the present invention, the vaccine contains at least one heparanase peptide selected from the group consisting of SEQ ID NOs: 1, 2, and 3 (binding score 31 to 28).

Another object of the present invention is a heparanase peptide, or a functional derivative thereof, that binds to HLA molecule, wherein the heparanase peptide is a nonapeptide having the sequence selected from the group consisting of heparanase peptide that binds to HLA molecule, wherein the heparanase peptide is a nonapeptide having the sequence selected from the group consisting of SEQ ID NOs:1-505, preferably SEQ ID NOs:1-187, more preferably SEQ ID NOs: 1-92 and most preferably SEQ ID NOs: 1-3.

Furthermore, the person skilled in the art is aware of three HLA genes encoding MHC class II molecules: HLA-DP, HLA-DQ and HLA-DR, all of which are included in the present invention. MHC class II molecules with bound peptides/antigens are also presented on the surface of antigen presenting cells; however, in contrast to MHC class I, these cells are then recognized by so-called helper T-cells (CD4$^+$-T cells) of the immune system. Thus, a heparanase peptide which binds to MHC class II molecules, as depicted e.g. in SEQ ID NOs: 506-980 (see also DRAWING, Table 2), induces a CD4$^+$-T cell—mediated immune response.

All three alleles of MHC class I molecules and all three alleles of MHC class II molecules are referred to hereinafter generally as "HLA" or "HLA molecules".

In the context of the present invention, a functional variant of a heparanase peptide comprises all compounds which induce an immune response according to the same effect of the heparanase peptide of the present invention.

More specifically, the functional variant can be a peptide, a fragment or derivative thereof, which differs from the heparanase peptide of the present invention in that one or more amino acids are either deleted, inserted, substituted or otherwise chemically modified (e.g. acetylated, phosphorylated, glycosylated, or myristoylated), provided that the property of the functional variant, namely the induction of T cell specific immune response by binding to HLA molecules is maintained. In this respect, the peptide can be extended or shortened on either the amino- or the carboxyterminal end or internally, or extended on one end and shortened on the other end, provided that the desired function as described is maintained.

It is also possible that the heparanase peptide of the present invention is conjugated or fused to one or more other peptides or lipids, which may confer a desired property to the heparanase peptide, e.g. for the detection or the purification of the heparanase peptide. For example, the heparanase peptide of the present invention can be fused to a so-called marker which enables the localization of the heparanase peptide in a cell or tissue. Suitable markers include "epitope tags" (like c-myc, hemagglutinin, FLAG-tag), biotin, digoxigenin, (strept-) avidin, Green Fluorescent Protein (GFP, and derivatives thereof), enzymes like horseradish peroxidase, alkaline phosphatase, beta-galactosidase, luciferase, beta-glucuronidase and beta-lactamase. Examples for fusion partners that allow for the purification of the heparanase peptide include HIS-tag and glutathion S transferase (GST).

For the present invention it can also be useful if the heparanase peptide is fused to an immunogenic carrier or moiety, which can be any macromolecule that enhances the immunogenicity of the vaccine. Examples of such immunogenic carriers include keyhole limpet hemocyanin (KLH), recombinant exoprotein A (rEPA), diphtheria protein CRM9 and tetanus toxoid (TT).

The conjugation or fusion of the heparanase peptide to any of the modifying compounds described supra can occur by any suitable method known to the skilled artisan, either by chemical or gene technological methods. The latter requires, that a nucleic acid coding for the whole fusion construct is inserted into an expression vector and expressed as an entity.

Furthermore, in order to deliver the heparanase peptide directly to or into the target cell it can be fused to a carrier peptide that mediates the cellular uptake of the peptide. Appropriate carriers are known to the person skilled in the art and include TAT, fibroblast growth factor, galparan (transportan), poly-arginine, and Pep-1. Furthermore, the heparanase peptide may be fused to a ligand for a cell surface receptor, or a functional portion thereof, and thus internalized by receptor-mediated endocytosis.

In a further embodiment, the functional variant of the heparanase peptide also encompasses nucleic acids, DNA or RNA, which encode the heparanase peptides, or their functional peptide variants, of the present invention. There are several well-known methods of introducing nucleic acids into animal cells, any of which may be used in the present invention and which depend on the host. Typical hosts include mammalian species, such as humans, non-human primates, dogs, cats, cattle, horses, sheep, and the like. At the simplest, the nucleic acid can be directly injected into the target cell/target tissue, or by so-called microinjection into the nucleus. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors, electroporation, and the like.

For the introduction of the heparanase peptide, respectively the nucleic acid encoding it, into the cell and its expression it can be advantageous if the nucleic acid is integrated in an expression vector. The expression vector is preferably a eukaryotic expression vector, or a retroviral vector, a plasmid, bacteriophage, or any other vector typically used in the biotechnology field. If necessary or desired, the nucleic acid encoding the heparanase peptide can be operatively linked to regulatory elements which direct the transcription and the synthesis of a translatable mRNA in pro- or eukaryotic cells. Such regulatory elements are promoters, enhancers or transcription termination signals, but can also comprise introns or similar elements, for example those, which promote or contribute to the stability and the amplification of the vector, the selection for successful delivery and/or the integration into the host's genome, like regions that promote homologous recombination at a desired site in the genome. For therapeutic purposes, the use of retroviral vectors has been proven to be most appropriate to deliver a desired nucleic acid into a target cell.

The cell to which the heparanase peptide, a functional variant thereof, or the nucleic acid encoding it, is applied to a professional antigen-presenting cell such as a B cell, a microphage or a dendritic cell, or any other cell within which the heparanase peptide can be loaded onto the HLA molecule and transported to the cell surface and presented as an antigen in order to induce the described immune response.

In particular, dendritic cells have been proven to be especially useful as vaccination "vehicles". Dendritic cells which are located in nearly all tissue types of the body incorporate a compound like heparanase peptide and migrate together with the lymph stream to the lymph node where they encounter with precursors of antigen-specific cytotoxic T cells. For the purposes of the present invention as well as for therapeutic purposes in general, dendritic cells can be generated and cultured in vitro by cultivating monocytes in the presence of Interleukin-4 (IL-4) and Granulocyte Macrophage Colony Stimulating Factor (GM-CSF). Alternatively, dendritic cell can be generated from $CD34^+$ haematopoietic stem cells of the periphery blood. By systematic application of growth factors, like e.g. Flt3 ligand, dendritic cells can also be expanded in the blood in vivo by several orders of magnitude. Isolated dendritic or other professional antigen-presenting cells can be loaded ("pulsed") with the heparanase peptide or the nucleic acid encoding it in order to enable the presentation of the heparanase peptide on the surface of these cells.

For the purpose of the present invention, dendritic or other cells carrying the heparanase peptide can be applied to a tumor patient by different methods of injection: (i) sub-/intracutanous, which requires migration to the lymph nodes; (ii) direct intranodal injection into a lymph node, circumventing the migration requirement; and (iii) intravenous injection.

Particularly useful to determine the frequency of heparanase peptide-specific $CD8^+$ T cells in immunised patients is the tetramer analysis. Such MHC tetramers are complexes of 4 MHC molecules which are associated with heparanase peptide and bound to a fluorochrome, e.g. phycoerythrin. The complexes bind to a distinct set of T cell receptors (TCRs) on the surface of $CD8^+$ T cells. Thus, by mixing tetramers with mononuclear cells from peripheral blood or bone marrow or whole blood of tumor patients and using flow cytometry as a detection system, a count of all T cells that are specific for heparanase is provided. The invention further includes the similar detection by using MHC dimers instead of tetramers.

The vaccine containing the heparanase peptide, a functional variant thereof, or the nucleic acid encoding it, as disclosed in the present invention can be used as a pharmaceutical. This is a further embodiment of the present invention.

The vaccine containing the heparanase peptide, a functional variant thereof, or the nucleic acid encoding it can be administered alone or in combination with one or more other active compounds which may aid to increase the immunogenicity of the vaccine. The latter can be administered before, after or simultaneously with the administration of the heparanase peptide, a functional variant thereof, or the nucleic acid encoding it. The dose of either the heparanase peptide, a functional variant thereof, or the nucleic acid encoding it or the active compound as well as the duration and the temperature of incubation can be variable and depends on the target that is to be treated.

A further object of the present invention are pharmaceutical preparations which comprise an effective dose of vaccine containing at least one heparanase peptide, a functional variant thereof, or the nucleic acid encoding it, optionally in combination with at least one active compound and a pharmaceutically acceptable carrier, i.e. one or more pharmaceutically acceptable carrier substances and/or additives.

The pharmaceutical/vaccine according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The preparation of the pharmaceutical compositions can be carried out in a manner known per se. To this end, the heparanase peptide, a functional variant thereof, or the nucleic acid encoding it and/or the active compound, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the heparanase peptide, a functional variant thereof, or the nucleic acid encoding it, and/or the active compound and to use the resulting lyophilisates, for example, for preparing preparations for injection or infusion. Suitable carriers for microcapsules, implants or rods are, for example, copolymers of glycolic acid and lactic acid.

The pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the vaccine containing the heparanase peptide, a functional variant thereof, or the nucleic acid encoding it, in combination with one or more active compounds to be administered, depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the heparanase peptide, a functional variant thereof, or the nucleic acid encoding it.

The vaccine containing the heparanase peptide according to the present invention, or a functional variant thereof, respectively the medicaments containing it, can be used for the treatment of all metastatic and invasive cancer types or tumors exhibiting an increased heparanase expression and/or activity. Examples of such cancer types comprise neuroblastoma, intestine carcinoma such as rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeoloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma.

Examples of invasive cancer types where the use of the vaccine containing the heparanase peptide according to the present invention, respectively the medicaments containing it, is particularly advantageous include breast carcinoma, lung carcinoma, prostate carcinoma and colon carcinoma. Most preferably, the heparanase peptide is useful for the treatment of breast carcinoma.

Furthermore, the vaccine containing the heparanase peptide according to the present invention, respectively the medicaments containing it, can also be used for the treatment of all autoimmune or other inflammatory diseases which are accompanied by an increased cell migration due to an enhanced heparanase activity.

Examples of autoimmune diseases include collagen diseases such as rheumatoid arthritis, Lupus erythematodes disseminatus, Sharp syndrome, CREST syndrome (calcinosis, Raynaud syndrome, esophageal dysmotility, teleangiectasia), dermatomyositis, vasculitis (Morbus Wegener) and Sjögren syndrome, renal diseases such as Goodpasture syndrome, rapidly-progressing glomerulonephritis and membrane-proliferative glomerulonephritis type II, endocrine diseases such as type-I diabetes, autoimmune polyendocrinopathy-candidiasis-ectodermal dystrophy (APECED), autoimmune parathyreoidism, pernicious anemia, gonad insufficiency, idiopathic Morbus Addison, hyperthyreosis, Hashimoto thyreoiditis and primary myxedemia, skin diseases such as Pemphigus vulgaris, bullous pemphigoid, Herpes gestationis, Epidermolysis bullosa and Erythema multiform major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, Myastenia gravis, myasthenic Lambert-Eaton syndrome, acquired neuromyotony, Guillain-Barré syndrome (Müller-Fischer syndrome), Stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

In a further embodiment, the present invention refers to a diagnostic method which can be used to determine the presence and frequency of T cells which are specific for a heparanase peptide of the present invention. The method comprises the following steps:
(a) isolating mononuclear cells from the peripheral blood or bone marrow of a patient,
(b) incubating the cells with heparanase-conjugated HLA tetramers, dimers or other multimers, and
(c) measuring the number of $CD8^+$- or $CD4^+$-/tetramer double-positive T cells.

Alternatively, the method can be employed by incubating the dendritic cells of a patient or animal to be diagnosed with heparanase peptide only and by determining the frequency of heparanase peptide specific T cells with the so-called Interferon-gamma Enzyme Linked immuno Assay (ELISpot), a technique which is known to the person skilled in the art and further described in Example 4.

Therefore, in a further aspect the invention refers to a diagnostic kit comprising at least a heparanase peptide, or a functional variant thereof, and/or the nucleic encoding it, optionally together with a HLA tetramer/dimer, and optionally together with other compounds (e.g. enzymes, chromophores, salts, buffers) which are necessary to perform an optimal measurement.

In line with the above described aspects of the invention, it follows that the disclosed heparanase peptides are useful in the treatment of patients suffering from a disease being associated with an enhanced heparanase expression.

Thus, the present invention further refers to a method of treating a disease being associated with an enhanced heparanase expression and/or activity, the method comprising administering a therapeutically effective amount of a vaccine containing a heparanase peptide, wherein the heparanase peptide is a nonapeptide having the sequence selected from the group consisting of SEQ ID NOs:1-505, or a functional derivative thereof.

Preferably, the heparanase peptide is a nonapeptide having the sequence selected from the group consisting of SEQ ID NOs:1, 2 and 3, or a functional derivative thereof. Even more preferably, the disease is a metastatic tumor.

BRIEF DESCRIPTION OF THE DRAWING

Table 1

Table 1 shows 505 heparanase derived nonamers (SEQ ID NOS: 1-505, respectively, in order of appearance), selected from full-length amino acid sequence of human heparanase according to their capacity to bind to HLA-A2 molecules. Calculated binding score (last column) decrease from the top to the bottom.

Table 2

Table 2 shows 475 heparanase derived 15-mers (SEQ ID NOS: 506-980, respectively, in order of appearance), selected from full-length amino acid sequence of human heparanase according to their capacity to bind to HLA-DR molecules. Calculated binding score (last column) decreases from top to the bottom.

The invention is further illustrated by the following examples.

EXAMPLES

Example 1

Peptides

Nonameric peptides with a potential (calculated) binding capacity to HLA-A2 molecules have been selected from the full-length amino acid sequence of human heparanase (gene bank accession no. NP 006656 and NM 006665). The search was carried out with the use of the SYFPEITHY database available on the world wide web. As examples, three peptides (heparanase p8: A L P P P L M L L), heparanase p16: L L L G P L G P L, and heparanase p183: D L I F G L N A L) have been synthesized in the laboratory of Dr. Pipkorn (German Cancer Research Centre). The peptides were dissolved in ddH$_2$O, 10% DMSO.

Example 2

Generation of Dendritic Cells (DC) and T-Lymphocytes (TC)

Mononuclear cells (MNC) from periphery blood (PB) and bone marrow (BM) were isolated via Ficoll gradients (Biocoll separating solution, Biochrom AG). MNC were washed two times with RPMI 1640, transferred to uncoated cell culture dishes, and grown for two hours at 37° C., 5% CO$_2$ in x-VIVO-20 media (BioWhittaker, Walkersville, Md.) for adhesion. Adherent cells were cultivated for 7 day in x-VIVO-20 media with the addition of GM-CSF (50 µg/ml; Behringwerke, Marburg) and IL-4 (1000 U/ml; Promocell, Heidelberg). Dendritic cells (DCs) were magnetically isolated via anti-CD-3-coated and anti-CD-19-coated magnetic beads (Dynal). Non-adherent cells were cultivated for 7 days in RPMI 1640 supplemented with 8% human AB sera (Sigma), rhuIL-2 (100 U/ml; Chiron, Ratingen) and IL-4 (60 U/ml). T cells (TCs) were purified via anti-CD-56-coated, anti-CD-19-coated and anti-CD-15-coated magnetic beads.

Example 3

HLA-Typing

HLA-typing of test patients was performed by staining of mononuclear cells with the hybridoma supernatant BB7.2 (mouse-anti-human-HLA-A2), and goat-anti-mouse-FITC (Immuno Research). The analysis was performed by fluorescent flow cytometry (FACSCan).

Example 4

IFN-γ Enzyme-Linked Immuno Assay (ELISpot)

The number of peptide-specific T-cells from the bone marrow (BMTCs) of female patients is determined by the ELISpot method. For this purpose, a 96-well ELISpot plate (Millipore) is coated with anti-human-IFNγ antibodies (ELISpot Kit, Mabtech) over night at 4° C. and then one hour blocked with RPMI 5% AB sera (37° C., 5% CO$_2$). $10^4$ DCs, $10^5$ TCs and 10 µg/ml peptide are cultivated on the IFN-γ-coated ELISpot plate for 40 hours (37° C., 5% CO$_2$). Supernatants are discarded and the plate is developed via the ELISpot kit (Mabtech). IFN-γ producing cells are counted with Axioplan Mikroskop (Zeiss) by using the KS ELISpot software. For negative controls, HIV or insulin peptides are used. Each group is determined in triplicate. Positive results are measured via the so-called T-test ($p<0.05$).

Results:

(BMTCs of 15 female breast cancer patients, insulin p34 [H L V E A L Y L V] (SEQ ID NO: 984) was used as negative control): 53% (8 out of 15) of the patients significantly reacted against human heparanase peptides. In particular, 20% (3/15) reacted against heparanase p8 (Hpa8), 33% (5/15) against heparanase p16 (Hpa16), and 40% (6/15) against Hpa183) (see Table 3).

TABLE 3

| Patient | Hpa p8 | | Hpa p16 | | Hpa p183 | |
|---|---|---|---|---|---|---|
| | p < 0.05 | frequency | p < 0.05 | frequency | p < 0.05 | frequency |
| 503 | 0.019 | 1:4100 | 0.012 | 1:3600 | 0.008 | 1:3500 |
| 505 | — | | — | | — | |
| 512 | — | | — | | — | |
| 579 | — | | 0.038 | 1:1700 | 0.043 | 1:1600 |
| 581 | — | | — | | 0.023 | 1:3000 |
| 595 | — | | — | | — | |
| 590 | — | | 0.023 | 1:1200 | — | |
| 639 | 0.008 | 1:650 | 0.039 | 1:580 | 0.017 | 1:660 |
| 662 | — | | — | | — | |
| 696 | — | | — | | — | |
| 704 | 0.025 | 1:2700 | — | | — | |
| 753 | — | | — | | 0.037 | 1:12500 |
| 756 | — | | — | | — | |
| 771 | — | | — | | — | |
| 790 | — | | 0.032 | 1:3200 | 0.045 | 1:6000 |

Differences between the patients in the positive responses against Heparanase Peptides

TABLE 3B

| Peptid | MaCa patient | | | | | | | | |
|---|---|---|---|---|---|---|---|---|---|
| | 503 | 579 | 581 | 590 | 639 | 704 | 753 | 790 | 923 |
| Heparanase 8 | x | | | | x | x | | | |
| Heparanase 16 | x | x | | x | x | | | x | x |
| Heparanase 183 | x | x | x | | x | | x | x | |
| MUC-1 | x | | | | | | | | x |
| Her2/neu | x | | | | | x | | | | x = positive (p value < 0.05) reaction of T cells in ELISpot
Empty boxes = reaction against insulin p value > 0.05

Example 5

Cytotoxicity Assay

The cytotoxic activity of peptide-specific T-cells is measured with a cytotoxicity assay (Chrome-51 Release Assay).

Isolated DCs and TCs are co-cultivated at a ratio ranging from 1:10 to 1:40 in RPMI supplemented with 8% AB sera and 20 U/l rhuIL-2 (recombinant human interleukin-2) for 7 days. At a day 0, (heparanase p8, heparanase p16, heparanase p183) at a concentration of 10 μg/ml are added. $5 \times 10^5$ target cells, MCF-7 cells (human breast epithelial cancer cells, mock- and hpahu-treated) are incubated with 200 μci radioactive chrome-51 for 90 minutes. Chromated targets and prestimulated TCs are titrated in triplicate and incubated for 4 hours at 37° C. and 5% $CO_2$. The supernatant is transferred to scintillation tubes and measured in a gamma-counter for 50 sec/tube.

Example 6

Tetramer Staining

Phycoerythrin (PE-)conjugated tetramer complexes consisting of HLA-A2 and either heparanase p8, heparanase p16 or HIV (S L Y N T V A T L) (SEQ ID NO: 985) peptides are obtained from the NAID facility (Bethesda, Maryland).

$10^6$ of each BM-MNC and PB-MNC are blocked with 5% endobulin (immunoglobulin G), incubated with tetramers on ice for 45 min and then stained with CD8-FITC (Becton Dickinson). Dead cells are identified by propidium iodide. The number of T-cells which are double positive for CD8 and tetramer are determined by flow cytometry.

Results:

HLA-A2peptide staining of 2 examined patients (MaCa numbers Table 4) revealed enriched fractions of CD8-positive T cells with specificity for i) heparanase-derived peptide Hpa.8-17/ALPPPLMLL (SEQ ID NO: 981) (see % values of CD8-positive T cells), and for ii) heparanase-derived peptide Hpa.16-23/LLLGPLGPL (SEQ ID NO: 982) (see % values of CD8-positive T cells). The staining of HLA-A2/HIV-peptide complexes as negative controls resulted in significantly lower values (0.1 and 0. 01 respectively). (see table 4)

TABLE 4

| MaCa | | Tetramer HIV | Tetramer Hpa 8 | Tetramer Hpa 16 |
|---|---|---|---|---|
| 889 | PBTC | — | — | — |
| | BMTC | 0.01% | 0.19% | 0.11% |
| 923 | PBTC | 0.09% | 0.55% | 3.05% |
| | BMTC | 0.06% | 0.34% | 5.7% |
| 959 | PBTC | 0.07% | 0.07% | 0.52% |
| | BMTC | 0.1% | 0.08% | 0.73% |
| 961 | PBTC | 0.1% | 0.05% | 0.14% |
| | BMTC | 0.05% | 0% | 0.33% |

The invention claimed is:

1. A heparanase peptide consisting of SEQ ID No. 1 that binds to a HLA molecule.

2. The heparanase peptide according to claim 1, wherein the HLA molecule is HLA-A2.

3. A composition comprising a heparanase peptide consisting of SEQ ID No. 1.

* * * * *